US011066677B2

(12) United States Patent
Park et al.

(10) Patent No.: US 11,066,677 B2
(45) Date of Patent: Jul. 20, 2021

(54) PLANTS WITH ENHANCED TOLERANCE TO MULTIPLE ABIOTIC STRESSES

(71) Applicants: Kansas State University Research Foundation, Manhattan, KS (US); Baylor College of Medicine, Houston, TX (US)

(72) Inventors: Sunghun Park, Manhattan, KS (US); Frank White, Manhattan, KS (US); Jungeun Park, Manhattan, KS (US); Kendal Hirschi, Houston, TX (US); Ning-Hui Cheng, Manvel, TX (US)

(73) Assignees: Kansas State University Research Foundation, Manhattan, KS (US); Baylor College of Medicine, Houston, TX (US)

( * ) Notice: Subject to any disclaimer, the term of this patent is extended or adjusted under 35 U.S.C. 154(b) by 325 days.

(21) Appl. No.: 15/618,792

(22) Filed: Jun. 9, 2017

(65) Prior Publication Data

US 2017/0275644 A1 Sep. 28, 2017

Related U.S. Application Data

(62) Division of application No. 14/241,992, filed as application No. PCT/US2012/053404 on Aug. 31, 2012, now abandoned.

(60) Provisional application No. 61/529,404, filed on Aug. 31, 2011.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8271* (2013.01)

(58) Field of Classification Search
None
See application file for complete search history.

(56) References Cited

U.S. PATENT DOCUMENTS

| | | | |
|---|---|---|---|
| 2006/0064784 A1* | 3/2006 | Chardonnens | A01N 65/00 800/289 |
| 2006/0217544 A1* | 9/2006 | Alexandrov | C12N 9/0036 536/23.6 |
| 2011/0131681 A1 | 6/2011 | Rathinasabapathi et al. | |
| 2011/0209241 A1 | 8/2011 | Hatzfeld et al. | |

OTHER PUBLICATIONS

Cheng et al., 2011, Journal of Biological Chemistry 286: 20398-20406.*
International Search Report and Written Opinion dated Jan. 29, 2013, in corresponding PCT/US2012/053404 filed Aug. 31, 2012.
Cheng, Ning-Hul, "Arobidopsis Monothiol Glutaredoxin, AtGRX17, Is Critical for Temperature-dependent Postembryonic Growth and Development via Modulating Auxin Response," Journal of Biological Chemistry, Jun. 10, 2011, vol. 286, No. 23.
Wu, Qingyu, "Ectopic Expression of Arabidopsis Glutaredoxin AtGRXS17 Enhances Thermotolerance in Tomato," Plant Biotechnology Journal, Jul. 5, 2012, pp. 1-11.
Park, Sung Hun, "Efficient and Genotype-independent Agrobacterium—mediated tomato transformation," Journal of Plant Physiology, 2003, pp. 1253-1257, vol. 160.
Thornton, Janet M. "From Structure to function: Approaches and limitations," Nature Structural Biology, Structural Genomics Supplement, Nov. 2000.
Shanker, Arun Kumar "Abiotic Stress Response in plants—physiological, biochemical and genetic perspectives," Intechweb.org, Jul. 2011.
Guo, Haiwei, "Protein tolerance to random amino acid change," PNAS, Jun. 22, 2004, vol. 101, No. 25 pp. 9205-9210.
Keskin, Ozlem "A new, structurally nonredundant, diverse data set of protein-protein interfaces and its implications," Protein Science, Jan. 9, 2004, pp. 1043-1055; vol. 13.
Cheng, Ning-Hui "AtGRXcp, an Arabidopsis Chloroplastic Glutaredoxin, Is Critical for Protection against Pretein Oxidative Damage," The Journal of Biological Chemistry, Sep. 8, 2006, pp. 26280-26288, vol. 281, No. 36.
Office Action dated Mar. 4, 2016, in U.S. Appl. No. 14/241,992, filed Feb. 28, 2014.
Office Action dated Jul. 14, 2016, in U.S. Appl. No. 14/241,992, filed Feb. 28, 2014.
Office Action dated Dec. 12, 2016, in U.S. Appl. No. 14/241,992, dated Feb. 28, 2014.

* cited by examiner

*Primary Examiner* — Bratislav Stankovic
(74) *Attorney, Agent, or Firm* — Hovey Williams LLP

(57) ABSTRACT

The present disclosure describes genetically-modified plants having enhanced tolerance to multiple abiotic stressors, such as extreme temperatures (heat or cold) and/or drought. Abiotic stress tolerance is enhanced by ectopic expression of a heterologous glutaredoxin. Abiotic stress tolerance (particularly drought) is also enhanced by inhibited function, activity, or expression of an endogenous glutaredoxin. Methods of producing such genetically-modified plants are also disclosed.

14 Claims, 23 Drawing Sheets

Specification includes a Sequence Listing.

| Gene name | Accession # | Forward primer | Reverse primer |
|---|---|---|---|
| LeHSP21 | U66300 | TGCGTTTTGACATGCCGGGA<br>SEQ ID NO: 10 | TCTGGGAGACTTAAACGAGTGTCG<br>SEQ ID NO: 11 |
| LeERHSP21.5 | Ab026983 | GGCATTGTGTTGAAAGGAGTCATGGA<br>SEQ ID NO: 12 | CCACAGAGAGAAACAGAGGATGAAC<br>SEQ ID NO: 13 |
| LeHSPMT | AB017134 | GCGGTGGAGGAGAACACGCT<br>SEQ ID NO: 14 | TCTCCGCCTTGATTCCATCCA<br>SEQ ID NO: 15 |
| HSFA1a | AW223133 | GGCAGCAAAGGCAATGTTGAGGGA<br>SEQ ID NO: 16 | TGGGAACATGTGCCAAGATGAGATGA<br>SEQ ID NO: 17 |
| HSFA2 | AK325085 | GGCGGTCTCTAGTAGCGCATGT<br>SEQ ID NO: 18 | TGGTTGAGGAAAGCCGAGTCCA<br>SEQ ID NO: 19 |

Fig. 5

Free GFP
25 °C
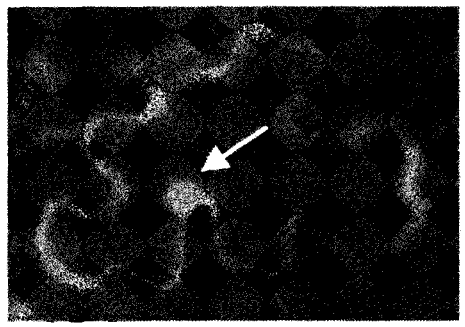
45 °C
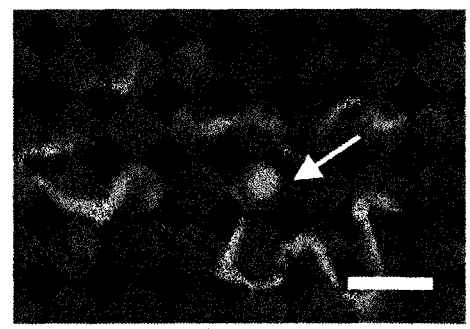
AtGRXS17-GFP
25 °C
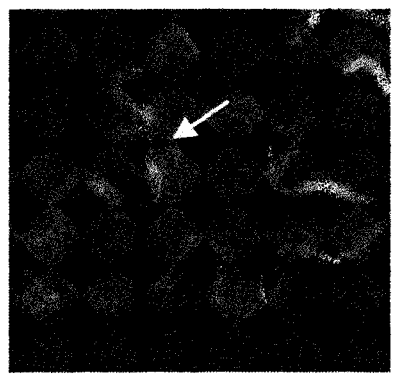
45 °C
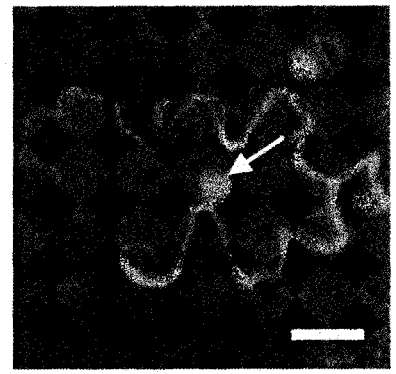
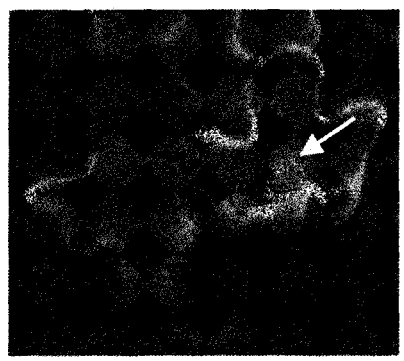
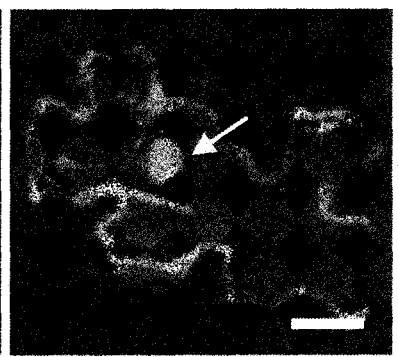
Fig. 6

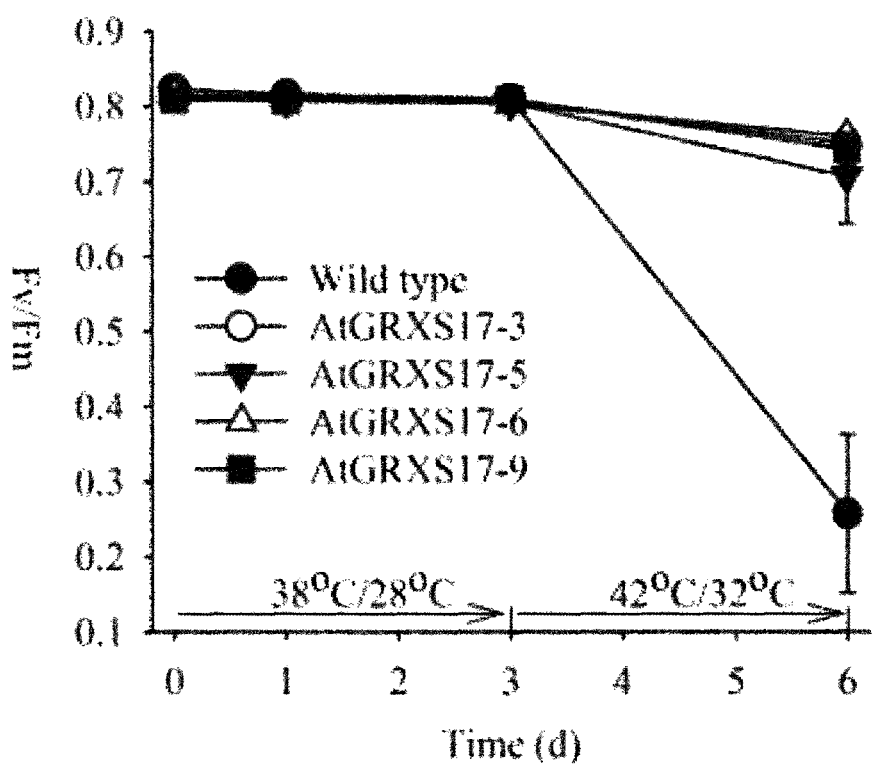
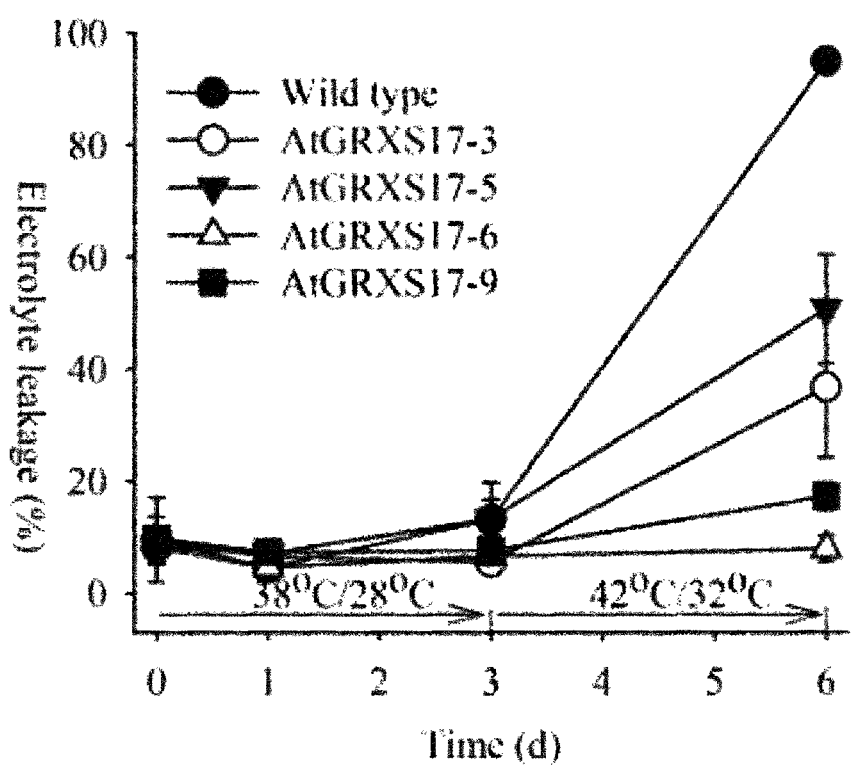
Fig. 13

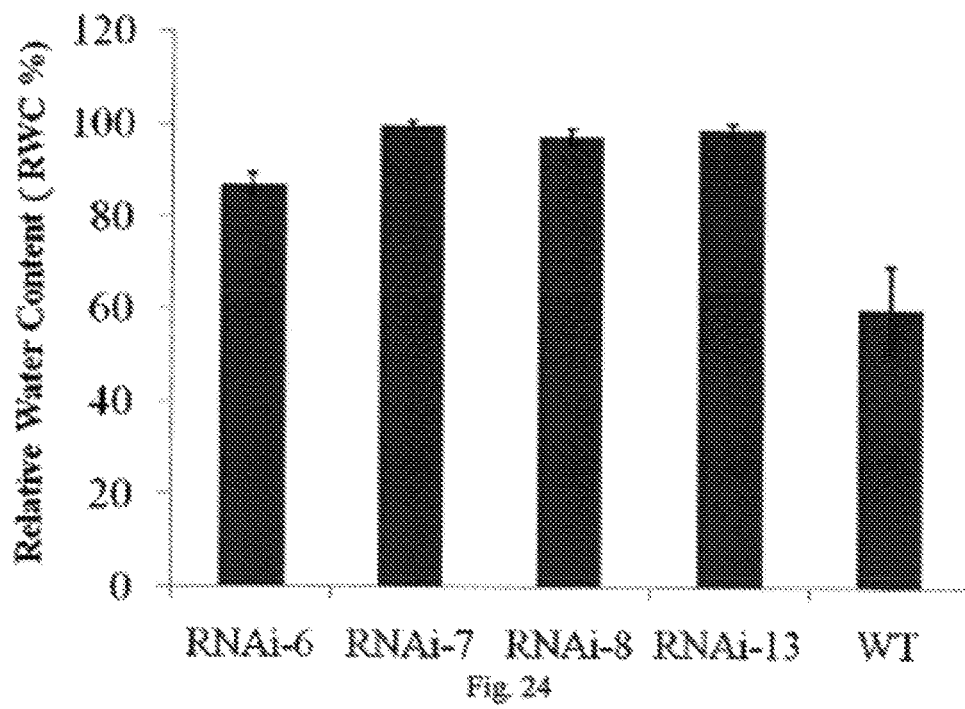

Fig. 24

| Gene name | Accession # | Primer sequence | SEQ ID NO: |
|---|---|---|---|
| SlABRE1 | AY530758 | Forward: ACCAACAATCACAGCCACAG | 20 |
| | | Reverse: TGCTCTTCCCAAGTCCATCT | 21 |
| SlCBF1 | AY034473.1 | Forward: GCTGGCAGGAAGAAGTTTCG | 22 |
| | | Reverse: GAGTTGGAGGAAGCAGGGATAG | 23 |
| SlCAT1 | M93719 | Forward: ATTGCTGCTGGAAACTATCCTGAG | 24 |
| | | Reverse: GGTCCAATACGGTGTCTCTGAGTA | 25 |
| SlPP2Acs (housekeeping gene) | AY325818 | Forward: CGATGTGTGATCTCCTATGGTC | 26 |
| | | Reverse: AAGCTGATGGGCTCTAGAAATC | 27 |

Fig. 25

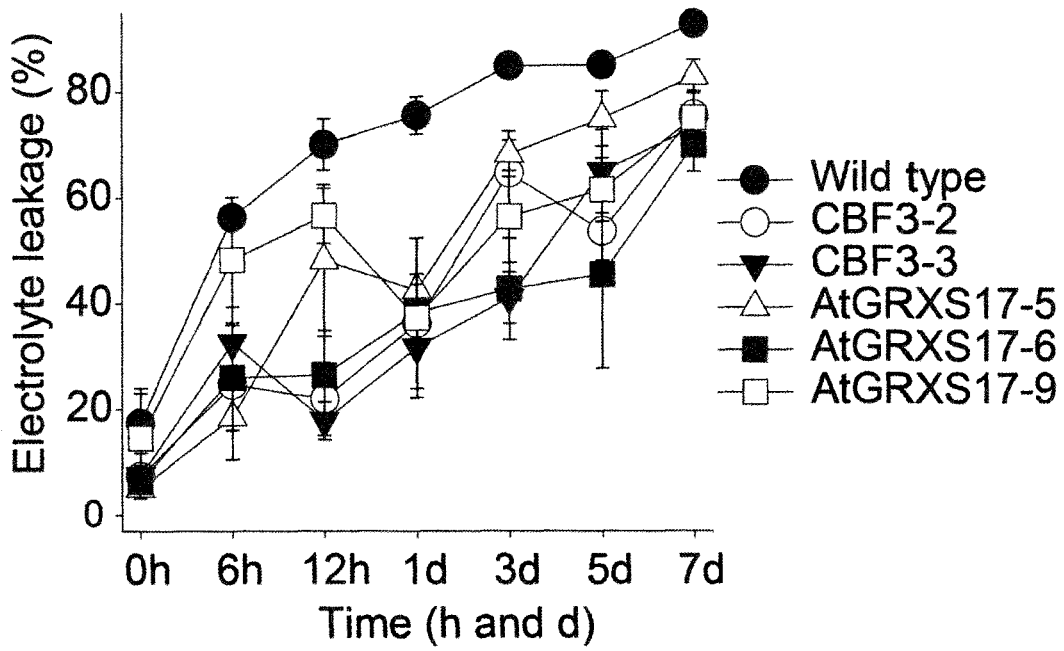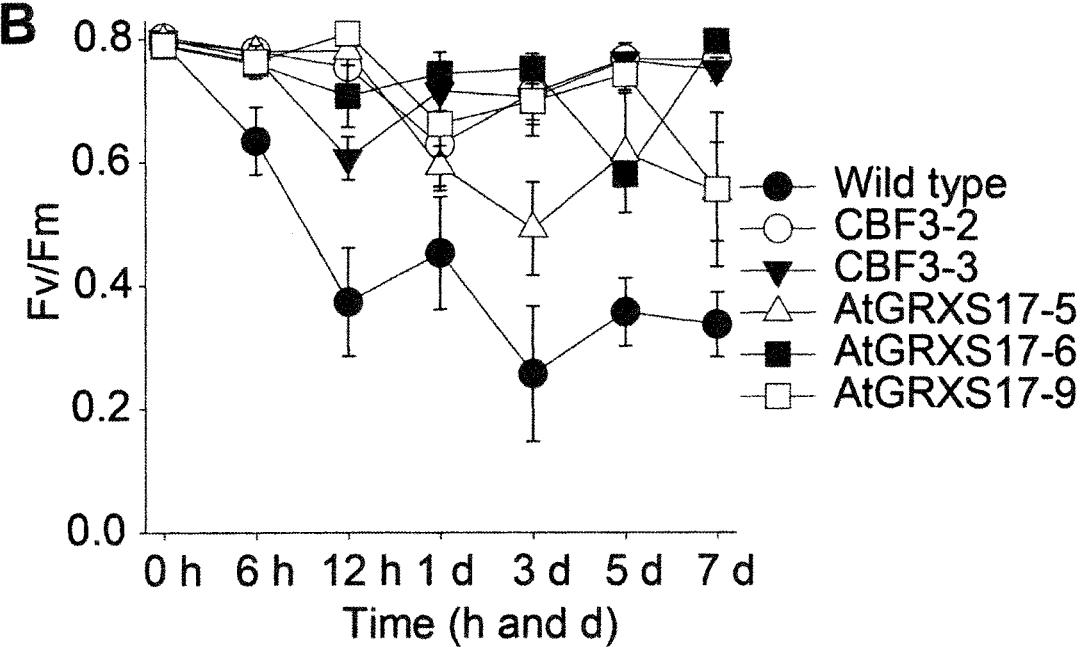
Fig. 30

SEQUENCE LISTING

<160> NUMBER OF SEQ ID NOS: 31

<210> SEQ ID NO 1
<211> LENGTH: 1467
<212> TYPE: DNA
<213> ORGANISM: Arabidopsis thaliana

<400> SEQUENCE: 1

```
atgagcggta cggtgaagga tatcgtttca aaggcggagc ttgataactt gcgccagagc      60
ggcgcaccag tcgtgcttca cttctgggct tcttggtgtg atgcttcgaa gcagatggat     120
caagttttct ctcatctcgc tactgatttc cctcgtgctc acttctttag ggttgaagct     180
gaggaacatc ctgagatatc tgaggcttac tctgttgctg ctgtgcctta tttcgtcttc     240
ttcaaggatg gtaaaactgt ggatacactt gagggtgcag atccatcaag tttagctaat     300
aaggttggca agttgctgg ttctagtact tctgcggagc tgctgctcc tgcaagctta      360 gggttggctg ctgggccaac gattcttgaa actgtgaagg agaatgcgaa agcttcttta     420
caagaccgag ctcagcctgt atctaccgcc gatgctctca agagccgttt ggaaaagctc     480
actaattctc accctgtcat gttattcatg aaaggtattc ctgaagagcc taggtgtggg     540
tttagcagga aagtagttga cattttgaaa gaggttaacg ttgattttgg aagttttgac     600
atactatcgg ataacgaagt gcgagagggt ttgaagaaat tctctaactg gccaacgttt     660
cctcagctgt actgcaacgg agagcttctt ggtggagctg atatcgcaat agcgatgcac     720
gagagcggtg aactaaaaga tgctttcaaa gatcttggga tcacgacagt tggttcaaaa     780
gaaagtcagg atgaagctgg aaaaggagga ggggttagtt caggaaacac aggcttaagt     840
gagaccctcc gagctcggct cgaaggtctg gtcaattcca aaccagttat gctgttcatg     900
aaaggaagac cagaagaacc aaagtgtggg ttcagtggga agtggttga aatcctcaac     960 caagaaaaaa tcgagtttgg gagtttcgat atcctcttag atgacgaagt tcgccaaggc    1020
cttaaagtgt attcaaactg gtcaagctat cctcagcttt acgtgaaagg cgagcttatg    1080
ggtggatcag acattgtctt ggagatgcaa aagagcggtg agctgaaaaa ggtcttgacc    1140
gagaaaggga tcactggaga acagagtctt gaagatagat tgaaggcact gatcaattcc    1200
tcggaagtaa tgctattcat gaaaggttca ccagatgaac cgaaatgcgg atttagctcc    1260
aaagttgtga aagcattgag aggagaaaac gtgagtttcg gatcgtttga tatcttgact    1320
gatgaagaag taaggcaagg gattaagaat ttctcaaact ggccaacttt tcctcagcta    1380
tactacaaag gtgagttaat tggaggatgt gatatcatta tggagctaag tgagagtggt    1440
gatctcaaag caactctatc cgagtaa                                         1467
```

<210> SEQ ID NO 2
<211> LENGTH: 488
<212> TYPE: PRT
<213> ORGANISM: Arabidopsis thaliana

<400> SEQUENCE: 2

Met Ser Gly Thr Val Lys Asp Ile Val Ser Lys Ala Glu Leu Asp Asn

-continued

```
1               5                   10                  15
Leu Arg Gln Ser Gly Ala Pro Val Val Leu His Phe Trp Ala Ser Trp
                20                  25                  30

Cys Asp Ala Ser Lys Gln Met Asp Gln Val Phe Ser His Leu Ala Thr
                35                  40                  45

Asp Phe Pro Arg Ala His Phe Arg Val Glu Ala Glu Glu His Pro
    50                  55                  60

Glu Ile Ser Glu Ala Tyr Ser Val Ala Val Pro Tyr Phe Val Phe
65                  70                  75                  80

Phe Lys Asp Gly Lys Thr Val Asp Thr Leu Glu Gly Ala Asp Pro Ser
                85                  90                  95

Ser Leu Ala Asn Lys Val Gly Lys Val Ala Gly Ser Thr Ser Ala
                100                 105                 110

Glu Pro Ala Ala Pro Ala Ser Leu Gly Leu Ala Ala Gly Pro Thr Ile
                115                 120                 125

Leu Glu Thr Val Lys Glu Asn Ala Lys Ala Ser Leu Gln Asp Arg Ala
                130                 135                 140

Gln Pro Val Ser Thr Ala Asp Ala Leu Lys Ser Arg Leu Glu Lys Leu
145                 150                 155                 160

Thr Asn Ser His Pro Val Met Leu Phe Met Lys Gly Ile Pro Glu Glu
                165                 170                 175

Pro Arg Cys Gly Phe Ser Arg Lys Val Val Asp Ile Leu Lys Glu Val
                180                 185                 190

Asn Val Asp Phe Gly Ser Phe Asp Ile Leu Ser Asp Asn Glu Val Arg
                195                 200                 205

Glu Gly Leu Lys Lys Phe Ser Asn Trp Pro Thr Phe Pro Gln Leu Tyr
                210                 215                 220

Cys Asn Gly Glu Leu Leu Gly Gly Ala Asp Ile Ala Ile Ala Met His
225                 230                 235                 240

Glu Ser Gly Glu Leu Lys Asp Ala Phe Lys Asp Leu Gly Ile Thr Thr
                245                 250                 255

Val Gly Ser Lys Glu Ser Gln Asp Glu Ala Gly Lys Gly Gly Val
                260                 265                 270

Ser Ser Gly Asn Thr Gly Leu Ser Glu Thr Leu Arg Ala Arg Leu Glu
                275                 280                 285

Gly Leu Val Asn Ser Lys Pro Val Met Leu Phe Met Lys Gly Arg Pro
                290                 295                 300

Glu Glu Pro Lys Cys Gly Phe Ser Gly Lys Val Val Glu Ile Leu Asn
305                 310                 315                 320

Gln Glu Lys Ile Glu Phe Gly Ser Phe Asp Ile Leu Leu Asp Asp Glu
                325                 330                 335

Val Arg Gln Gly Leu Lys Val Tyr Ser Asn Trp Ser Ser Tyr Pro Gln
                340                 345                 350

Leu Tyr Val Lys Gly Glu Leu Met Gly Gly Ser Asp Ile Val Leu Glu
                355                 360                 365

Met Gln Lys Ser Gly Glu Leu Lys Lys Val Leu Thr Glu Lys Gly Ile
                370                 375                 380

Thr Gly Glu Gln Ser Leu Glu Asp Arg Leu Lys Ala Leu Ile Asn Ser
385                 390                 395                 400

Ser Glu Val Met Leu Phe Met Lys Gly Ser Pro Asp Glu Pro Lys Cys
                405                 410                 415

Gly Phe Ser Ser Lys Val Val Lys Ala Leu Arg Gly Glu Asn Val Ser
                420                 425                 430
```

```
Phe Gly Ser Phe Asp Ile Leu Thr Asp Glu Glu Val Arg Gln Gly Ile
        435                 440                 445

Lys Asn Phe Ser Asn Trp Pro Thr Phe Pro Gln Leu Tyr Tyr Lys Gly
    450                 455                 460

Glu Leu Ile Gly Gly Cys Asp Ile Ile Met Glu Leu Ser Glu Ser Gly
465                 470                 475                 480

Asp Leu Lys Ala Thr Leu Ser Glu
                485

<210> SEQ ID NO 3
<211> LENGTH: 2202
<212> TYPE: DNA
<213> ORGANISM: Artificial Sequence
<220> FEATURE:
<223> OTHER INFORMATION: ATGRXS17-GFP FUSION PROTEIN CODING SEQUENCE

<400> SEQUENCE: 3
atgagcggta cggtgaagga tatcgtttca aaggcggagc ttgataactt gcgccagagc       60
ggcgcaccag tcgtgcttca cttctgggct tcttggtgtg atgcttcgaa gcagatggat      120
caagttttct ctcatctcgc tactgatttc cctcgtgctc acttctttag ggttgaagct      180
gaggaacatc ctgagatatc tgaggcttac tctgttgctg ctgtgcctta tttcgtcttc      240
ttcaaggatg gtaaaactgt ggatacactt gagggtgcag atccatcaag tttagctaat      300
aaggttggca agttgctgg ttctagtact tctgcggagc tgctgctcc tgcaagctta       360 gggttggctg ctgggccaac gattcttgaa actgtgaagg agaatgcgaa agcttcttta      420
caagaccgag ctcagcctgt atctaccgcc gatgctctca gagccgtttt ggaaaagctc      480
actaattctc accctgtcat gttattcatg aaaggtattc ctgaagagcc taggtgtggg      540
tttagcagga agtagttga cattttgaaa gaggttaacg ttgattttgg aagttttgac       600
atactatcgg ataacgaagt gcgagagggt ttgaagaaat ctctaactg gccaacgttt       660 cctcagctgt actgcaacgg agagcttctt ggtggagctg atatcgcaat agcgatgcac      720
gagagcggtg aactaaaaga tgcttttcaa gatcttggga tcacgacagt tggttcaaaa      780
gaaagtcagg atgaagctgg aaaaggagga ggggttagtt caggaaacac aggcttaagt      840
gagaccctcc gagctcggct cgaaggtctg gtcaattcca aaccagttat gctgttcatg      900
aaaggaagac cagaagaacc aaagtgtggg ttcagtggga agtggttga atcctcaac       960 caagaaaaaa tcgagtttgg gagtttcgat atcctcttag atgacgaagt tcgccaaggc     1020
cttaaagtgt attcaaactg gtcaagctat cctcagcttt acgtgaaagg cgagcttatg     1080
ggtggatcag acattgtctt ggagatgcaa aagagcggtg agctgaaaaa ggtcttgacc     1140
gagaaaggga tcactggaga acagagtctt gaagatagat tgaaggcact gatcaattcc     1200
tcggaagtaa tgctattcat gaaaggttca ccagatgaac cgaaatgcgg atttagctcc     1260
aaagttgtga agcattgag aggagaaaac gtgagttccg gatcgtttga tatcttgact     1320
gatgaagaag taaggcaagg gattaagaat ttctcaaact ggccaacttt tcctcagcta     1380
tactacaaag gtgagttaat tggaggatgt gatatcatta tggagctaag tgagagtggt     1440
gatctcaaag caactctatc cgaggggatc caagagata taacaatgag taaaggagaa     1500
gaacttttca ctggagttgt cccaattctt gttgaattag atggtgatgt taatgggcac     1560
aaattttctg tcagtggaga gggtgaaggt gatgcaacat acggaaaact taccctttaaa     1620 tttatttgca ctactggaaa actacctgtt ccatggccaa cacttgtcac tactttctct     1680
```

```
tatggtgttc aatgcttttc aagatacccca gatcatatga agcggcacga cttcttcaag    1740
agcgccatgc ctgagggata cgtgcaggag aggaccatct ctttcaagga cgacgggaac    1800
tacaagacac gtgctgaagt caagtttgag ggagacaccc tcgtcaacag gatcgagctt    1860
aagggaatcg atttcaagga ggacggaaac atcctcggcc acaagttgga atacaactac    1920
aactcccaca acgtatacat cacggcagac aaacaaaaga atggaatcaa agctaacttc    1980
aaaattagac acaacattga agatggaagc gttcaactag cagaccatta tcaacaaaat    2040
actccaattg gcgatggccc tgtccttttta ccagacaacc attacctgtc cacacaatct    2100
gccctttcga agatcccaa cgaaaagaga gaccacatgg tccttcttga gtttgtaaca    2160
gctgctggga ttacacatgg catggatgaa ctatacaaat aa                        2202
```

<210> SEQ ID NO 4
<211> LENGTH: 733
<212> TYPE: PRT
<213> ORGANISM: Artificial Sequence
<220> FEATURE:
<223> OTHER INFORMATION: ATGRXS17-GFP FUSION PROTEIN

<400> SEQUENCE: 4

```
Met Ser Gly Thr Val Lys Asp Ile Val Ser Lys Ala Glu Leu Asp Asn
1               5                   10                  15

Leu Arg Gln Ser Gly Ala Pro Val Val Leu His Phe Trp Ala Ser Trp
            20                  25                  30

Cys Asp Ala Ser Lys Gln Met Asp Gln Val Phe Ser His Leu Ala Thr
        35                  40                  45

Asp Phe Pro Arg Ala His Phe Phe Arg Val Glu Ala Glu Glu His Pro
    50                  55                  60

Glu Ile Ser Glu Ala Tyr Ser Val Ala Ala Val Pro Tyr Phe Val Phe
65                  70                  75                  80

Phe Lys Asp Gly Lys Thr Val Asp Thr Leu Glu Gly Ala Asp Pro Ser
                85                  90                  95

Ser Leu Ala Asn Lys Val Gly Lys Val Ala Gly Ser Ser Thr Ser Ala
            100                 105                 110

Glu Pro Ala Ala Pro Ala Ser Leu Gly Leu Ala Ala Gly Pro Thr Ile
        115                 120                 125

Leu Glu Thr Val Lys Glu Asn Ala Lys Ala Ser Leu Gln Asp Arg Ala
    130                 135                 140

Gln Pro Val Ser Thr Ala Asp Ala Leu Lys Ser Arg Leu Glu Lys Leu
145                 150                 155                 160

Thr Asn Ser His Pro Val Met Leu Phe Met Lys Gly Ile Pro Glu Glu
                165                 170                 175

Pro Arg Cys Gly Phe Ser Arg Lys Val Val Asp Ile Leu Lys Glu Val
            180                 185                 190

Asn Val Asp Phe Gly Ser Phe Asp Ile Leu Ser Asp Asn Glu Val Arg
        195                 200                 205

Glu Gly Leu Lys Lys Phe Ser Asn Trp Pro Thr Phe Pro Gln Leu Tyr
    210                 215                 220

Cys Asn Gly Glu Leu Leu Gly Gly Ala Asp Ile Ala Ile Ala Met His
225                 230                 235                 240

Glu Ser Gly Glu Leu Lys Asp Ala Phe Lys Asp Leu Gly Ile Thr Thr
                245                 250                 255

Val Gly Ser Lys Glu Ser Gln Asp Glu Ala Gly Lys Gly Gly Val
            260                 265                 270
```

```
Ser Ser Gly Asn Thr Gly Leu Ser Glu Thr Leu Arg Ala Arg Leu Glu
            275                 280                 285

Gly Leu Val Asn Ser Lys Pro Val Met Leu Phe Met Lys Gly Arg Pro
        290                 295                 300

Glu Glu Pro Lys Cys Gly Phe Ser Gly Lys Val Val Glu Ile Leu Asn
305                 310                 315                 320

Gln Glu Lys Ile Glu Phe Gly Ser Phe Asp Ile Leu Leu Asp Asp Glu
                325                 330                 335

Val Arg Gln Gly Leu Lys Val Tyr Ser Asn Trp Ser Ser Tyr Pro Gln
            340                 345                 350

Leu Tyr Val Lys Gly Glu Leu Met Gly Gly Ser Asp Ile Val Leu Glu
        355                 360                 365

Met Gln Lys Ser Gly Glu Leu Lys Lys Val Leu Thr Glu Lys Gly Ile
    370                 375                 380

Thr Gly Glu Gln Ser Leu Glu Asp Arg Leu Lys Ala Leu Ile Asn Ser
385                 390                 395                 400

Ser Glu Val Met Leu Phe Met Lys Gly Ser Pro Asp Glu Pro Lys Cys
                405                 410                 415

Gly Phe Ser Ser Lys Val Val Lys Ala Leu Arg Gly Glu Asn Val Ser
            420                 425                 430

Phe Gly Ser Phe Asp Ile Leu Thr Asp Glu Glu Val Arg Gln Gly Ile
        435                 440                 445

Lys Asn Phe Ser Asn Trp Pro Thr Phe Pro Gln Leu Tyr Tyr Lys Gly
    450                 455                 460

Glu Leu Ile Gly Gly Cys Asp Ile Ile Met Glu Leu Ser Glu Ser Gly
465                 470                 475                 480

Asp Leu Lys Ala Thr Leu Ser Glu Gly Ile Gln Gly Asp Ile Thr Met
                485                 490                 495

Ser Lys Gly Glu Glu Leu Phe Thr Gly Val Val Pro Ile Leu Val Glu
            500                 505                 510

Leu Asp Gly Asp Val Asn Gly His Lys Phe Ser Val Ser Gly Glu Gly
        515                 520                 525

Glu Gly Asp Ala Thr Tyr Gly Lys Leu Thr Leu Lys Phe Ile Cys Thr
    530                 535                 540

Thr Gly Lys Leu Pro Val Pro Trp Pro Thr Leu Val Thr Thr Phe Ser
545                 550                 555                 560

Tyr Gly Val Gln Cys Phe Ser Arg Tyr Pro Asp His Met Lys Arg His
                565                 570                 575

Asp Phe Phe Lys Ser Ala Met Pro Glu Gly Tyr Val Gln Glu Arg Thr
            580                 585                 590

Ile Ser Phe Lys Asp Asp Gly Asn Tyr Lys Thr Arg Ala Glu Val Lys
        595                 600                 605

Phe Glu Gly Asp Thr Leu Val Asn Arg Ile Glu Leu Lys Gly Ile Asp
    610                 615                 620

Phe Lys Glu Asp Gly Asn Ile Leu Gly His Lys Leu Glu Tyr Asn Tyr
625                 630                 635                 640

Asn Ser His Asn Val Tyr Ile Thr Ala Asp Lys Gln Lys Asn Gly Ile
                645                 650                 655

Lys Ala Asn Phe Lys Ile Arg His Asn Ile Glu Asp Gly Ser Val Gln
            660                 665                 670

Leu Ala Asp His Tyr Gln Gln Asn Thr Pro Ile Gly Asp Gly Pro Val
        675                 680                 685

Leu Leu Pro Asp Asn His Tyr Leu Ser Thr Gln Ser Ala Leu Ser Lys
```

```
                690                 695                 700
Asp Pro Asn Glu Lys Arg Asp His Met Val Leu Leu Glu Phe Val Thr
705                 710                 715                 720

Ala Ala Gly Ile Thr His Gly Met Asp Glu Leu Tyr Lys
                725                 730
```

<210> SEQ ID NO 5
<211> LENGTH: 1476
<212> TYPE: DNA
<213> ORGANISM: Oryza sativa

<400> SEQUENCE: 5

```
atggcggcgg tgagggaggt ggggtcgaag gcggagctgg aggcggcggc gggaggggcg      60
cgggccgccg cggtgcactt ctgggcggcg tggtgcgagg cgtccaagca gatggacgag     120
gtcttcgcgc acctcgccgt cgacttctcc cacgccgtct cctccgggt tgaagctgag      180
gaacaacccg aaatttcaga ggcatatgga gttacagcag tgccatattt tgttttcttg     240
aaggaaggta aaactgttga tactctggag ggtgcaaatc cagccagctt ggccaataag     300
gttgcaaagt tagctgggcc tgccagcgtt gctgagtctg ctgtgcctgc tagcctgggt     360
gtggctgctg ggcctgctgt acttgaaaag gttcaagaga tggcacagca aaatggagct     420
tctgccacta gtagtgcaga gatgcattg aacaagagat tggagcagct tgtcaattcc      480
catcccgtct tctatttat gaagggaacc cctgagcaac aaggtgtgg tttcagtcga      540
aaagtagttg acgttttgaa gcaggaagga gttgaatttg ggagctttga catcctaaca     600
gataacgatg tacgtgaagg aatgaaaaag ttctcaaact ggccgacttt tcctcagctc     660
tactgcaaag gtgagctgct tggtggatgt gatattgtga ttgctatgca tgaaagcggt     720
gaactgaagg atgttttaa ggagcacaac attccgctgc agccacaggg aagcaaaaac      780
gaggaggcag tgaaagccaa gcctgatact gagaagagtg gtgcagtttc tgaaccagct     840
ttgcttactc agctcagaa ggaacgcttg gaaagccttg ttaatttcag cacagtgatg      900
gcatttataa aaggtacacc tgaggagccc aagtgtggat tcagtggaaa actagtgcat     960
attcttaagc aagagaagat cccttttctca agttttgaca ttcttacgga tgatgaggtt    1020
aggcagggtc taaagcttct ctcaaactgg cctagttacc ctcaactgta cataaacggt    1080
gaactggttg gcggatcaga cattgttatg gagatgcata gagtgggga gcttaagaag    1140
gttctatctg agaaagggat cgttgcgaaa gaaagtctag aagaccgcct gaaggccctg    1200
atttcctctg ccccagtgat gctcttcatg aagggcaccc cagatgcccc cgctgcggc    1260
ttcagttcga aggttgtgaa tgcactgaag caagcaggag tcagcttcgg agcgttcgac    1320
atcctatccg acgaggaggt taggcaaggc ttgaagacgt actccaactg cccacgttc    1380
cctcagctgt actacaaatc agaactgatt ggaggctgtg acatcgttct tgagctggag    1440
aagagtggag agctgaagtc cacgctttcg gagtga                                1476
```

<210> SEQ ID NO 6
<211> LENGTH: 491
<212> TYPE: PRT
<213> ORGANISM: Oryza sativa

<400> SEQUENCE: 6

```
Met Ala Ala Val Arg Glu Val Gly Ser Lys Ala Glu Leu Glu Ala Ala
1               5                   10                  15

Ala Gly Gly Ala Arg Ala Ala Ala Val His Phe Trp Ala Ala Trp Cys
            20                  25                  30
```

Glu Ala Ser Lys Gln Met Asp Glu Val Phe Ala His Leu Ala Val Asp
            35                  40                  45

Phe Ser His Ala Val Phe Leu Arg Val Glu Ala Glu Gln Pro Glu
 50                  55                  60

Ile Ser Glu Ala Tyr Gly Val Thr Ala Val Pro Tyr Phe Val Phe Leu
 65                  70                  75                  80

Lys Glu Gly Lys Thr Val Asp Thr Leu Glu Gly Ala Asn Pro Ala Ser
                    85                  90                  95

Leu Ala Asn Lys Val Ala Lys Leu Ala Gly Pro Ala Ser Val Ala Glu
                100                 105                 110

Ser Ala Val Pro Ala Ser Leu Gly Val Ala Ala Gly Pro Ala Val Leu
                115                 120                 125

Glu Lys Val Gln Glu Met Ala Gln Gln Asn Gly Ala Ser Ala Thr Ser
                130                 135                 140

Ser Ala Glu Asp Ala Leu Asn Lys Arg Leu Glu Gln Leu Val Asn Ser
145                 150                 155                 160

His Pro Val Phe Leu Phe Met Lys Gly Thr Pro Glu Gln Pro Arg Cys
                165                 170                 175

Gly Phe Ser Arg Lys Val Val Asp Val Leu Lys Gln Glu Gly Val Glu
                180                 185                 190

Phe Gly Ser Phe Asp Ile Leu Thr Asp Asn Asp Val Arg Glu Gly Met
                195                 200                 205

Lys Lys Phe Ser Asn Trp Pro Thr Phe Pro Gln Leu Tyr Cys Lys Gly
                210                 215                 220

Glu Leu Leu Gly Gly Cys Asp Ile Val Ile Ala Met His Glu Ser Gly
225                 230                 235                 240

Glu Leu Lys Asp Val Phe Lys Glu His Asn Ile Pro Leu Gln Pro Gln
                245                 250                 255

Gly Ser Lys Asn Glu Glu Ala Val Lys Ala Lys Pro Asp Thr Glu Lys
                260                 265                 270

Ser Gly Ala Val Ser Glu Pro Ala Leu Leu Thr Ala Ala Gln Lys Glu
                275                 280                 285

Arg Leu Glu Ser Leu Val Asn Phe Ser Thr Val Met Ala Phe Ile Lys
                290                 295                 300

Gly Thr Pro Glu Glu Pro Lys Cys Gly Phe Ser Gly Lys Leu Val His
305                 310                 315                 320

Ile Leu Lys Gln Glu Lys Ile Pro Phe Ser Ser Phe Asp Ile Leu Thr
                325                 330                 335

Asp Asp Glu Val Arg Gln Gly Leu Lys Leu Leu Ser Asn Trp Pro Ser
                340                 345                 350

Tyr Pro Gln Leu Tyr Ile Asn Gly Glu Leu Val Gly Gly Ser Asp Ile
                355                 360                 365

Val Met Glu Met His Lys Ser Gly Glu Leu Lys Lys Val Leu Ser Glu
                370                 375                 380

Lys Gly Ile Val Ala Lys Glu Ser Leu Glu Asp Arg Leu Lys Ala Leu
385                 390                 395                 400

Ile Ser Ser Ala Pro Val Met Leu Phe Met Lys Gly Thr Pro Asp Ala
                405                 410                 415

Pro Arg Cys Gly Phe Ser Ser Lys Val Val Asn Ala Leu Lys Gln Ala
                420                 425                 430

Gly Val Ser Phe Gly Ala Phe Asp Ile Leu Ser Asp Glu Glu Val Arg
                435                 440                 445

```
Gln Gly Leu Lys Thr Tyr Ser Asn Trp Pro Thr Phe Pro Gln Leu Tyr
        450                 455                 460
Tyr Lys Ser Glu Leu Ile Gly Gly Cys Asp Ile Val Leu Glu Leu Glu
465                 470                 475                 480
Lys Ser Gly Glu Leu Lys Ser Thr Leu Ser Glu
                485                 490

<210> SEQ ID NO 7
<211> LENGTH: 1949
<212> TYPE: DNA
<213> ORGANISM: Oryza sativa

<400> SEQUENCE: 7
```

| | | | | | |
|---|---|---|---|---|---|
| aaaaggaaag | cagaggaaaa | ccccaagccg | caagccccc | cgccgcgagt | cgtcttctca |     60 |
| tctctcctcc | gccgccgccg | cctgctgctg | catctctcgt | cgtcgccggt | gagggaaggg |    120 |
| aggggagggg | ggagggcgtg | atggcggcgg | tgagggaggt | ggggtcgaag | gcggagctgg |    180 |
| aggcggcggc | gggaggggcg | cgggccgccg | cggtgcactt | ctgggcggcg | tggtgcgagg |    240 |
| cgtccaagca | gatggacgag | gtcttcgcgc | acctcgccgt | cgacttctcc | cacgccgtct |    300 |
| tcctccgggt | tgaagctgag | gaacaaccg | aaatttcaga | ggcatatgga | gttacagcag |    360 |
| tgccatattt | tgttttcttg | aaggaaggta | aaactgttga | tactctggag | ggtgcaaatc |    420 |
| cagccagctt | ggccaataag | gttgcaaagt | tagctgggcc | tgccagcgtt | gctgagtctg |    480 |
| ctgtgcctgc | tagcctgggt | gtggctgctg | ggcctgctgt | acttgaaaag | gttcaagaga |    540 |
| tggcacagca | aaatggagct | tctgccacta | gtagtgcaga | gatgcattg | aacaagagat |    600 |
| tggagcagct | tgtcaattcc | catcccgtct | tcttatttat | gaagggaacc | cctgagcaac |    660 |
| caaggtgtgg | tttcagtcga | aaagtagttg | acgttttgaa | gcaggaagga | gttgaatttg |    720 |
| ggagctttga | catcctaaca | gataacgatg | tacgtgaagg | aatgaaaaag | ttctcaaact |    780 |
| ggccgacttt | tcctcagctc | tactgcaaag | gtgagctgct | tggtggatgt | gatattgtga |    840 |
| ttgctatgca | tgaaagcggt | gaactgaagg | atgtttttaa | ggagcacaac | attccgctgc |    900 |
| agccacaggg | aagcaaaaac | gaggaggcag | tgaaagccaa | gcctgatact | gagaagagtg |    960 |
| gtgcagtttc | tgaaccagct | tgcttactg | cagctcagaa | ggaacgcttg | gaaagccttg |   1020 |
| ttaatttcag | cacagtgatg | gcatttataa | aaggtacacc | tgaggagccc | aagtgtggat |   1080 |
| tcagtggaaa | actagtgcat | attccttaagc | aagagaagat | ccctttctca | agttttgaca |   1140 |
| ttcttacgga | tgatgaggtt | aggcagggtc | taaagcttct | ctcaaactgg | cctagttacc |   1200 |
| ctcaactgta | cataaacggt | gaactggttg | gcggatcaga | cattgttatg | gagatgcata |   1260 |
| agagtgggga | gcttaagaag | gttctatctg | agaaagggat | cgttgcgaaa | gaaagtctag |   1320 |
| aagaccgcct | gaaggccctg | atttcctctg | ccccagtgat | gctcttcatg | aagggcaccc |   1380 |
| cagatgcccc | ccgctgcggc | ttcagttcga | aggttgtgaa | tgcactgaag | caagcaggag |   1440 |
| tcagcttcgg | agcgttcgac | atcctatccg | acgaggaggt | taggcaaggc | ttgaagacgt |   1500 |
| actccaactg | gcccacgttc | cctcagctgt | actacaaatc | agaactgatt | ggaggctgtg |   1560 |
| acatcgttct | tgagctggag | aagagtggag | agctgaagtc | cacgctttcg | gagtgaggaa |   1620 |
| aatttaccgt | cgtatccgca | tcttcctctt | cctggtgttt | ctaccatccg | tcgaccatcg |   1680 |
| agtttgctct | attgatggca | ttttcttgta | ttcatagatc | cgtatttcaa | acttagatat |   1740 |
| atgcctgtgc | cacatcgctt | ttaactgtga | catctgcaga | agaataacta | agacgacctg |   1800 |
| ttcagtacgg | ctaataacta | agacgacctg | ttcagtacgg | ttatattgcc | agttcatttt |   1860 |

```
gccgcctcgc tttcgctctg ccttgaagcg ttgcaacttc cttattatcg caattaatag    1920
agggtgcttt agaaaattag aatgtacgc                                      1949
```

<210> SEQ ID NO 8
<211> LENGTH: 21
<212> TYPE: DNA
<213> ORGANISM: Artificial Sequence
<220> FEATURE:
<223> OTHER INFORMATION: Synthetic primer sequence

<400> SEQUENCE: 8

```
atgagcggta cggtgaagga t                                               21
```

<210> SEQ ID NO 9
<211> LENGTH: 21
<212> TYPE: DNA
<213> ORGANISM: Artificial Sequence
<220> FEATURE:
<223> OTHER INFORMATION: Synthetic primer sequence

<400> SEQUENCE: 9

```
tagctcggat agagttgctt t                                               21
```

<210> SEQ ID NO 10
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 10

```
tgcgttttga catgccggga                                                 20
```

<210> SEQ ID NO 11
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 11

```
tctgggagac ttaaacgagt gtcg                                            24
```

<210> SEQ ID NO 12
<211> LENGTH: 26
<212> TYPE: DNA
<213> ORGANISM: Artificial Sequence
<220> FEATURE:
<223> OTHER INFORMATION: Synthetic primer sequence

<400> SEQUENCE: 12

```
ggcattgtgt tgaaaggagt catgga                                          26
```

<210> SEQ ID NO 13
<211> LENGTH: 25
<212> TYPE: DNA
<213> ORGANISM: Artificial Sequence
<220> FEATURE:
<223> OTHER INFORMATION: Synthetic primer sequence

<400> SEQUENCE: 13

```
ccacagagag aaacagagga tgaac                                           25
```

<210> SEQ ID NO 14
<211> LENGTH: 20

```
<212> TYPE: DNA
<213> ORGANISM: Artificial Sequence
<220> FEATURE:
<223> OTHER INFORMATION: Synthetic primer sequence

<400> SEQUENCE: 14
gcggtggagg agaacacgct                                              20

<210> SEQ ID NO 15
<211> LENGTH: 21
<212> TYPE: DNA
<213> ORGANISM: Artificial Sequence
<220> FEATURE:
<223> OTHER INFORMATION: Synthetic primer sequence

<400> SEQUENCE: 15
tctccgcctt gattccatcc a                                            21

<210> SEQ ID NO 16
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 16
ggcagcaaag gcaatgttga ggga                                         24

<210> SEQ ID NO 17
<211> LENGTH: 26
<212> TYPE: DNA
<213> ORGANISM: Artificial Sequence
<220> FEATURE:
<223> OTHER INFORMATION: Synthetic primer sequence

<400> SEQUENCE: 17
tgggaacatg tgccaagatg agatga                                       26

<210> SEQ ID NO 18
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 18
ggcggtctct agtagcgcat gt                                           22

<210> SEQ ID NO 19
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 19
tggttgagga aagccgagtc ca                                           22

<210> SEQ ID NO 20
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 20
```
accaacaatc acagccacag                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 21
tgctcttccc aagtccatct                                                20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 22
gctggcagga agaagtttcg                                                20

<210> SEQ ID NO 23
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 23
gagttggagg aagcagggat ag                                             22

<210> SEQ ID NO 24
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 24
attgctgctg gaaactatcc tgag                                           24

<210> SEQ ID NO 25
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 25
ggtccaatac ggtgtctctg agta                                           24

<210> SEQ ID NO 26
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 26
cgatgtgtga tctcctatgg tc                                             22

<210> SEQ ID NO 27
<211> LENGTH: 22
<212> TYPE: DNA
<213> ORGANISM: Artificial Sequence

```
<220> FEATURE:
<223> OTHER INFORMATION: Synthetic primer sequence

<400> SEQUENCE: 27
aagctgatgg gctctagaaa tc                                              22

<210> SEQ ID NO 28
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 28
ggcgacctcg tattgggaat cc                                              22

<210> SEQ ID NO 29
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 29
aagttcgaca gcgtctcgga cc                                              22

<210> SEQ ID NO 30
<211> LENGTH: 1476
<212> TYPE: DNA
<213> ORGANISM: Solanum lycopersicum

<400> SEQUENCE: 30
atgggcggag gaggatcagt gaaggaagtt caatcgaagg cggagcttga taagattgtc      60
gccgacggat caccggcgat tttgcacttt tgggcatcat ggtgtgaagc ttctaagcac     120
atggaccaag tcttttcgca tcttttctact gatttcccac atgcccattt tctaagagtt    180
gaagctgaag aacagcctga gatatctgag ctgcactctg tttctgctgt accttacttt    240
gtcttcttca aggaagggaa agctgttgat acattggaag gggccgatcc atctagtttg    300
gctaacaagg ttgcaaaaat tgctgggtca atcactcctg ggatcctgc cgtcctgct     360 agcctaggaa tggctgcagg tccctctgtt cttgaagcaa ttcaggagtt gtctagagaa    420
aacggtgccc ctcaagtgtc aagttctggt cttgatgatc ggctaacaaa gcgacttcag    480
cagctggttt cttctcatcc agtattgctt ttcatgaaag ggaccccaga agaacccaag    540
tgtggtttta gtcagaaagt cgttgatatc ttgaagaaag agaaggtcaa atttggaagt    600
tttgatattc tgatggacag tgaggtccgt gagggtctga agaaattttc caattggcca    660
acatatcctc aactgtactg caagggtgaa cttcttggtg ttgtgatat tgttataact    720 atgcatgaga gtggtgaact tacagatgtt ttcaaggatc acggggttgg ggtctctgat    780
tctcttgaaa ctaaaccgaa taaaactgcg ggtgggaagg tggcatctc tgaacaatct    840 ggcttgagta ctgccttgac tactcgtctt gcaggtctga taaactctag cccagttatg    900
ctgtttatga aggaacagt tgatgaaccc cggtgtggat tcagcagaaa ggtggtggat    960
attctcaaac aggagaaagt ggagtttgag actttgaca ttctttctga tgatgaagtc   1020
cgtcaaggac tgaaagttta ttccaactgg tctagttatc cacagctgta cataaagggt   1080
gaacttattg gtggatcaga cattgtactg gagatgcaaa agagcggtga gtttaggaag   1140
gttctgactg agaaggggat acaccagaaa gttagtcttg aagaccgttt aaagaatcta   1200
```

```
ctgaattcct cacctgtaat gctcttcatg aagggtacac cagattctcc aagatgtggt    1260
ttcagctcca aggtggtaaa tgccttgaag gaggaagggg ttgattttgg atcctttgat    1320
attctatccg acgaagaagt aaggcaggga ctgaagacct tctctaactg gccaacttat    1380
ccgcagctgt attacaaagg cgaacttgta ggaggatgtg atatcgtgct ggaattacat    1440
agcgggggtg aattgaagtc aacattatct gaatag                              1476
```

<210> SEQ ID NO 31
<211> LENGTH: 491
<212> TYPE: PRT
<213> ORGANISM: Solanum lycopersicum

<400> SEQUENCE: 31

```
Met Gly Gly Gly Ser Val Lys Glu Val Gln Ser Lys Ala Glu Leu
1               5                   10                  15

Asp Lys Ile Val Ala Asp Gly Ser Pro Ala Ile Leu His Phe Trp Ala
            20                  25                  30

Ser Trp Cys Glu Ala Ser Lys His Met Asp Gln Val Phe Ser His Leu
        35                  40                  45

Ser Thr Asp Phe Pro His Ala His Phe Leu Arg Val Glu Ala Glu Glu
    50                  55                  60

Gln Pro Glu Ile Ser Glu Leu His Ser Val Ser Ala Val Pro Tyr Phe
65                  70                  75                  80

Val Phe Phe Lys Glu Gly Lys Ala Val Asp Thr Leu Glu Gly Ala Asp
                85                  90                  95

Pro Ser Ser Leu Ala Asn Lys Val Ala Lys Ile Ala Gly Ser Ile Thr
            100                 105                 110

Pro Gly Asp Pro Ala Ala Pro Ala Ser Leu Gly Met Ala Ala Gly Pro
        115                 120                 125

Ser Val Leu Glu Ala Ile Gln Glu Leu Ser Arg Glu Asn Gly Ala Pro
    130                 135                 140

Gln Val Ser Ser Ser Gly Leu Asp Asp Arg Leu Thr Lys Arg Leu Gln
145                 150                 155                 160

Gln Leu Val Ser Ser His Pro Val Leu Leu Phe Met Lys Gly Thr Pro
                165                 170                 175

Glu Glu Pro Lys Cys Gly Phe Ser Gln Lys Val Val Asp Ile Leu Lys
            180                 185                 190

Lys Glu Lys Val Lys Phe Gly Ser Phe Asp Ile Leu Met Asp Ser Glu
        195                 200                 205

Val Arg Glu Gly Leu Lys Lys Phe Ser Asn Trp Pro Thr Tyr Pro Gln
    210                 215                 220

Leu Tyr Cys Lys Gly Glu Leu Leu Gly Gly Cys Asp Ile Val Ile Thr
225                 230                 235                 240

Met His Glu Ser Gly Glu Leu Thr Asp Val Phe Lys Asp His Gly Val
                245                 250                 255

Gly Val Ser Asp Ser Leu Glu Thr Lys Pro Asn Lys Thr Ala Gly Gly
            260                 265                 270

Lys Gly Gly Ile Ser Glu Gln Ser Gly Leu Ser Thr Ala Leu Thr Thr
        275                 280                 285

Arg Leu Ala Gly Leu Ile Asn Ser Ser Pro Val Met Leu Phe Met Lys
    290                 295                 300

Gly Thr Val Asp Glu Pro Arg Cys Gly Phe Ser Arg Lys Val Val Asp
305                 310                 315                 320

Ile Leu Lys Gln Glu Lys Val Glu Phe Glu Thr Phe Asp Ile Leu Ser
```

-continued

```
                    325                 330                 335
Asp Asp Glu Val Arg Gln Gly Leu Lys Val Tyr Ser Asn Trp Ser Ser
            340                 345                 350

Tyr Pro Gln Leu Tyr Ile Lys Gly Glu Leu Ile Gly Gly Ser Asp Ile
        355                 360                 365

Val Leu Glu Met Gln Lys Ser Gly Glu Phe Arg Lys Val Leu Thr Glu
    370                 375                 380

Lys Gly Ile His Gln Lys Val Ser Leu Glu Asp Arg Leu Lys Asn Leu
385                 390                 395                 400

Leu Asn Ser Ser Pro Val Met Leu Phe Met Lys Gly Thr Pro Asp Ser
            405                 410                 415

Pro Arg Cys Gly Phe Ser Ser Lys Val Val Asn Ala Leu Lys Glu Glu
            420                 425                 430

Gly Val Asp Phe Gly Ser Phe Asp Ile Leu Ser Asp Glu Glu Val Arg
            435                 440                 445

Gln Gly Leu Lys Thr Phe Ser Asn Trp Pro Thr Tyr Pro Gln Leu Tyr
    450                 455                 460

Tyr Lys Gly Glu Leu Val Gly Gly Cys Asp Ile Val Leu Glu Leu His
465                 470                 475                 480

Ser Gly Gly Glu Leu Lys Ser Thr Leu Ser Glu
            485                 490
```

PLANTS WITH ENHANCED TOLERANCE TO MULTIPLE ABIOTIC STRESSES

CROSS-REFERENCE TO RELATED APPLICATIONS

The present application is a divisional of U.S. patent application Ser. No. 14/241,992, filed Feb. 28, 2014, which is the National Stage of PCT/US2012/053404, filed Aug. 31, 2012, which claims the priority benefit of U.S. Provisional Patent Application Ser. No. 61/529,404, filed Aug. 31, 2011, entitled Development of an *Arabidopsis* Monothiol Glutaredoxin AtGRXS17-Mediated Thermotolerance in Plants. Each of the foregoing applications is incorporated by reference in its entirety herein.

SEQUENCE LISTING

The nucleic and amino acid sequences listed in the accompanying Sequence Listing are presented in accordance with 37 C.F.R. 1.822. Only one strand of each nucleic acid sequence is shown, but the complementary strand is understood as included by any reference to the displayed strand. The Sequence Listing is submitted as an ASCII computer readable text file, created on Aug. 24, 2012, 35 KB, which is incorporated by reference herein. In the accompanying sequence listing: SEQ ID NO: 1 is a coding complementary (cDNA) sequence of the mRNA for the AtGRXS17 gene; SEQ ID NO:2 is the amino acid sequence of AtGRXS17; SEQ ID NO:3 is the nucleotide sequences of the AtGRXS17-GFP fusion protein; SEQ ID NO:4 is the amino acid sequence of the fusion protein; SEQ ID NO:5 is a coding cDNA sequence of the OsGRXS17 gene; SEQ ID NO:6 is the amino acid sequence of OsGRXS17; SEQ ID NO: 7 is the complete coding sequence of chromosome 10 of *Oryza sativa*, where residues 1295-1688 correspond to the sequence used for RNAi; SEQ ID NOs:8-29 are nucleotide sequences of primers; SEQ ID NO:30 is the coding sequence of the SlGRXS17 gene; and SEQ ID NO:31 is the amino acid sequence of SlGRXS17.

BACKGROUND OF THE INVENTION

Field of the Invention

The present invention relates to genetically-modified plants having enhanced tolerance to multiple abiotic stressors.

Description of Related Art

Abiotic stress (drought, cold, heat, salt, etc.) adversely affects the growth and development of plants and limits agricultural productivity, often causing losses of billions of dollars per year. Worldwide extensive agricultural losses are attributed to temperature stress and drought. Drought stress alone afflicts more than 50% of the Earth's surface area. Furthermore, drought and heat stress often occur simultaneously, and both are tightly related to oxidative stress.

While various signaling networks regulate plant responses to stress, the mechanisms unifying these diverse biological processes are largely unknown. A common plant response to drought or cold as well as heat stresses involves dramatic increases in the production of reactive oxygen species (ROS). Although ROS can act as signals for stress responses, excessive ROS production causes oxidative damage to macromolecules and cell structures, leading to inhibition of plant development. Therefore, the level of ROS must be regulated in plants through the coordination of ROS production, signaling and scavenging. Heat stress is known to induce oxidative stress. Furthermore, during prolonged heat stress, ROS levels increase dramatically, resulting in significant oxidative damage to plant macromolecules and cell structures. Thus, toxic ROS must be rapidly detoxified by various cellular enzymatic or nonenzymatic mechanisms. In particular, $H_2O_2$ has been known to block heat shock response and macromolecule refolding activity under heat stress, for example, thereby leading to insufficient macromolecule biosynthesis quality control and enhanced endoplasmic reticulum (ER) stress. Uncontrolled stress responses may enhance cell death. Protection against oxidative stress, therefore, is an important component in determining the survival of a plant under stress.

The phytohormone abscisic acid (ABA) is a key mediator of drought stress and coordinates a complex regulatory network enabling plants to cope with decreased water availability by regulation of downstream signaling pathways, including the transcription factor AREB (ABA-responsive element binding protein). Cold stress also adversely affects plant crop productivity. Plants have evolved sophisticated response pathways that include the CBF (C-repeat binding factor) pathway, which contributes to chilling resistance and cold acclimation. Tomato, in particular, has poor freezing tolerance and suffers chilling injury when exposed to low temperatures.

Glutaredoxins are small ubiquitous proteins of the thioredoxin family and mediate reversible reduction of disulfide bonds of substrate proteins in the presence of glutathione (GSH) via a dithiol or monothiol mechanism. These enzymes have emerged as key regulators in diverse cellular processes, including oxidative stress responses. Glutaredoxins and thioredoxins function by regulating cellular redox state and redox-dependent signaling pathways and are conserved in both prokaryotes and eukaryotes. In plants, glutaredoxins represent a large protein family, the members of which are not only necessary for redox buffering, but also play roles in heavy metal detoxification, plant development, plant-pathogen interactions, iron homeostasis, and abiotic stress response. All glutaredoxins have a CXXC/S active site motif where the cysteines can be used in the reduction reaction via a dithiol (using the two cysteines) or monothiol (involving only the N-terminal cysteine) mechanism. Plant glutaredoxins are divided into three classes: namely the CPYC, CGFS, and CC-type classes. The CPYC and CGFS classes exist in all examined organisms from prokaryotes to eukaryotes. Glutaredoxins from the CGFS class all contain the strictly conserved CGFS motif. A single glutaredoxin protein can have multiple functions in plants.

SUMMARY OF THE INVENTION

The present disclosure is broadly concerned with a genetically-modified plant having enhanced tolerance to an abiotic stressor as compared to a control plant. The genetically-modified (or engineered) plant has ectopic expression of a heterologous, abiotic stress tolerance gene, which encodes for a glutaredoxin.

Embodiments described herein are also directed towards methods of enhancing the tolerance of a plant to an abiotic stressor. The methods comprise transforming the plant with a heterologous, abiotic stress tolerance gene, wherein the gene encodes a glutaredoxin, thereby enhancing the tolerance of the plant to an abiotic stressor.

Methods of producing genetically-modified plants having enhanced tolerance to an abiotic stressor are also provided. The methods comprise crossing a first plant with a second plant to thereby produce progeny, wherein at least one of the first or second plants is a genetically-modified plant having ectopic expression of a heterologous, abiotic stress tolerance gene. Advantageously, the progeny have enhanced tolerance to an abiotic stressor.

Genetically-modified seeds produced according to the various methods described herein are also provided. In some embodiments, a method of producing genetically-modified seed is provided, which comprises providing a genetically-modified plant having ectopic expression of a heterologous, abiotic stress tolerance gene, and self-pollinating the plant to thereby produce genetically-modified seed. The genetically-modified seed comprises the heterologous, abiotic stress tolerance gene.

Recombinant plant cells are also provided. The plant cells have ectopic expression of a heterologous glutaredoxin by stable transformation with a nucleic acid construct encoding the glutaredoxin, wherein the glutaredoxin is GRXS17.

An isolated nucleotide sequence encoding a fusion protein for enhancing the abiotic stress tolerance of a plant is also provided. The isolated nucleotide sequence comprises: (a) a sense or antisense sequence corresponding to SEQ ID NO:3, or the conservatively modified variants thereof; or (b) a nucleotide sequence encoding a protein comprising SEQ ID NO:4, or a protein having at least about 50% sequence identify to SEQ ID NO:4 and retaining the functional characteristics thereof.

The disclosure is also concerned with fusion proteins for enhancing the abiotic stress tolerance of a plant. The fusion protein comprises a glutaredoxin amino acid sequence linked to a reporter amino acid sequence by one or more peptide bonds.

In some embodiments, a genetically-modified plant having enhanced resistance to an abiotic stressor (particularly drought stress) is also provided, which has inhibited expression, activity, or function of an endogenous glutaredoxin gene.

BRIEF DESCRIPTION OF THE DRAWINGS

FIG. 5 is a table of PCR primers used in the Examples;

FIG. 6 shows images of the subcellular localization of AtGRXS17. Transient expression of (A) free GFP and (B) GFP-AtGRXS17 in tobacco cells after being treated at 25° C. and 45° C. for 90 min. Scale bars=25 μm. The arrows highlight the nucleus;

FIG. 13 shows graphs of (A) Chlorophyll fluorescence of wild type and AtGRXS17-expressing plants; and (B) Electrolyte leakage of wild type and AtGRXS17-expressing plants after heat stress;

FIG. 24 is graph of the relative water content (RWC) calculated the day when wilting of OsGRXS17-silenced rice appeared under drought stress treatment. RWC (%)=[(FM−DM)/(TM−DM)]*100. FM=Fresh Mass, DM=Dry Mass, TM=Turgid Mass;

FIG. 25 is a table of PCR primers used in the Examples;

FIG. 30 shows graphs of (A) Electrolyte leakage of AtCBF3-, AtGRXS17-expressing and wild-type tomato plants during cold treatment; and (B) Chlorophyll fluorescence of the bottom second leaves of wild type, AtCBF3-, AtGRXS17-expressing tomato plants during cold treatment. The error bars indicates ±SD (n=3);

DETAILED DESCRIPTION

Figure 1:
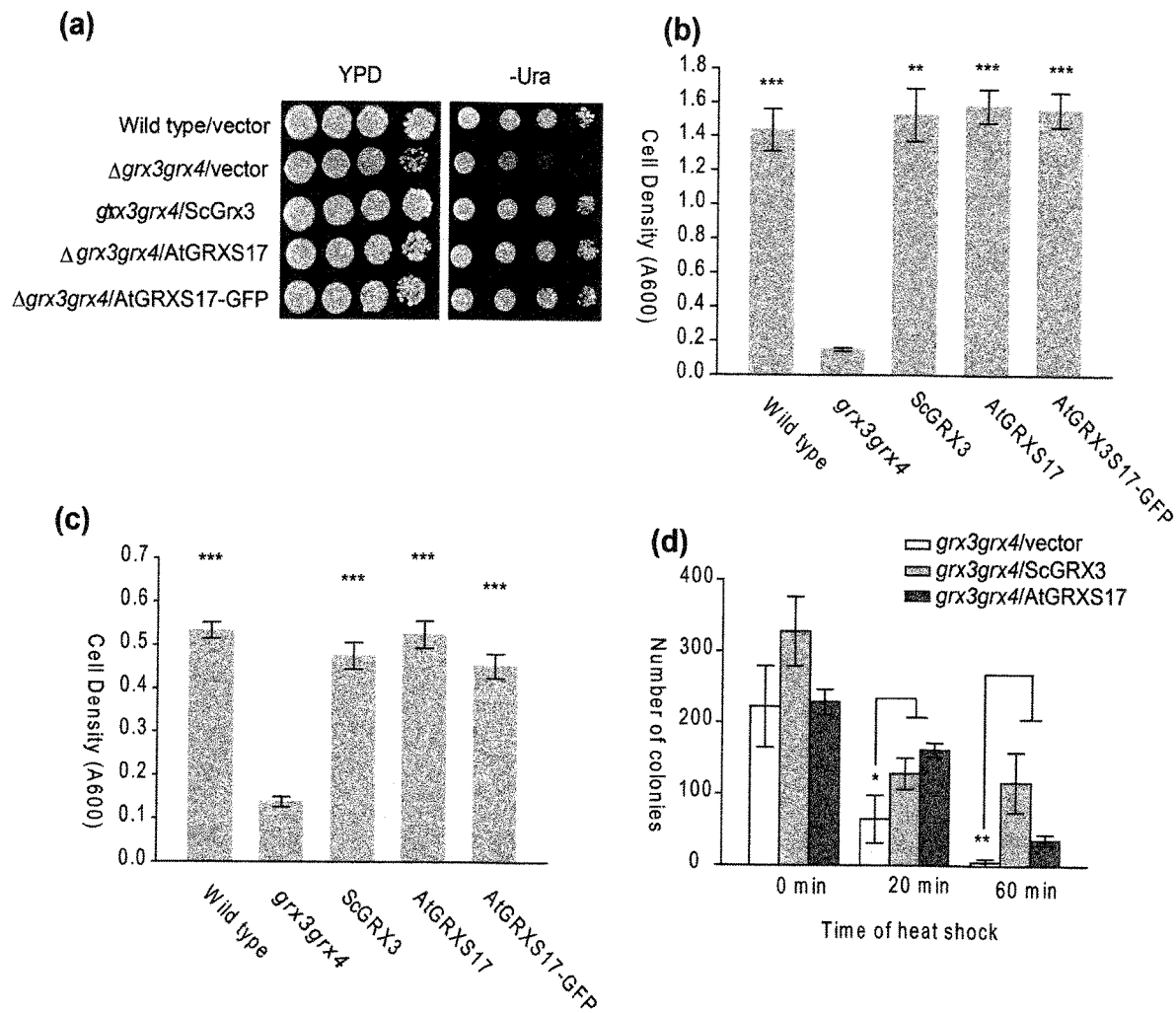
FIG. 1 shows (A) data that AtGRXS17 rescues the cell growth of yeast Grx3/Grx4 mutant. Vector-expressing wild type cells and vector-, yeast Grx3-, AtGRXS17-, and AtGRXS17-GFP-expressing grx3grx4 cells were grown on YPD and SC-Ura media. The photographs were taken after 3 days of growth at 30° C.; (B) Yeast strains carrying various plasmid DNAs as indicated in Example 1 were grown in SC-Ura liquid media with 1 mM $H_2O_2$; (C) Yeast strains carrying various plasmid DNAs as indicated in Example 1 were grown in SC-Ura liquid media 0.5 mM Diamide; (D) data showing that AtGRXS17 suppresses the sensitivity of yeast Grx3/Grx4 mutants to heat shock.

In more detail, the present invention is concerned with plants having ectopic expression of an exogenous, abiotic stress tolerance gene, which thereby have increased tolerance or resistance to abiotic stresses relative to a control plant. Unless otherwise indicated by the context, references herein to a "plant" or "plants" includes tissues, organs, or parts thereof (e.g., leaves, stems, tubers), fruit, or cells thereof. The invention is also concerned with various methods of increasing plant tolerance or resistance to abiotic stresses by ectopic expression of an exogenous, abiotic stress tolerance gene in a plant. Methods of creating such non-naturally occurring genetically-modified plants are also provided, along with nucleic acid constructs, vectors, and fusion proteins useful in such methods. The invention is suitable for use with various plants, including both monocotyledons (i.e., plants having one cotyledon (seed-leaf), aka "monocots") and dicotyledons (i.e., plants having two cotyledons, aka "dicots"). Non-limiting examples of plants suitable for the disclosed embodiments include grains (e.g., wheat, oat, barley, rice, maize, millet, rye, sorghum, triticale, buckwheat, quinoa), legumes (e.g., soybeans, beans, peas, alfalfa), tubers (e.g., potatoes, sweet potatoes, cassava, yam), nightshades (e.g., tomatoes, peppers, tobacco), other cash crops (e.g., cotton), and the like.

The inventive methods can be used to produce plants with enhanced tolerance to a variety of abiotic stresses. The term "abiotic" stress is used herein to refer to non-living chemical and/or physical factors in the environment that affect plant growth and/or development. Examples include extreme temperatures (heat or cold), water availability (e.g., drought), salinity (e.g., salt), and the like. Such abiotic factors are considered "stressors" when they influence the environment beyond its normal range of variation to adversely affect plant growth and/or development. For example, heat or cold stress may occur when the plant is subjected to temperatures at least about 10-20° C. higher or lower than the normal plant growing temperatures. "Normal plant growing temperatures" refers to temperature ranges suggested for optimal growth and yield, which for most species are known in the art. For example, many plants prefer a daytime temperature of between about 24° C. and about 28° C., and a nighttime temperature of between about 19° C. and about 21° C. In general, preferred nighttime temperatures are about 5° C. to 7° C. lower than daytime temperatures. The tolerance of the transgenic plant is considered to be "enhanced" when the transgenic plant's growth or development is superior to the growth and development of a control plant under the same conditions or stressors, even if the transgenic plant is not completely resistant to or unaffected by the stressor.

As noted above, the transgenic plants have ectopic expression of an exogenous gene. The term "exogenous" is used herein to refer to a nucleic acid sequence (e.g., DNA, RNA) or gene that originates from a source outside of a particular plant species, and is introduced into another (host) plant species to create the transgenic plant. For example, the term as it is used in reference to expression of an encoding nucleic acid, refers to introduction of the encoding nucleic acid in an expressible form into the host plant. Transformation techniques for plants are well known in the art and include *Agrobacterium*-mediated techniques, as described herein, as well as other techniques involving the uptake of exogenous genetic material by the plant, such as PEG- or electroporation-mediated uptake, particle bombardment-mediated delivery, and/or microinjection.

In one or more embodiments, the exogenous abiotic stress tolerance gene is heterologous. The term "heterologous" refers to genetic material derived from a source other than (i.e., foreign to) the referenced species, whereas "homologous" refers to genetic material derived from, naturally associated with, or native to, the host plant species. For example, in some embodiments, the transgenic plants are created by introducing genetic material encoding for an abiotic stress tolerance gene product from one species into a host plant of a different species, wherein the host plant expresses that heterologous gene product. Advantageously, ectopic expression or overexpression of the heterologous abiotic stress tolerance gene increases the tolerance or resistance of the transgenic plant to abiotic stresses.

The abiotic stress tolerance gene described herein is a glutaredoxin gene (aka glutaredoxin transgene), and more preferably a gene encoding a CGFS-type monothiol glutaredoxin, preferably GRXS17, which is highly conserved across different species. More particularly, transgenic plants according to the invention preferably express a heterologous gene for this glutaredoxin. In some embodiments, the gene is expressed in the presence of the abiotic stress and/or is dependent on the plant being under stress for expression to be activated. In other embodiments, expression is not dependent on the presence or absence of a stressor. In some embodiments, *Arabidopsis* gene AtGRXS17 can be used to transform plant species other than *Arabidopsis*, such as tomatoes, rice, wheat, etc. into stress tolerant transgenic plants. Likewise, tomato gene SlGRXS17 can be used to transform other plant species such as rice, wheat, corn, etc. into stress tolerant transgenic plants, while rice gene OsGRXS17 can be used to transform other plant species such as tomatoes, wheat, corn, etc. into stress tolerant transgenic plants.

In some embodiments, the tolerance to an abiotic stressor in the plant is enhanced by expressing in the plant an abiotic stress tolerance gene which comprises (or consists of) a sequence selected from the group consisting of: (a) a nucleotide sequence comprising SEQ ID NO:1, 3, 5, or 30; (b) a nucleotide sequence comprising an antisense sequence corresponding to SEQ ID NO:1, 3, 5, or 30; (c) a nucleotide sequence having at least about 70% sequence identity (preferably at least about 80% sequence identity, and more preferably at least about 90% sequence identity) to SEQ ID NO: 1, 3, 5, or 30 (i.e., conservatively modified variants thereof); (d) a nucleotide sequence encoding a glutaredoxin protein comprising SEQ ID NO:2, 4, 6, or 31; and (e) a nucleotide sequence encoding a glutaredoxin protein having at least about 50% amino acid identity (preferably at least about 70% amino acid identity, and more preferably at least about 80% amino acid identity) to SEQ ID NO: 2, 4, 6, or 31 and retaining the functional characteristics thereof. The "functional characteristics" of the abiotic stress tolerance proteins refers to the ability of the expressed protein or enzyme to regulate endogenous stress response pathways and/or the enzymatic function of reactive oxygen species, protect the plant from oxidative stress, and enhance endogenous antioxidant activity. In some embodiments, the plant abiotic stress tolerance protein is an antioxidant for reactive oxygen species, such as $.O_2^-$, $H_2O_2$, and/or —OH radicals.

In some embodiments, the abiotic stress tolerance protein upregulates endogenous heat shock proteins in the plant. In some embodiments, the abiotic stress tolerance protein upregulates catalase enzyme activity in the plant. Thus, "conserved variants" of the disclosed nucleic acid and amino acid sequences are contemplated herein, as long as the resulting proteins or enzymes retain one or more of the abilities described above.

In one or more embodiments, the method of enhancing the tolerance of a plant to abiotic stress comprises introducing and expressing in a plant cell a heterologous nucleic acid construct encoding a glutaredoxin, preferably a CGFS-type monothiol glutaredoxin, and more preferably GRXS17. A recombinant plant cell comprising the nucleic acid construct, preferably stably incorporated into its genome, is also provided herein. The nucleic acid construct can comprise a nucleic acid coding sequence which is operably linked to a promoter that drives expression in the plant cell. Suitable promoters include the cauliflower mosaic virus promoter (CaMV35S), the rice actin promoter, the maize ubiquitin promoter, or other stress-inducible promoters that can be selected by those of ordinary skill in the art. A "stress-inducible promoter" is one that is activated in response to stress. More preferably, the transgenic plant is prepared by introducing into a plant cell a vector or plasmid comprising the nucleic acid construct. Thus, in one or more embodiments, a plant cell transformed with an expression vector or plasmid described herein is also provided. In further embodiments, a vector or plasmid is provided for preparing a transgenic plant having enhanced resistance to abiotic stress. The vector or plasmid comprises an expression cassette comprising a nucleic acid construct, which encodes an abiotic stress tolerance gene, operably linked a suitable promoter for driving expression of the nucleic acid in the plant cell.

In some embodiments, the nucleic acid construct comprises (or consists of) a sequence selected from the group consisting of: (a) a nucleotide sequence comprising SEQ ID NO:1, 3, 5, or 30; (b) a nucleotide sequence comprising an antisense sequence corresponding to SEQ ID NO: 1, 3, 5, or 30; (c) a nucleotide sequence having at least about 70% sequence identity (preferably at least about 80% sequence identity, and more preferably at least about 90% sequence identity) to SEQ ID NO: 1, 3, 5, or 30 (i.e., conservatively modified variants thereof); (d) a nucleotide sequence encoding a glutaredoxin protein comprising SEQ ID NO:2, 4, 6, or 31; and (e) a nucleotide sequence encoding a glutaredoxin protein having at least about 50% amino acid identity (preferably at least about 70% amino acid identity, and more preferably at least about 80% amino acid identity) to SEQ ID NO: 2, 4, 6, or 31 and retaining the functional characteristics thereof.

In some embodiments, there is provided an isolated nucleotide sequence encoding a glutaredoxin protein for enhancing abiotic stress tolerance in plants. In some embodiments, the nucleotide sequence comprises a sense or antisense sequence corresponding to SEQ ID NO: 1, 5, or 30 or the conservatively modified variants thereof. In some embodiments, the nucleotide sequence encodes a protein comprising SEQ ID NO:2, 6, or 31 or a protein having at least about 50% amino acid identity (preferably at least about 70% amino acid identity, and more preferably at least about 80% amino acid identity) to SEQ ID NO:2, 6, or 31 and retaining the functional characteristics thereof.

In some embodiments, there is provided an isolated nucleotide sequence encoding a fusion protein for enhancing the abiotic stress tolerance of a plant. In some embodiments, the nucleotide sequence comprises a sense or antisense sequence corresponding to SEQ ID NO:3, or the conservatively modified variants thereof. In some embodiments, the nucleotide sequence encodes a protein comprising SEQ ID NO:4, or a protein having at least about 50% amino acid identity (preferably at least about 70% amino acid identity, and more preferably at least about 80% amino acid identity) to SEQ ID NO:4 and retaining the functional characteristics thereof. Thus, in one or more embodiments, a fusion protein for enhancing the abiotic stress tolerance of a plant is provided. In some embodiments, the fusion protein comprises a glutaredoxin amino acid sequence, such as those described herein (e.g., 2, 4, 6, or 31), linked to reporter amino acid sequence by one or more peptide bonds. In some embodiments, the reporter is a fluorescent protein, such as green fluorescent protein (GFP). Other suitable reporters include beta-glucuronidase (GUS), luciferase, dsRed (red fluorescent protein), and the like.

Methods of the invention include, culturing plant tissue (e.g., leaf, cotyledon, or hypocotyl explants) on a suitable media (e.g., Murashige and Skoog (MS), or Chu ($N_6$)), followed by introduction of the exogenous abiotic stress tolerance gene into the tissue using suitable techniques, such as those described above and in the working examples. The abiotic stress tolerance gene can be introduced using a construct, vector, plasmid or other suitable technique. Expression of the gene results in transformed or modified tissue. As noted above, reporter genes can be used to verify transformation. The transformed tissue can then be used to regenerate transgenic whole plants having enhanced tolerance to abiotic stressors. Transgenic plants can be regenerated using various techniques depending upon the plant species involved. In one or more embodiments, regeneration comprises inducing callus formation from the transformed tissue, and regeneration of shoots, followed by rooting of the shoots in soil or other appropriate rooting media to generate the whole plant.

The resulting transgenic plants can be crossed to prepare progeny, and preferably homozygous progeny or seeds. Thus, abiotic stress-tolerant plants can also be produced indirectly by breeding parent plants having enhanced abiotic stress tolerance with other abiotic stress-tolerant plants, or even with other cultivars having additional desired characteristics (e.g., pest or herbicide resistance, geographic adaptation, stalk strength, etc.). The resulting progeny can then be screened to identify abiotic stress-tolerant progeny.

In one or more embodiments, the invention is also concerned with a process of producing (transgenic) seed. In some embodiments, the method comprises self-pollination of a transgenic plant as described herein. In some embodiments, the method comprises crossing a first plant with a second plant, wherein at least one of the first or second plants is a transgenic plant having enhanced abiotic stress tolerance, as described herein. In some embodiments, the first and second plants are both transgenic plants as described herein. In one or more embodiments, the first and second plants can be crossed via cross-pollination using insects (e.g., flies in cloth cages), manual (hand) pollination, and the like.

Advantageously, transgenic plants according to the various embodiments of the invention have enhanced tolerance to abiotic stress. However, unlike many other transgenic plants with similar improvements in tolerance to one or more specific stresses, plants according to the invention have a phenotype/morphology that is otherwise substantially similar to, and in some cases, nearly identical to wild type plants of the same species (when such wild type plants are grown under non-stress conditions). In other words, the shape, size, and/or abundance of foliage and/or fruit/vegetable is substantially similar between the transgenic plants and wild type plants. Plants are considered to be "substantially similar" herein if those skilled in the art have difficulty visually distinguishing between the genetically-modified plant and the control plant when grown under identical normal growing conditions. In contrast, when grown under stress, transgenic plants according to the various embodiments of the invention, have significantly improved morphologies as compared to control plants grown under the same conditions. For example, the transgenic plant may have one or more of the following improved characteristics: vigorous growth, abundant foliage, longer primary roots, yield, height, and/or shoot water potential, when grown in the presence of one or more abiotic stressors. Similarly, the transgenic plants have significantly improved recovery after stress.

In one or more embodiments, the invention is also concerned with enhancing the abiotic stress tolerance of plants by silencing the expression of an endogenous glutaredoxin gene that is normally expressed in the plant. In some embodiments, the target gene encodes a CGFS-type monothiol glutaredoxin, and more preferably is GRXS17. The method comprises inhibiting the expression, activity, or function of an endogenous glutaredoxin gene in a plant to thereby produce a modified plant having enhanced resistance to an abiotic stress. It is noted that plants produced according to these methods are particularly resistant to drought. This method can be carried out in addition to, or in lieu of the ectopic expression of the abiotic stress tolerance gene described above.

It will be appreciated that the expression, activity, or function of an endogenous glutaredoxin gene in a plant can be inhibited by any suitable gene down-regulation technique, which can include modifying the target gene itself, as well as methods involving modification of adjacent sequences. For example, transgenic techniques can be used to alter expression of the target gene. In one aspect, the plant can comprise a nucleic acid construct, preferably stably incorporated into its genome, which inhibits expression, activity, or function of the endogenous glutaredoxin gene. Thus, the resulting plant is prepared by introducing into a plant cell a nucleic acid construct that inhibits expression, activity, or function of the target endogenous glutaredoxin gene. In some embodiments, the nucleic acid encodes a double-stranded RNA that inhibits expression, activity, or function of the endogenous glutaredoxin gene. The nucleic acid can be introduced in a construct, vector, or plasmid including applicable promoters using any suitable method, as described herein.

In some embodiments, RNA interference (RNAi) is used to inhibit the expression, activity, or function of the target gene. More specifically, RNAi is used to reduce the expression of one or more transcripts of the endogenous glutaredoxin gene. RNAi relies on sequence-specific, post-transcriptional gene silencing, and is broadly defined herein to include all post-transcriptional and transcriptional mechanisms of RNA-mediated inhibition of gene expression. Generally, in RNAi, all or a portion of the target gene (typically greater than 200 bp) is duplicated in an expression vector in a sense/antisense or an antisense/sense orientation so that the resulting mRNA hybridizes to itself forming a large hairpin loop. This product in then processed by the cell into small interfering RNAs (siRNAs) which are approximately 21-24 nucleotides in length triggering RNAi and silencing the endogenous target gene. RNAi can be used to either partially or completely inhibit expression of the target gene. RNAi may also be considered to completely or partially inhibit the function of a target RNA. Thus, in one aspect, the nucleic acid construct preferably comprises a sense and/or an antisense sequence for the target endogenous glutaredoxin gene and encodes double stranded RNA that inhibits the expression, activity, or function of the target endogenous glutaredoxin gene. In a further aspect, the nucleic acid construct will preferably comprise a sense sequence operably linked to its complementary antisense sequence and encoding double stranded RNA that inhibits expression, activity, or function of the target endogenous glutaredoxin gene.

Virus-induced gene silencing (VIGS) can also be used to inhibit the expression, activity, or function of the target endogenous glutaredoxin gene. This technology uses plant viruses to express a small fragment of a host gene in the form of dsRNA in inoculated plants. The replication of the viral vector, which includes the target gene fragment, induces a host response that knocks down or inhibits expression of the endogenous glutaredoxin gene. In these embodiments, the plant is inoculated with a viral vector comprising a sequence (sense or antisense) of the targeted endogenous glutaredoxin gene, which encodes for RNA that inhibits the expression, activity, or function of the target gene to thereby produce the transgenic plant.

It will be appreciated that other known transgenic methods can also be utilized to silence the target gene, including microRNAs, artificial microRNAs, antisense RNA, or T-DNA insertional inactivation of the target gene or associated promoter. Mutagenesis (e.g., insertions, deletions, and/or point mutations) of the target gene can also be used to disrupt gene function.

Advantageously, plants with a silenced endogenous glutaredoxin gene have a phenotype/morphology that is otherwise substantially similar to, and in some cases, nearly identical to wild type plants of the same species (when such wild type plants are grown under non-stress conditions). In other words, the shape, size, and/or abundance of foliage and/or fruit/vegetable is substantially similar between the genetically-modified plants and wild type plants. In contrast, when grown under stress, silenced plants, have significantly improved morphologies as compared to control plants grown under the same conditions. In some embodiments, the silenced plants have significantly improved drought tolerance.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

A "control" plant, as used in the present invention, refers to a plant used to compare against transgenic or genetically modified plants according to the invention for the purpose of identifying changes in the transgenic or genetically modified plant. The control plant is of the same species as the non-naturally occurring plant. In some cases, the control plant may be a wild type (native) plant, although cultivars and genetically altered plants that otherwise have normal expression of glutaredoxin and/or abiotic stress tolerance can also be used a references for comparison. A "wild type" plant is a plant that has not been genetically modified or treated in an experimental sense. A "wild-type" gene is one that has the characteristics of a gene isolated from a naturally occurring source. A "wild-type" gene product is one that has the characteristics of a gene product isolated from a naturally occurring source, whereas "modified" genes or gene products are those having modifications in sequence and/or functional properties (i.e., altered characteristics) when compared to the wild-type gene or gene product. Likewise, "genetically-modified" cells, tissues, seeds, plants etc. are those that have been altered to include a transgene and/or to change the expression, activity, or function of the target genes or gene products, as opposed to non-modified cells, tissues, etc. The term is synonymous with "genetically-engineered."

The term gene "expression" is used herein to refer to the process of converting genetic information encoded in a gene into RNA (e.g., mRNA, rRNA, tRNA, or snRNA) through transcription of the gene (i.e., via the enzymatic action of an RNA polymerase), and into protein, through translation of mRNA. Gene expression can be regulated at many stages in the process. The term "overexpression" refers to the production of a gene product in transgenic plants that exceeds levels of production in normal, control, or non-transgenic plants. References to altered "levels" of expression refers to the production of gene product(s) in modified plants, such as transgenic plants, in amounts or proportions that differ from that of normal, control, or non-modified plants.

The "inhibition," "silencing," or "knock down" of the expression, activity, or function of a gene, as used herein, is intended to refer to any suitable method of reducing or even completely suppressing protein expression from a gene or a coding sequence, including methods of reducing the levels of protein produced as a result of gene transcription to mRNA and subsequent translation of the mRNA.

References herein to "genes" encompass both the partial (fragment) or complete coding sequence of a gene (including its cDNA sequence), its complement, and its 5' or 3' untranslated regions.

The term "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced The term "vector" refers to nucleic acid molecules that transfer DNA segment(s) from one cell to another. The term includes recombinant DNA molecules containing a desired coding sequence(s) and appropriate nucleic acid sequences (e.g., promoters) necessary for the expression of the operably linked coding sequence in a particular host organism.

The term "transform" is used herein to refer to the introduction of foreign DNA into cells. Transformation may be accomplished by a variety of means known to the art and described herein.

A "sense" strand of nucleic acid construct refers to a strand that is transcribed by a cell in its natural state into a "sense" mRNA. The term "antisense" refers to a DNA sequence whose sequence of deoxyribonucleotide residues is complementary to all or part of the sequence of deoxyribonucleotide residues in a sense strand. Thus, an "antisense" sequence is a sequence having the same sequence as the non-coding strand in a DNA duplex. With respect to RNA, the term "antisense" refers to a RNA transcript that is complementary to all or part of a target primary transcript or mRNA and that blocks the expression of a target gene by interfering with the processing, transport and/or translation of its primary transcript or mRNA. The complementarity of an antisense RNA or DNA may be with any part of the specific gene or transcript, i.e., at the 5' non-coding sequence, 3' non-coding sequence, introns, or the coding sequence.

The term "isolated" when used in relation to a nucleic acid, refers to a nucleic acid sequence that is identified and separated from at least one contaminant nucleic acid with which it is ordinarily associated in its natural environment. That is, an isolated nucleic acid is one that is present in a form or setting that is different from that in which it is found in nature.

The terms "sequence identity" or "amino acid identity" are used herein to describe the sequence relationships between two or more nucleic acid or amino acid sequences when aligned for maximum correspondence over a specified comparison window. The percentage of "identity" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions. After alignment, the number of matched positions (i.e., positions where the identical nucleic acid base or amino acid residue occurs in both sequences) is determined and then divided by the total number of positions in the comparison window. This result is then multiplied by 100 to calculate the percentage of sequence or amino acid identity. It will be appreciated that a sequence having a certain % of sequence identity to a reference sequence does not necessarily have to have the same total number of nucleotides or amino acids (see e.g., microRNAs discussed above). Thus, a sequence having a certain level of "identity" includes sequences that correspond to only a portion (i.e., 5' non-coding regions, 3' non-coding regions, coding regions, etc.) of the reference sequence.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Protective Role of AtGRXS17 in Oxidative and Heat Stress Responses in Yeast

AtGRXS17 has a conserved Trx-HD and three tandem Grx-HDs, which are similar to yeast and mammalian monothiol Grxs, while yeast ScGrx3/ScGrx4 have one Grx-HD and a mammalian Grx3 has two repeated Grx-HDs at their C-termini. In yeast, ScGrx3 or ScGrx4 deletions do not affect cell growth; however, deletion of both ScGrx3 and ScGrx4 significantly reduce cell growth in either nutrient rich medium (YPD) or minimal medium (FIG. 1A). This impaired growth could be rescued by over-expression of either ScGrx3 or ScGrx4 (FIG. 1A). In order to examine if AtGRXS17 could complement yeast Grx3/Grx4 function in grx3grx4 double-mutant cells, AtGRXS17 and AtGRXS17-GFP (fusion protein with C-terminal green fluorescent protein) were expressed in the double mutant strain, respectively. Both AtGRXS17 and AtGRXS17-GFP could restore mutant cell growth (FIG. 1A).

Figure 2:
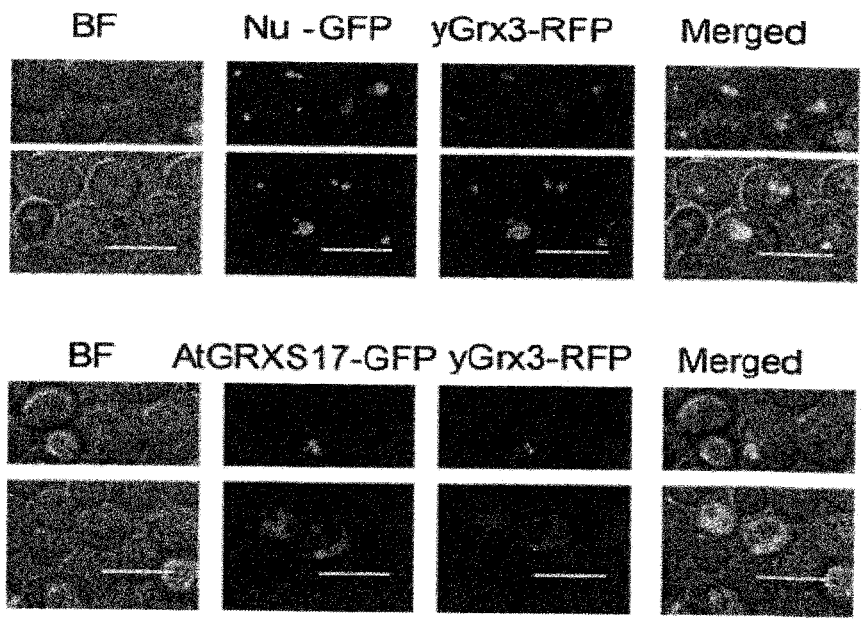
FIG. 2 contains images of co-localization of AtGRXS17-GFP and yeast Grx3-RFP with nuclear markers in yeast cells. BF: bright field. Scale bars=10 μm.

Yeast Grx3 and Grx4 are required for cell survival under oxidative stress. In order to determine if AtGRXS17 could suppress the sensitivity of grx3grx4 cells to external oxidants, both AtGRXS17 and AtGRXS17-GFP were expressed in grx3grx4-mutant cells and grown in the media with or without 1.5 mM $H_2O_2$ and 0.5 mM diamide. In these conditions, both AtGRXS17 and AtGRXS17-GFP, like yeast Grx3, was able to rescue the growth of mutant cells in the presence of $H_2O_2$ or diamide (FIGS. 1B and C). Moreover, AtGRXS17-GFP was shown to be co-localized with yeast Grx3-RFP in the nuclei when expressed in grx3grx4 cells (FIG. 2).

Given the conserved function of monothiol AtGRXS17 in counteracting oxidative stress in yeast (FIGS. 1B and C), we sought to determine if the effects of AtGRXS17 on temperature stress responses are also conserved in yeast. In comparison to normal yeast growth conditions (30° C.), grx3grx4 mutant yeast cells grown at 50° C. for 20 min displayed a reduced survival rates as measured by cell number, and grown at 50° C. for 60 min further limited growth (FIG. 1D), indicating that heat stress impairs the growth of grx3grx4 mutant yeast cells. When yeast Grx3 or AtGRXS17 were expressed in the mutant cells, the cells were more tolerant to the temperature stress (FIG. 1D), indicating AtGRXS17 may also play a crucial role in the protective effects against elevated temperatures. These data strongly suggest that a conserved temperature and oxidative response pathway is mediated by monothiol AtGRXS17.

Yeast Assays.

The full-length cDNA of AtGRXS17 was amplified by using an AtGRXS17 forward primer (SEQ ID NO:8) and an AtGRXS17 reverse primer (SEQ ID NO:9). The fidelity of all clones was confirmed by sequencing. In order to express AtGRXS17 in yeast cells, the AtGRXS17 was subcloned into yeast expression vector, piUGpd. *Saccharomyces cerevisiae* wild type strain CML235 (MATa ura3-52 leu2Δ1 his3Δ200) and double mutant grx3grx4 (MATa ura3-52 leu2Δ1 his3Δ200 grx3::kanMX4 grx4::kanMX4) were provided by Dr. Enrique Herrero (Universitat de Lleida, Lleida, Spain) and used in all yeast experiments. Yeast growth assays followed the published protocol (Cheng et al., AtGRXcp, an *Arabidopsis* chloroplastic glutaredoxin, is critical for protection against protein oxidative damage. J. Biol. Chem. 281, 26280-26288 (2006)). For AtGRXS17 subcellular localization in yeast assays, full-length AtGRXS17 was fused to the N-terminus of green fluorescent protein (GFP) using a procedure described previously by Cheng et al., supra. The AtGRX3-GFP fusion protein was then subcloned into the yeast vector as described above. In the experiments, vector-, yGRX3-, and AtGRXS17-expressing grx3grx4 cells were grown in SC-Ura selection media overnight. $10^7$ cells from each culture were treated at 52° C. for 0 min, 20 min, and 60 min and the cell cultures were diluted $10^4$ fold and plated on YPD media for growth of 3 days at 30° C., respectively. The numbers of colonies were counted. The bars in the graphs indicate S.D. (n=3). Student t test, *p<0.05; p<0.01; *p<0.001. AtGRX3-GFP was imaged in colocalization with yeast Grx3-RFP. The fluorescence signals were detected at 510 nm (excitation at 488 nm) for GFP, at 582 nm (excitation at 543 nm) for DsRed.

Example 2

Response and Adaptation to Heat Stress in AtGRXS17-Expressing Tomato

Generation of AtGRXS17-Expressing Tomato Plants.

To test whether AtGRXS17 may be used to improve thermotolerance of crops, we introduced a construct containing AtGRXS17 driven by the cauliflower mosaic virus (CaMV) 35S promoter into tomato (*Lycopersicon esculentum* cv. Rubion). Seeds of tomato *Lycopersicon esculentum* (cv. Rubion) were surface sterilized and germinated on the Murashige and Skoog (A Revised Medium for Rapid Growth and Bio Assays with Tobacco Tissue Cultures. Physiol. Plantarum 15, 473-497 (1962)) inorganic salt medium. Tomato transformation was performed via *Agrobacterium*-mediated transformation method using cotyledon and hypocotyls explants as previously described (Park et al. Efficient and genotype-independent *Agrobacterium*-mediated tomato transformation. J. Plant Physiol. 160, 1253-1257 (2003)). *Agrobacterium tumefaciens* LBA 4404 was used for generating stable transgenic plants. The plasmid pCaMV35S::AtGRXS17 and pCaMV35S::AtGRXS17-GFP was introduced into *A. tumefaciens* using the freeze-thaw method (Holsters et al. Transfection and Transformation of *Agrobacterium-Tumefaciens*. Mol. Gen. Genet. 163, 181-187 (1978)). After inoculating with *A. tumefaciens*, the plant cultures were maintained at 25° C. under a 16-h photoperiod. After 6 to 8 weeks, regenerated shoots were transferred to rooting medium for 6 more weeks. The temperature of the greenhouse was maintained within a range of 25° C. to 30° C.

Figure 3:
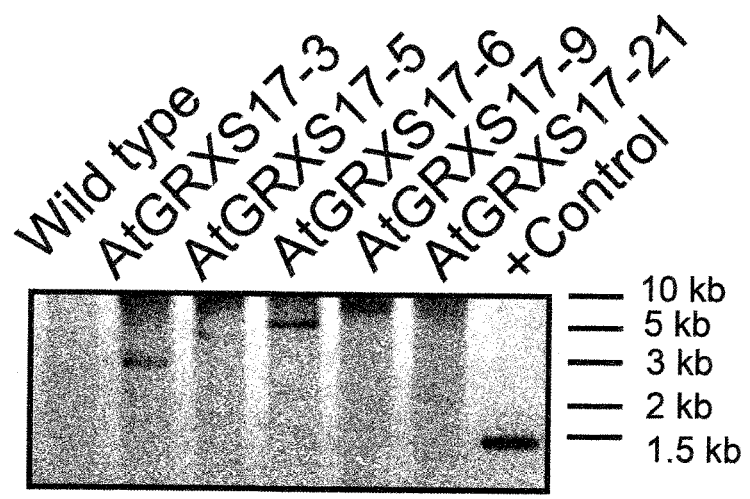
FIG. 3 shows the DNA gel blot analysis from Example 2, which confirmed the stable integration of AtGRXS17 into the genome of tomato plants.

More than 20 independent transgenic lines were generated and 4 morphologically normal lines containing single transgene insertions (based on Southern blot analysis) were selected for the further research (AtGRXS17 #3, 5, 6 and 9; FIG. 3). For DNA and Southern-blot analysis, tomato genomic DNA was extracted from leaf tissue by Qiagen Plant DNA extraction kit. DNA (10 µg) was digested with XbaI and separated by electrophoresis and blotted onto a nylon membrane (Zeta-probe GT membrane, Bio-Rad Laboratories) according to the manufacturer's instructions. The probe for the AtGRXS17 gene was isolated from a pGEM-T-easy vector contained AtGRXS17 by enzyme digestion. The membranes were prehybridized overnight 3 hours at 65° C. in 7% SDS and 0.25 M Na2HPO4, and then hybridized overnight at 65° C. in the same solution containing the probe labeled by NEBlot Phototope Kit (New England Biolabs). Membrane were washed twice for 40 min each with 20 mM Na2HPO4 and 5% SDS at 65° C. and then washed twice again for 30 min each with 20 mM Na2HPO4 and 1% SDS at 65° C. The signal was detected by Phototope-Star Detection Kit (New England Biolabs) according to the manufacture's instruction. The T1 seeds of these 4 lines showed a segregation pattern of 3:1 for the kanamycin resistance marker gene consistent with a single insertion.

Figure 4:
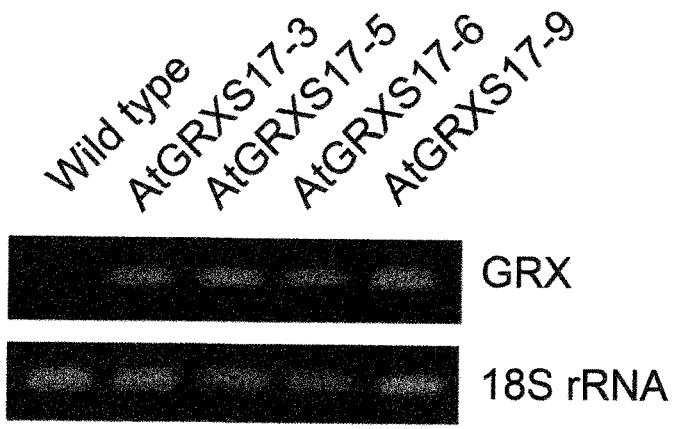
FIG. 4 shows the RT-PCR confirmation of AtGRXS17 expression in different lines.

To obtain homozygous T2 AtGRXS17 lines, segregation analysis on T2 seeds from self-pollinated T1 AtGRXS17 plants was carried out on 100 mg/liter kanamycin selection medium, and the expression of AtGRXS17 was examined by reverse transcriptase (RT)-PCR analysis (FIG. 4). Total RNA was isolated using the Qiagen Plant RNeasy kit from leaves of tomato plants according to the manufacturer's instructions. RNA for real-time PCR was treated with RNase-free DNase prior to the synthesis of first-strand cDNA by oligo (dT) priming using moloney murine leukemia virus-reverse transcriptase (BD Biosciences Clontech, Palo Alto, Calif., USA). One microliter of the reverse transcription reaction solution was used as a template in a 25 µL PCR solution. Real-time PCR was performed in 25 µL reactions contain 10 µL cDNA, 0.4 µM of each primer, and 12.5 µL SYBR Green PCR Master Mix (Bio-Rad Laboratories). Analysis was performed using the Bio-Rad IQ3 (Bio-Rad Laboratories). Primer efficiencies were measured and relative expression level was calculated using the comparative Ct method. The primers for PCR are listed in the Table in FIG. 5.

Subcellular Localization of AtGRXS17 with or without Heat Stress.

To investigate the subcellular localization of AtGRXS17 in plant cells, the GFP-AtGRXS17 fusion was transiently expressed in epidermal cells of tobacco leaves (*Nicotiana benthamiana*) through *Agrobacterium*-infiltration. Full-length AtGRXS17 was fused to the C-terminus of green fluorescent protein (GFP) using a procedure described previously (Cheng et al. 2006). The GFP-AtGRXS17 construct was made by LR reaction (Invitrogen) between the binary vector pB7WGF2 (Karimi et al. GATEWAY™ vectors for *Agrobacterium*-mediated plant transformation. Trends Plant Sci. 7, 193-195. (2002)), and the entry vector carrying AtGRXS17 (pENTR-4, Invitrogen, Carlsbad, Calif.). pB7WGF2/GFP-AtGRXS17 was introduced into *Agrobacterium* strain GV3101 and then used for agro-infiltration as previously described (Liu et al. The tobacco mosaic virus 126-kilodalton protein, a constituent of the virus replication complex, alone or within the complex aligns with and traffics along microfilaments. Plant Physiol. 138, 1853-1865. (2005)). For heat shock treatment, at 1.5 to 2 days post-infiltration (DPI), the infiltrated leaves were detached from tobacco plants, kept in Petri dishes with the moistened filter paper, and incubated at 25° C. or 42° C. for 90 min, respectively.

The GFP-AtGRXS17 signals were primarily detected in the cytoplasm and the nuclear envelope, whereas relatively weaker signal could be detected in the nucleus under normal growth conditions (FIG. 6). At increased temperatures, GFP-AtGRXS17 predominately accumulated in the nucleus, whereas free GFP targeted to nuclei independent of heat treatment (FIG. 6).

Figure 7:
FIG. 7 is a photograph of wild type and AtGRXS17-GFP-expressing tomato plants after being treated at 38° C./28° C. (day/night) for 3 days, followed by 42° C./32° C. (day/night) for 3 more days.
Figure 8:
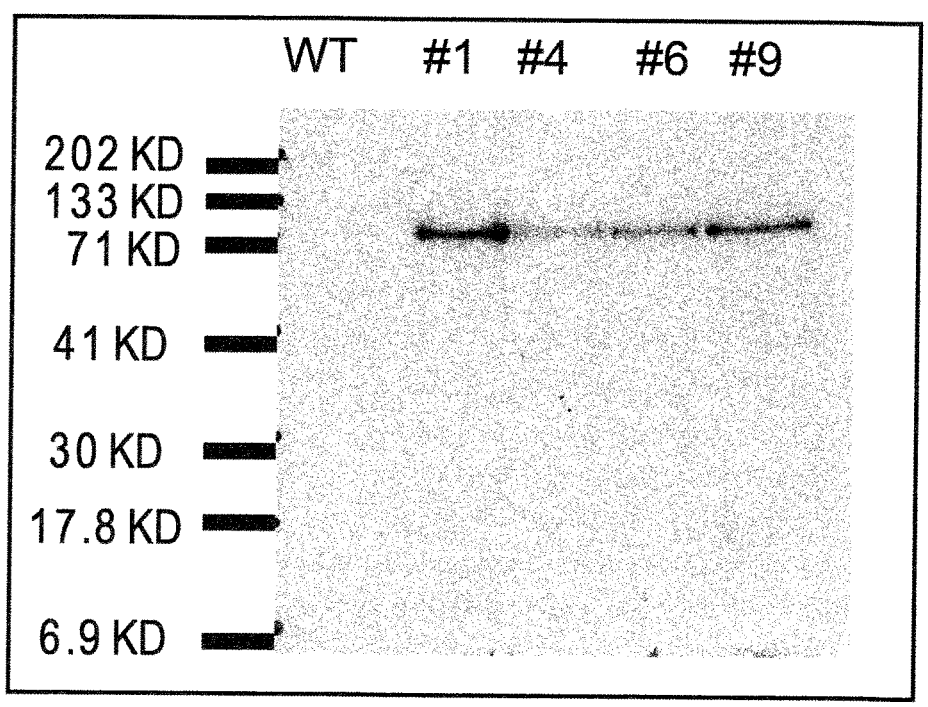
FIG. 8 is an image of the immunoblot detection of GFP-tagged recombinant proteins extracted from wild type and AtGRXS17-GFP-expressing tomato plants.
Figure 9:
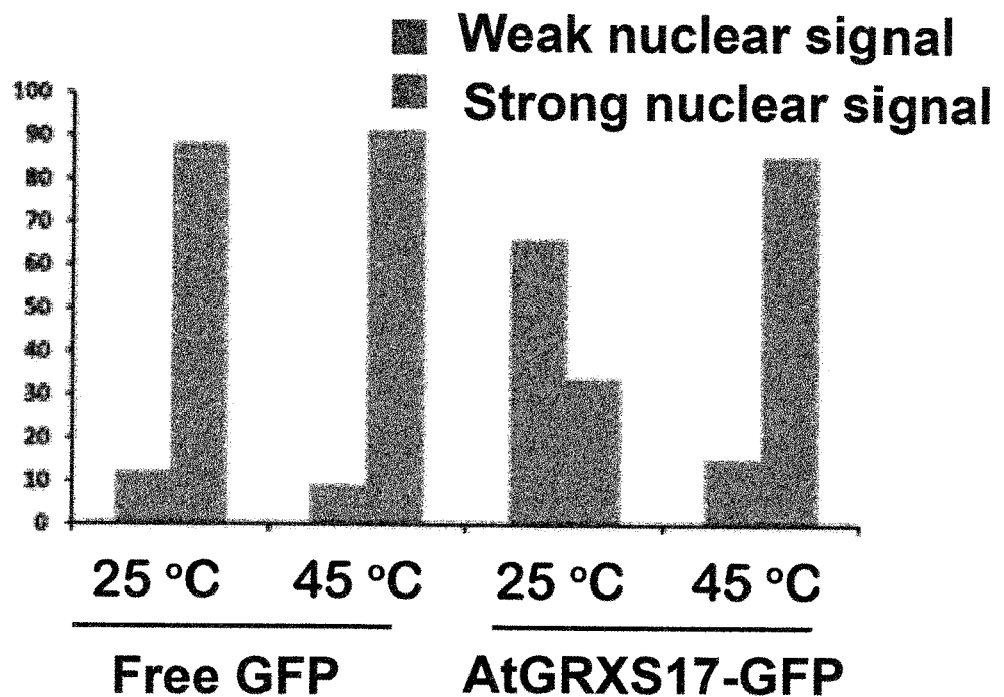
FIG. 9 shows a graph of the total 100 nuclei counted for fluorescent signals. The percentage of weak or strong nuclear signals was recorded.

In order to further investigate the AtGRXS17 subcellular localization in tomato plants, we generated 4 stable AtGRXS17-GFP-expressing tomato plants driven by CaMV35S promoter. For AtGRXS17-GFP localization in tomato stomatal cells, 30-day-old stable AtGRXS17-GFP-expressing plants were treated by either heat or control treatments before observation under microscopy. All AtGRXS17-GFP-expressing tomato plants showed significantly improved thermotolerance in comparison with wild type plants (FIG. 7). In addition, the expression of AtGRXS17-GFP could be detected by immunoblot using a GFP-antibody (FIG. 8). During a heat stress, we could detect GFP signals in the nucleus of a number of stomatal (FIG. 9), while no GFP signals in the nuclei could be detected under normal growth conditions. Together, these data indicate that AtGRXS17 translocate from the cytoplasm into the nucleus under heat stress. Images in this Example were captured with a confocal laser scanning system (Leica, SP5 X) and fluorescence microscope (Zeiss AxioPlan). The fluorescence signals were detected at 510 nm (excitation at 488 nm) for GFP, at 582 nm (excitation at 543 nm) for DsRed.

Response and Adaptation to Heat Stress in AtGRXS17-Expressing Tomato.

Figure 10:
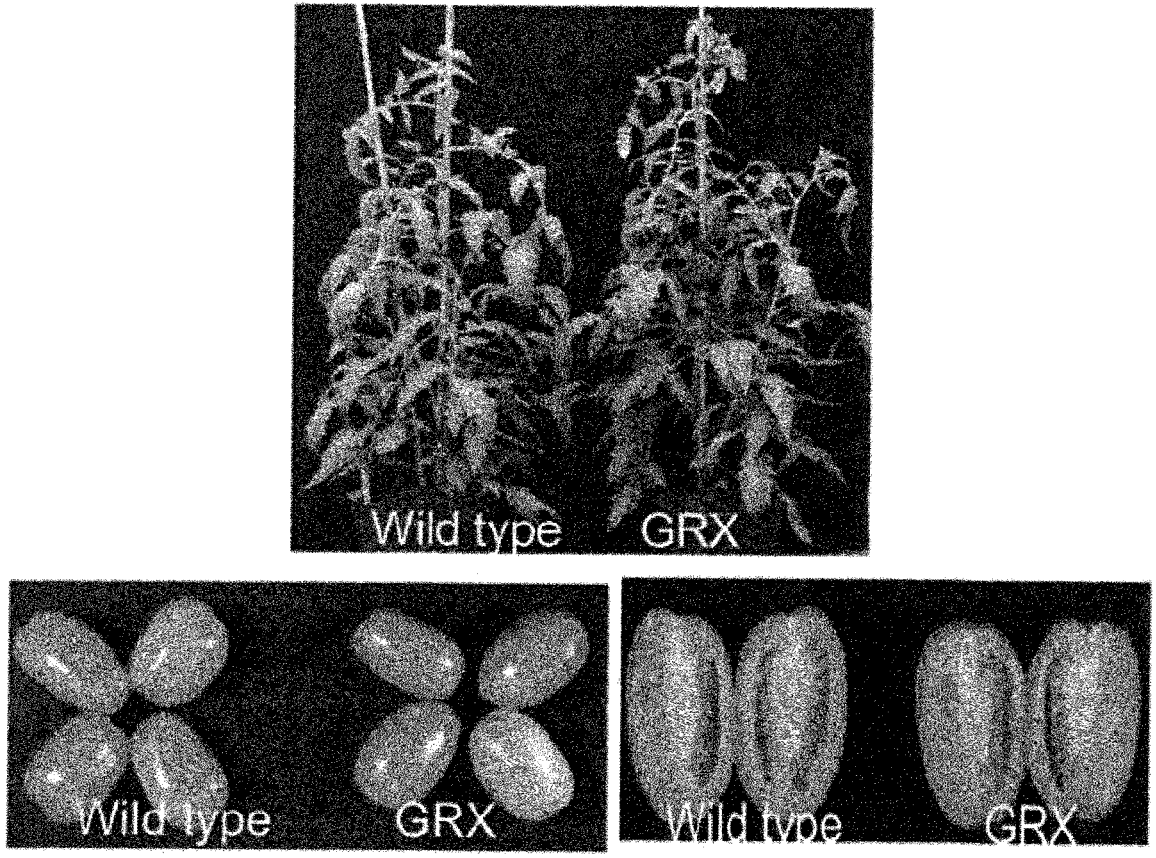
FIG. 10 shows photographs indicating that the growth and development of the tomato plants is indistinguishable before heat treatment, indicating that the expression of AtGRXS17 does not adversely affect the plant or fruit phenotype or yield.
Figure 11:
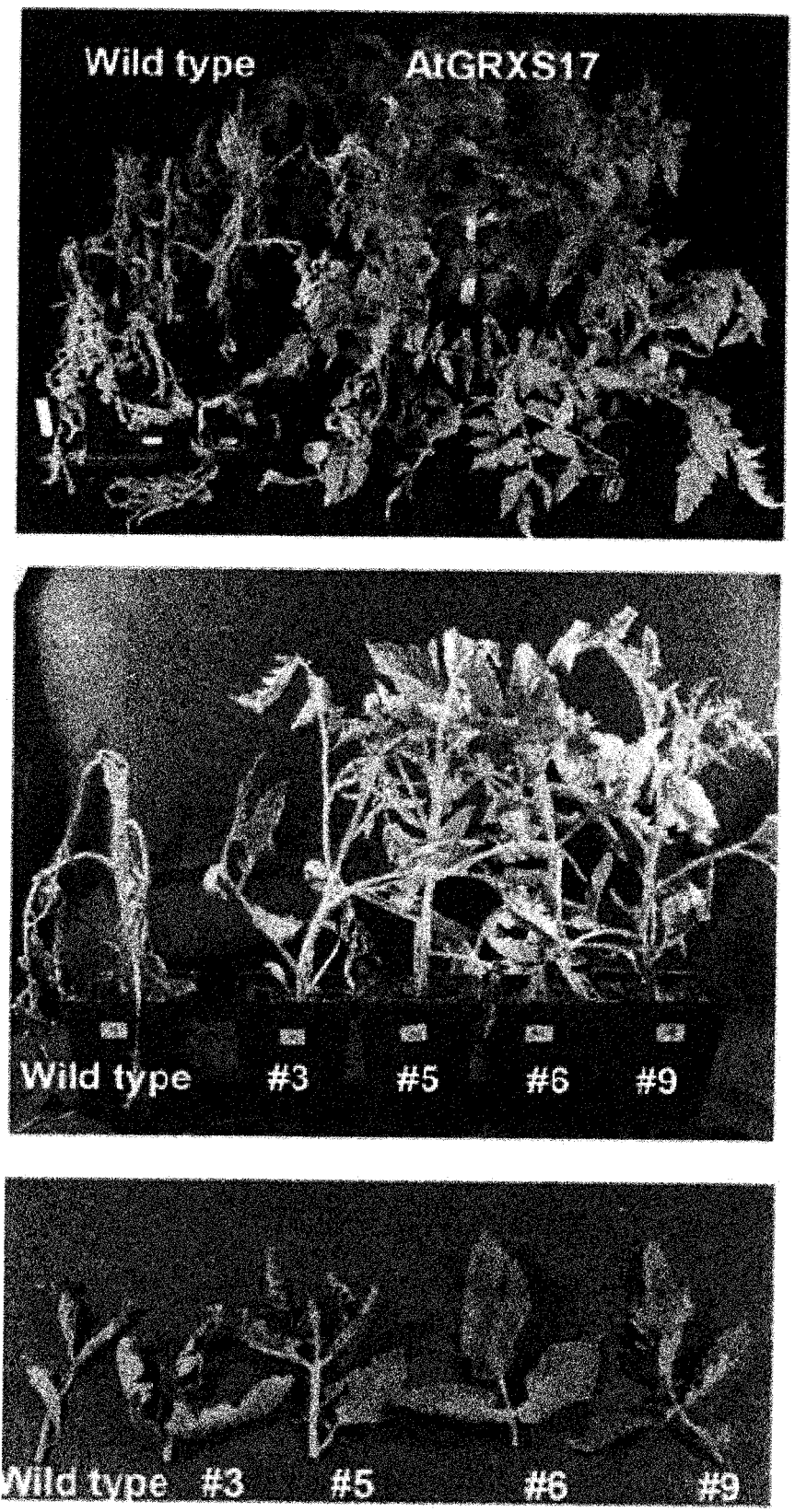
FIG. 11 shows photographs depicting the comparative heat tolerance of the wild type vs. the AtGRXS17-expressing tomato plants.
Figure 12:
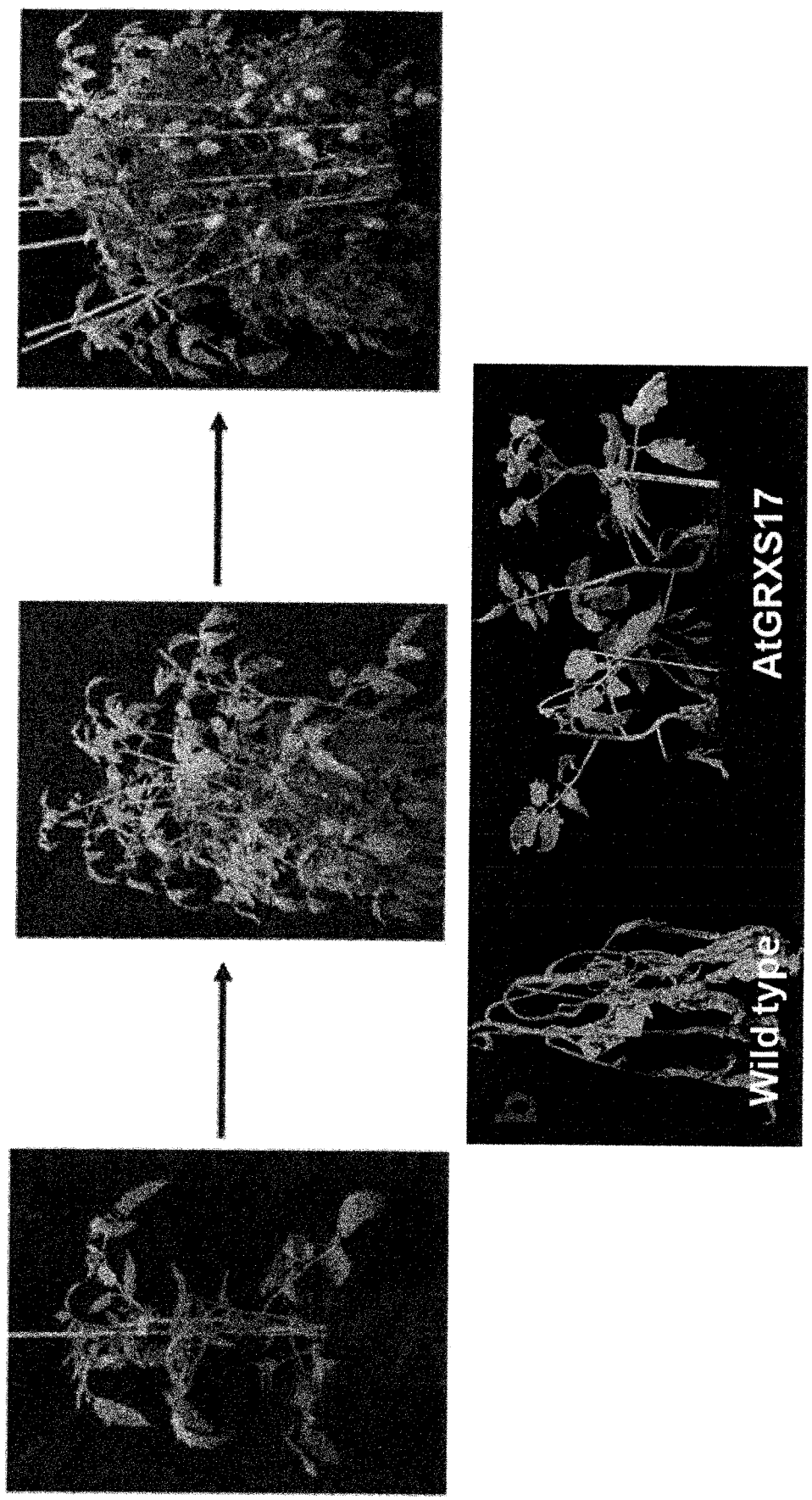
FIG. 12 shows photographs of the plants depicting the recovery of the AtGRXS17-expressing tomato plants when transferred to normal growing conditions after 6 days of heat treatment, as compared to the wild-type plant, which was unable to recover.

For heat tolerance experiment, each of 35 homozygous T2 AtGRXS17 plants derived from selected four T1 transgenic lines (AtGRXS17 #3, 5, 6 and 9) were analyzed. T2 generation AtGRXS17-expressing transgenic or wild type tomato seeds were surface sterilized and germinated on MS medium with 100 mg/L kanamycin or without kanamycin, respectively. Positive candidates were selected after 15 days and transferred to pots containing Miracle Gro (700) soil growing medium and grown in the growth chamber with the temperature of 25° C./22° C. (day/night) under a 16-h photoperiod. The plants were regularly watered and fertilized on a weekly basis with 20:20:20 fertilizer (Scotts). The 4-weeks-old seedlings were treated under 38° C./28° C. (day/night) for 3 days and then 42° C./32° C. (day/night) for 3 more days. The growth and development of AtGRXS17-expressing tomato plants were indistinguishable from those of wild-type plants before heat treatment (FIG. 10). Moreover, expression of AtGRXS17 did not affect fruit shape and yield (FIG. 10). AtGRXS17-expressing tomatoes displayed robust growth and heat tolerance after 3 days at 38/28° C. (day/night, 16-h photoperiod) followed by 3 days at 42/32° C. (day/night, 16-h photoperiod), whereas the wild-type plants were severely damaged during these growth conditions (FIG. 11). In addition, the transgenic plants were recovered when transferred to 25° C./22° C. (day/night) for growth (FIG. 12).

The enhanced heat stress tolerance of the transgenic plants was further verified by measuring changes in chlorophyll fluorescence and electrolyte leakage of leaves. Chlorophyll fluorescence from the adaxial side of the leaf was monitored using a portable chlorophyll fluorometer (PEA, Hansatech Instruments, Ltd., UK). Photochemical efficiency of leaves as determined by chlorophyll fluorescence ratios (Fv/Fm) was monitored during and after the heat treatment. Measurements were made during the light cycle on the leaves using the saturation pulse method after 30 min of dark adaption. For electrolyte leakage, leaf samples were incubated in 15 ml of distilled water for 10 h to measure the initial electrolyte leakage using an YSI conductance meter (Model 32, YSI, Inc., Yellow Springs, Ohio, USA). The samples were subjected to 80° C. for 2 h to release the total electrolytes and then held at room temperature for 10 h. The final conductivity on the leachate was measured to determine the percent electrolyte leakage from the leaf samples. The chlorophyll fluorescence Fv/Fm ratio, indicating the maximum quantum efficiency of Photosystem II, were similar in the AtGRXS17-expressing transgenic plants and the wild plants during the initial 3 d treatment; however, following 3 d at 42° C./32° C. (day/night), the Fv/Fm ratio of wild type plants was significantly lower than that of AtGRXS17-expressing transgenic plants (FIG. 13A). Moreover, the electrolyte leakage of wild type plants was significantly higher than that of AtGRXS17-expressing transgenic plants, indicating increased plasma membrane integrity and reduced disruption of cell membranes in the transgenic lines (FIG. 13B).

Figure 14:
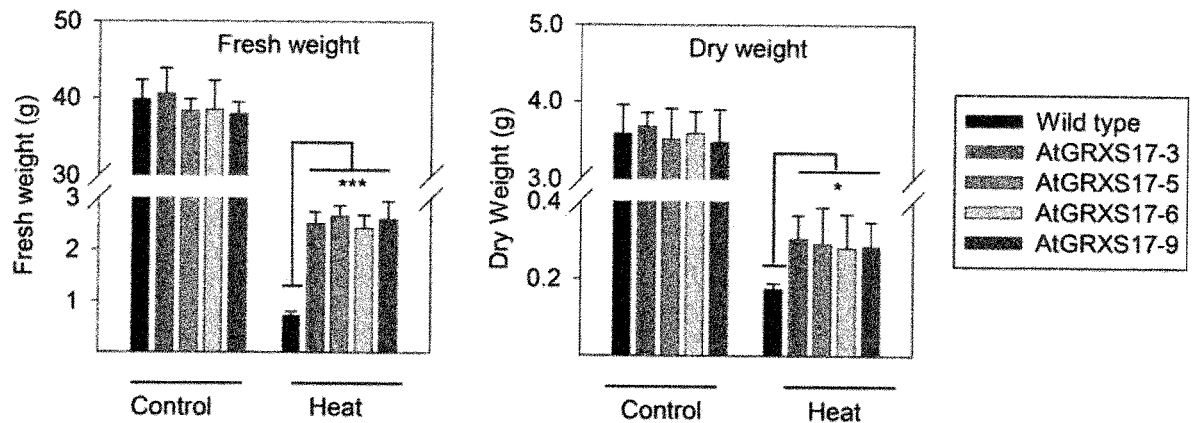
FIG. 14 shows graphs of the above-ground fresh weights and dry weights of wild type and AtGRXS17-expressing plants after heat treatment growth for 28 days as compared with Control (normal growing conditions)

The enhanced heat stress tolerance of the AtGRXS17-expressing transgenic plants compared with wild-type plants was also confirmed by measuring above-ground fresh and dry weight of the plants. The fresh and dry weight of wild-type and AtGRXS17-expressing transgenic plants did not show significant difference when grown under normal temperature for 2 months. However, after being treated by heat stress, the AtGRXS17-expressing transgenic plants displayed significantly higher fresh and dry weight yields than those of the wild-type plants (FIG. 14). The transgenic plants demonstrated more robust recovery when transferred to 25/22° C. (day/night, 16-h photoperiod), and the yield of the AtGRXS17-expressing tomatoes was indistinguishable from that of wild-type controls under normal growth conditions.

Catalase Enzyme Activity and Accumulation of $H_2O_2$ in AtGRXS17-Expressing Tomato.

Heat stress is accompanied by the formation of ROS such as $.O_2^-$, $H_2O_2$, and OH radicals which damage membranes and macromolecules. To investigate the potential mechanism by which AtGRXS17 improved thermotolerance in tomato, we measured $H_2O_2$ accumulation by using 3,3'-diaminobenzidine (DAB) staining leaves from each of 2 homozygous T2 AtGRXS17 lines (AtGRXS17 #6 and 9). Leaves from 4-weeks-old wild type and AtGRXS17-expressing tomato plants were used for the DAB (3, 3'-diaminobenzidine) staining. For the in vivo detection, the tomato plants were treated by 42° C./32° C. (day/night) for 48 hours, and then the leaves were cut and incubated in water containing 1 mg/mL DAB solution (pH 3.8) at 25° C. in the dark for 1 h to take up the stain. For the in vitro detection, tomato leaves were cut and immediately immersed into water containing 1 mg/mL DAB solution (pH 3.8) and kept at 25° C. (for control) and 42° C. (for heat treatment) in the dark for 3 hours. Then the leaves were bleached by immersing in boiling 95% ethanol to visualize the brown spots.

Figure 15:
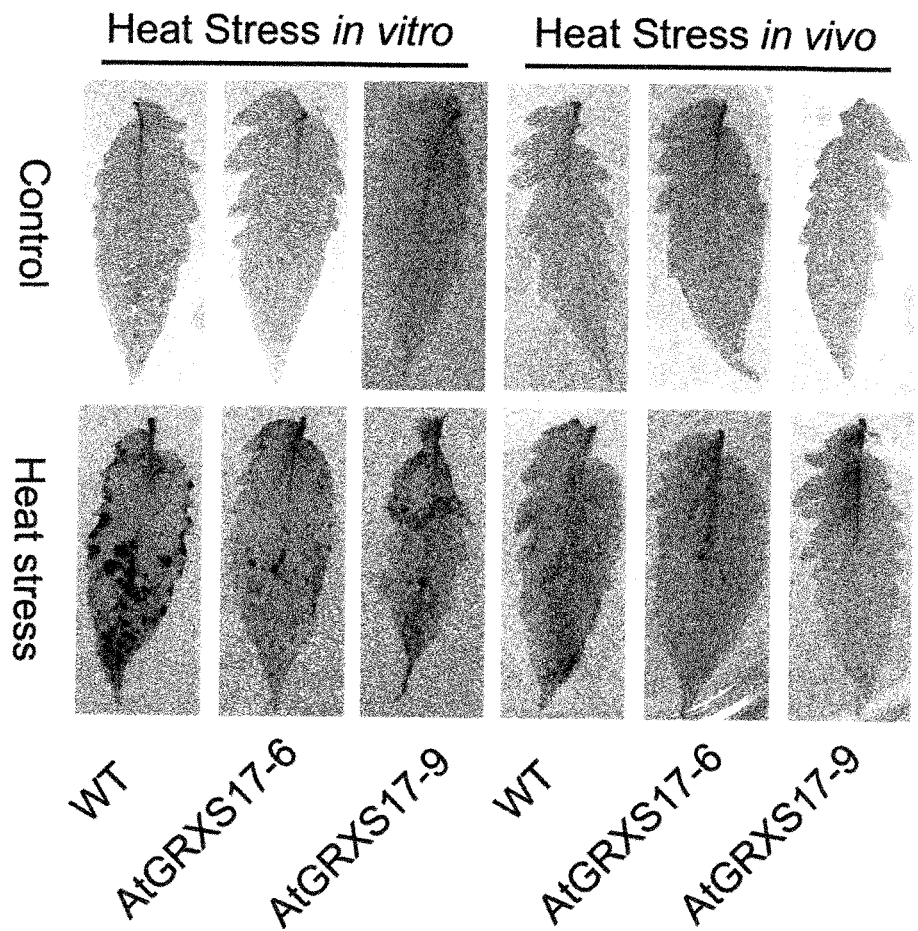
FIG. 15 shows images demonstrating the effects of heat stress on the accumulation of $H_2O_2$ in the leaves of 30-day-old wild-type (WT) and AtGRXS17-expressing (GRXS17 #6 and GRXS17 #9) tomato plants.
Figure 16:
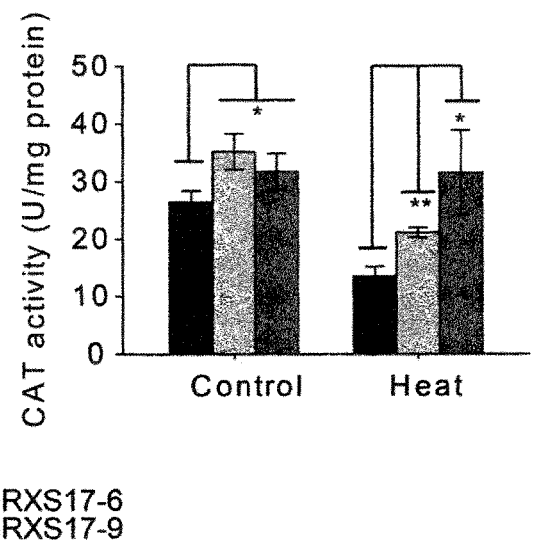
FIG. 16 shows a graph of the effects of AtGRXS17-expression on the CAT (catalase) activity under control or heat treatments. Control, the 33-day-old tomato plants grown under normal growth condition as describe above. Heat, the 30-day-old tomato plants were grown under normal growth condition and then treated at 42° C./32° C. (day/night) for 3 days.

In both the in vitro and in vivo tests, the leaves of AtGRXS17-expressing plants displayed less intense staining than that of the controls under the heat stress regime, indicating less $H_2O_2$ accumulation in the transgenic lines (FIG. 15). Although glutaredoxins have been known to perform their functions as antioxidants, it is interesting to investigate the effects of ectopic expression of AtGRXS17 in tomato on the activities of other antioxidant components. We next compared to the peroxidase (POD), catalase (CAT), and glutathione reductase (GR) activities of wild type and AtGRXS17-expressing plants in both normal growth conditions and a heat stress. Four-week-old seedlings were treated by 42° C./32° C. (day/night) for 4 days, and then the shoots were harvested and homogenized (1:5 m/v) in liquid nitrogen. The resulting powder was suspended in an ice cold protein extraction buffer made by 50 mM PBS, 1% PVP and 1 mM PMSF, and centrifuged at 13000×g for 15 min at 4° C. The protein concentration was measured by BCA protein assay kit (Pierce). The activity of CAT was assayed by measuring the rate of disappearance of $H_2O_2$ at 240 nm, following the method of Ouyang et al. (Receptor-like kinase OsSIK1 improves drought and salt stress tolerance in rice (*Oryza sativa*) plants. Plant Journal 62, 316-329 (2010)). One unit of the CAT activity was defined as 0.01 absorbance decrease per minute at 240 nm. There were 6 biological replicates for each data points. The activities of CAT, but not those of GR and POD, were significantly increased in all AtGRXS17-expressing lines when compared to wild type plants after heat treatment. These data indicate that CAT activity is significantly highly induced by expression of AtGRXS17, suggesting AtGRXS17 may regulate CAT activity (FIG. 16). Together, these results demonstrate that ectopic expression of AtGRXS17 protects tomatoes from a heat stress by reducing ROS accumulation through its own antioxidant activity and higher activity of CAT than that of the controls.

Expression Analysis of HSPs in AtGRXS17-Expressing Tomato.

The induction of HSPs is one of the predominant events of response to temperature stress and these HSPs perform important physiological functions as molecular chaperones for protein quality control, such as preventing the aggregation of denatured proteins and promoting the renaturation of aggregated protein molecules caused by high temperature. Given that AtGRXS17-expressing tomatoes are highly tolerant to heat stress, a possible interaction between AtGRXS17 and HSPs was further investigated.

Figure 17:
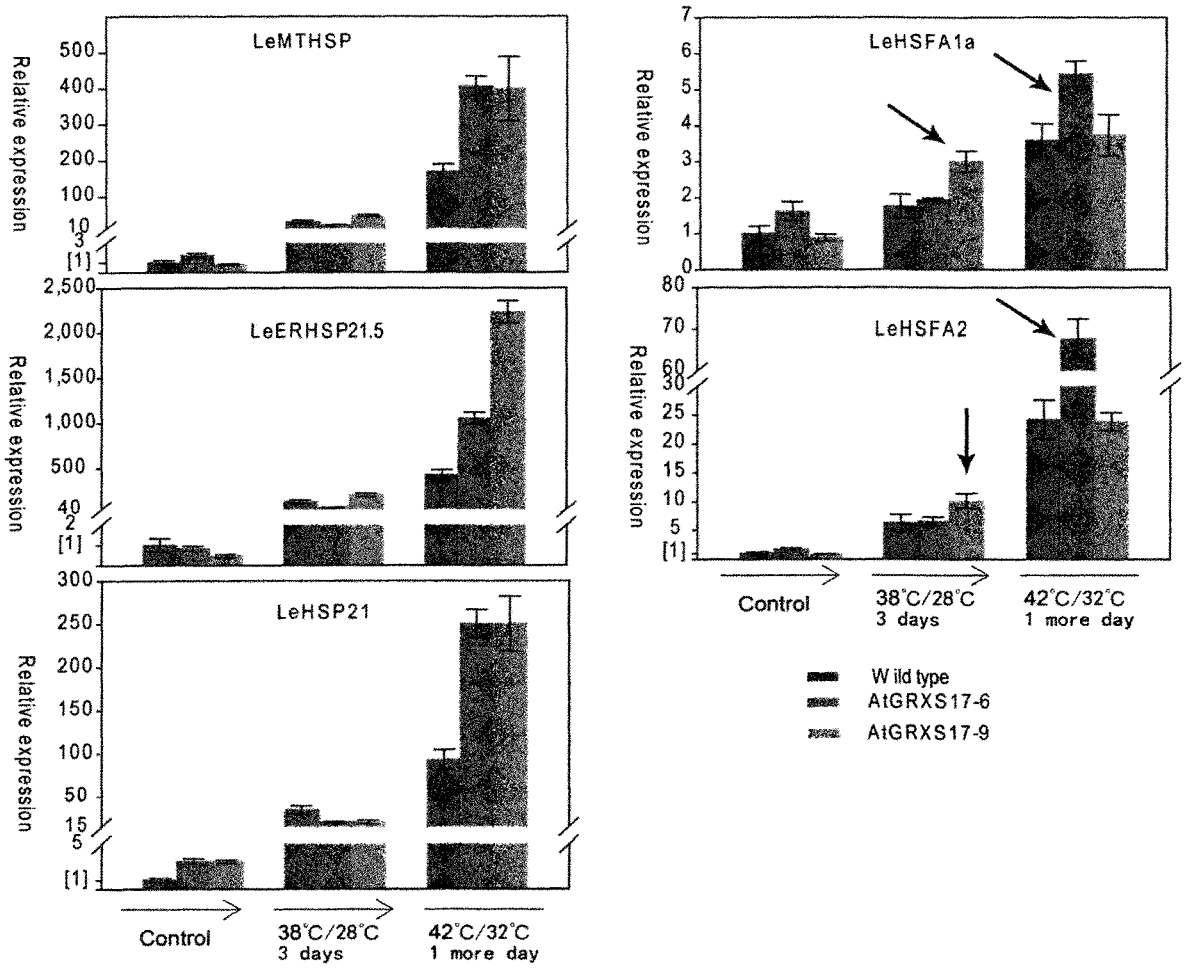
FIG. 17 shows graphs of the expression analysis of heat shock proteins (HSP) and heat shock factors (HSF) in the wild type and AtGRXS17-expressing tomato plants by qRT-PCR. Data are expressed as relative values based on wild type plants grown under control condition as reference sample set to 1.0.

To evaluate how the AtGRXS17-expressing tomato in response to heat stress influences expression levels of HSPs, HSP21 (nuclear coding gene located at chloroplast), LeER-HSP21.5 (endoplasmic reticulum-located small heat shock protein), and LeMTSHP (mitochondrial small heat shock protein) were selected for real time quantitative PCR (qRT-PCR) analysis (FIG. 5). After 3 days at 38° C./28° C. (day/night), both wild-type and AtGRXS17-expressing tomato (AtGRXS17 #6 and 9) showed significantly increased expression of all selected HSPs as compared to normal growth condition (25° C./22° C.) (FIG. 17). Moreover, after 3 d at 38° C./28° C. plus 1 d at 42° C./32° C., both wild-type and AtGRXS17-expressing tomato also showed significantly increased expression of all selected HSPs, exhibiting >100-fold elevated expression, as compared to after 3 d at 38° C./28° C.; however, expression levels of all selected HSPs in the AtGRXS17-expressing tomato plants were significantly higher than those of the wild-type plants after 1 d at extreme high temperatures (42° C./32° C.), exhibiting >2.5 to 4-fold elevated expression. These data suggest that AtGRXS17 predominantly stimulates up-regulation of the HSPs involved in plant heat stress responses and thermotolerance.

Expression Analysis of HSFs in AtGRXS17-Expressing Tomato.

Heat shock transcription factors (HSFs) are the terminal components of signal transduction regulating the expression of HSPs and play an important role in heat stress responses and thermotolerance of plants. Given that AtGRXS17-expressing tomatoes showed highly elevated expression levels of all tested HSPs under heat stress, a possible interaction between AtGRXS17 and HSFs was also further investigated. In this study, we selected two different tomato HSFs, HsfA1a and HsfA2, for qRT-PCR analysis (FIG. 5). HsfA1a has been defined as a master regulator of heat stress response in tomato, whereas HsfA2 is an important HSF for thermotolerance. After 3 d at 38° C./28° C. (modest heat treatment), AtGRXS17-expressing tomato (AtGRXS17 #9) showed significantly increased expression of both LeHSFA1a and LeHSFA2 as compared to wild-type (FIG. 17). However, after 3 d at modest heat treatment plus 1 d at 42° C./32° C., AtGRXS17-expressing tomato (AtGRXS17 #6) showed significantly increased expression of both LeHSFA1a and LeHSFA2 as compared to wild-type and AtGRXS17 #9 line (FIG. 17). These data suggest that AtGRXS17 also stimulates up-regulation of the HSFs, although AtGRXS17-expressing tomato lines could show different temporal expression patterns of the HSFs in response to the degree of heat stress.

Response and Adaptation to Cold Stress in AtGRXS17-Expressing Tomato.

AtGRXS17-expressing tomatoes grew after 1 d at 2° C. followed by 13 d at 4° C., whereas the wild type plants were severely damaged by the cold stress. In addition, the transgenic plants were recovered when transferred to 25° C./22° C. (day/night) for growth. The enhanced cold stress tolerance of the transgenic plants was further verified by measuring changes in chlorophyll fluorescence and electrolyte leakage.

Response and Adaptation to Drought Stress in AtGRXS17-Expressing Tomato.

Drought stress phenotypes were assayed by imposing a 10 d water deficit stress period, after which irrigation of both control and AtGRXS17-expressing tomatoes were withheld. AtGRXS17-expressing tomatoes did not display deleterious phenotypes after withholding irrigation for 10 d, whereas the wild type plants were severely damaged by the drought stress. Transgenic plants maintained greater shoot water potentials during imposed soil water deficits and the Fv/Fm ratio of wild type plants was significantly lower than that of AtGRXS17-expressing transgenic plants.

Example 3

Response and Adaptation to Heat Stress in AtGRXS17-Expressing Rice

In this experiment, rice (*Oryza sativa* L. var. *japonica*) cv. Nipponbare was used for producing transgenic rice with AtGRXS17 driven by the CaMV 35S promoter. Rice transgenic lines were generated via *Agrobacterium*-mediated transformation using mature seed-derived callus as previously established in the Park laboratory (Park et al., 2000; Park et al., 2001). Calli derived from mature seed on MSD medium with Murashige and Skoog (1962) inorganic salts, 100 mg/liter myo-inocitol, 0.5 mg/liter nicotinic acid, 0.5 mg/liter pyridoxin, 0.1 mg/liter thiamine-HCl, 1.0 mg/liter 2,4-D, 30 g/liter sucrose, and 0.8% (w/v) agar at pH 5.7 was cocultivated with *A. tumefaciens* (LBA4404) on the MSD medium at pH 5.2. The binary vector plasmid (pVKH18En6, gifted from John Runion's lab) with 35S::AtGRXS17 was used. After 2 days co-cultivation, calli were transferred to the MSD medium covered with sterile filter paper for 3 more days. After co-cultivation for a total of 5 days, the calli were transferred to MSD medium containing 250 mg/liter Clavamox (amoxicillin trihydrate) for 1 week. Calli were then transferred to selection medium, MSD medium containing 250 mg/liter Clavamox and 50 mg/liter Hygromycin (Roche). After subsequent rounds of selection, proliferating calli was divided and transferred to regeneration medium containing MS inorganic salts, 100 mg/liter myo-inocytol, 0.5 mg/liter nicotinic acid, 0.5 mg/liter pyridoxin, 0.1 mg/liter thiamine.HCl, 1.0 mg/liter kinetin, 0.2 mg/liter NAA, 250 mg/liter Clavamox, 50 mg/liter hygromycin, 30 g/liter sucrose, and 0.8% (w/v) agar. Cultures were maintained at 25° C. for 16 h under 60-80 μmol $m^{-1}s^{-1}$ light. After 8-10 weeks, regenerated shoots were transferred to rooting medium containing 250 mg/liter Clavamox and 50 mg/liter hygromycin for 4 more weeks, then established in soil.

AtGRXS17-expressing rice grew more healthy after 3 d at 38° C./28° C. (day/night) followed by 14 d at 42° C./32° C.

Figure 18:
FIG. 18 shows photographs of wild type and AtGRXS17-expressing rice after heat stress.

(day/night), whereas the wild type plants were severely damaged by the same growth conditions (FIG. 18). In addition, the transgenic plants were recovered when transferred to 25° C./22° C. (day/night) for growth (data not shown).

Discussion Examples 1-3

In the present study, glutaredoxin AtGRXS17 has been characterized and the data demonstrates that AtGRXS17 is a critical mediator of heat stress-related genes and influences heat stress responses by protecting against oxidative damage in cells. In addition, the data indicates that some glutaredoxin's functions are conserved across species. Yeast, as well as monocot and dicot plants with mutants in glutaredoxins are sensitive to redox stress and elevated temperatures. Furthermore, expression of AtGRXS17 in yeast, tomato, and rice cells suppressed these sensitivities. The data suggests a model where AtGRXS17 functions to alter ROS signals and controls thermotolerance. The results indicate that ectopic expression of AtGRXS17 reduced the heat-induced $H_2O_2$ accumulation in tomato leaves, and AtGRXS17 may function in ROS scavenging.

Example 4

Drought Tolerance of AtGRXS17-Expressing Rice

The functional characterization of Arabidopsis AtGRXS17 and rice OsGRXS17 (SEQ ID NO:5), two CGFS-type genes, is reported. Mutation of AtGRXS17 in Arabidopsis and reduced expression of OsGRXS17 (SEQ ID NO:6) by RNA-mediated silencing (residues 1295-1688 of SEQ ID NO:7) in rice significantly increased plant tolerance to drought stress. Ectopic expression of AtGRXS17 in rice also led to enhanced drought tolerance in the plants. Wild-type (WT), AtGRXS17-expressing, and OsGRXS17-silencing rice plants from the japonica rice (Oryza sativa L. cv. Nipponbare) were used in this study. Wild-type (WT) and atgrxs17 KO Arabidopsis thaliana plants were from the Columbia (Col-0) ecotype. Seeds were surface-sterilized, germinated and grown on Murashige and Skoog (MS) medium with 30 g/liter sucrose and 2 g/liter Gelrite in a growth chamber [16 h light, 100 μmol $m^{-2}s^{-1}$, 28±2° C. (rice) and 22±2° C. (Arabidopsis)].

Figure 19:
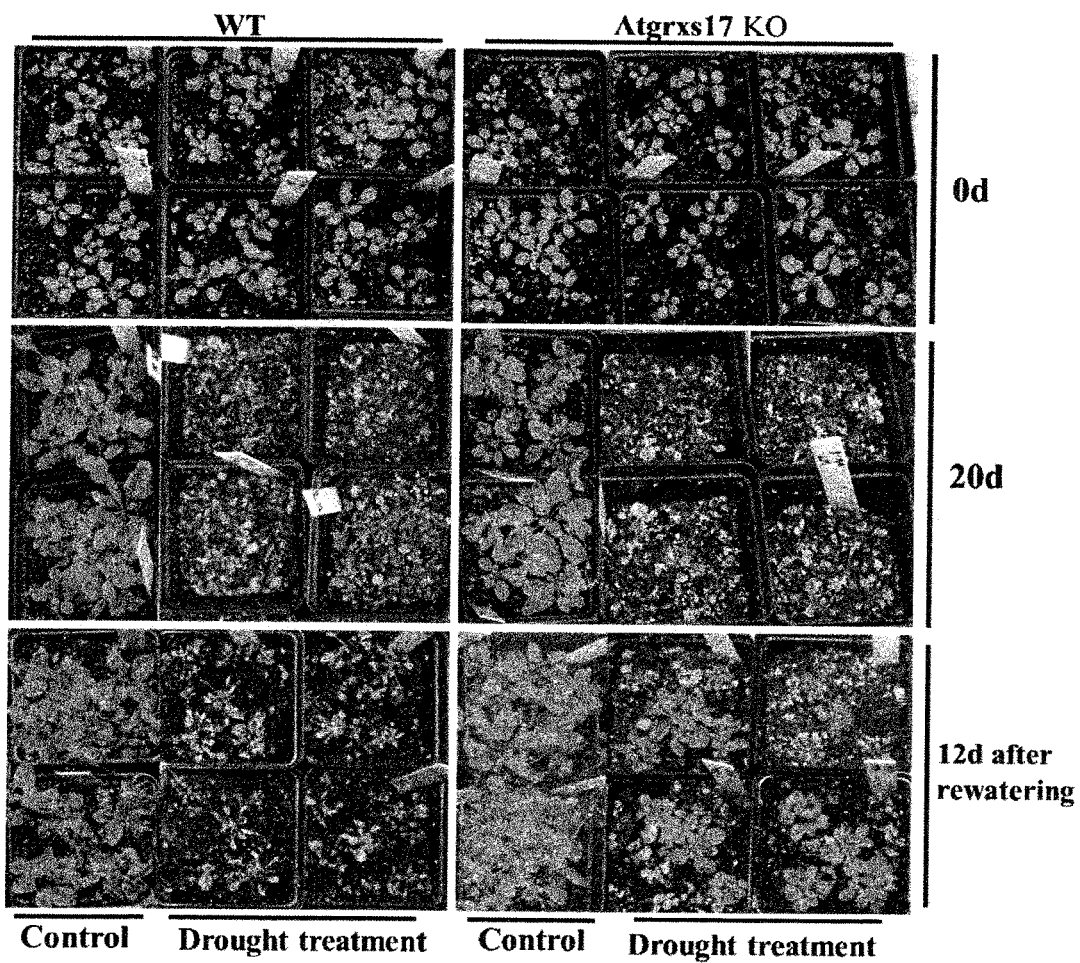
FIG. 19 shows photographs of (A) 5 weeks of *Arabidopsis* seedlings after drought stress was applied by withholding water for 20 d in a growth chamber (16 h light, 100 μmol $m^{-2}s^{-1}$, 22±2° C.), and recovery was initiated by placing pots in a shallow tray of water; and (B) Plant viability evaluated 12 d after initiation of recovery under normal growth conditions. Plants were scored as viable if one or more new leaves appear during the recovery period.

First, 5 weeks of Arabidopsis seedlings were subjected to drought stress by withholding water for 20 d in the growth chamber, and recovery was initiated by placing pots in a shallow tray of water. Plant viability was evaluated 12 d after initiation of recovery under normal growth conditions. Plants were scored as viable if one or more new leaves appear during the recovery period. None of the wild type plants survived (0% survival rate). Of the 60 AtGRXS17 KO plants, 39 survived the drought stress (65% survival rate) (FIG. 19).

Figure 20:
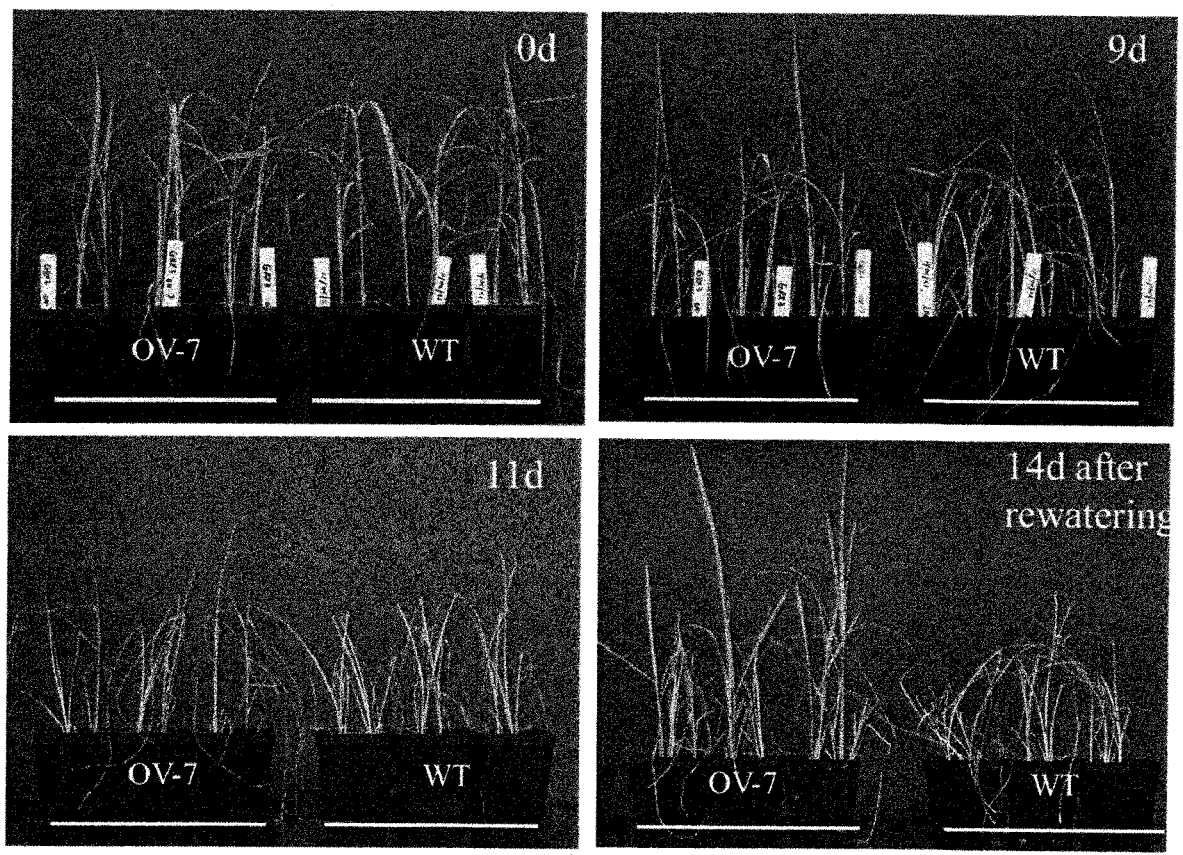
FIG. 20 shows photographs of 4 weeks of rice seedlings (transgenic line 7 and WT) after drought stress was applied by withholding water for 11 d in a growth chamber (16 h light, 100 μmol $m^{-2}s^{-1}$, 28±2° C.), and recovery was initiated by placing pots in a shallow tray of water. 0 d represents the initial day of withholding water. 9 d and 11 d represent the days after withholding water. "14 d after rewatering" represents the days after rewatering and recovering the rice plants.

Transgenic rice with ectopic expression of AtGRXS17 was subjected to drought stress. Four-week old rice seedlings (transgenic line 7 and WT) were used in this experiment. Drought stress was applied by withholding water for 11 d in the growth chamber, and recovery was initiated by placing pots in a shallow tray of water. The recover of the plants after rewatering was observed. Recovery was based upon relative water content (as measured from when the wilting first occurred during drought stress) and recover of fresh mass 14 days after rewatering. Plant survival rate was evaluated on the 14th day after rewatering under normal growth conditions. Plants were scored as viable if one or more new leaves appear during the recovery period. None of the wild type plants survived the drought stress (0% survival rate). Of the 12 initial plants, 5 survived the drought stress (41.67% survival rate) (FIG. 20).

Figure 21:
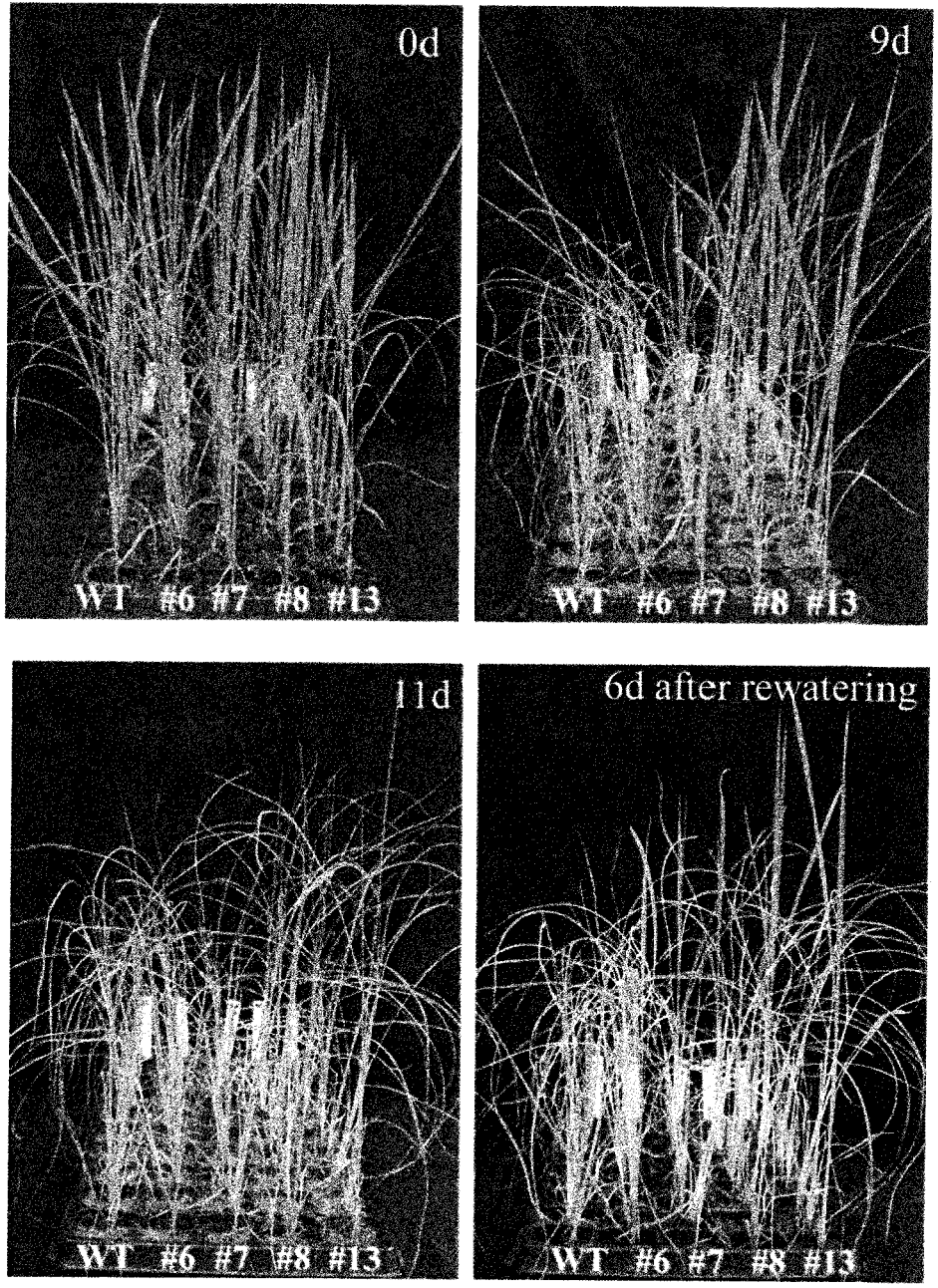
FIG. 21 shows four-week old rice seedlings (transgenic lines RNAi-6, -7, -8 and -13) with reduced expression of OsGRXS17 by RNA-mediated silencing and WT plants after drought stress treatment followed by recovery after rewatering.
Figure 22:
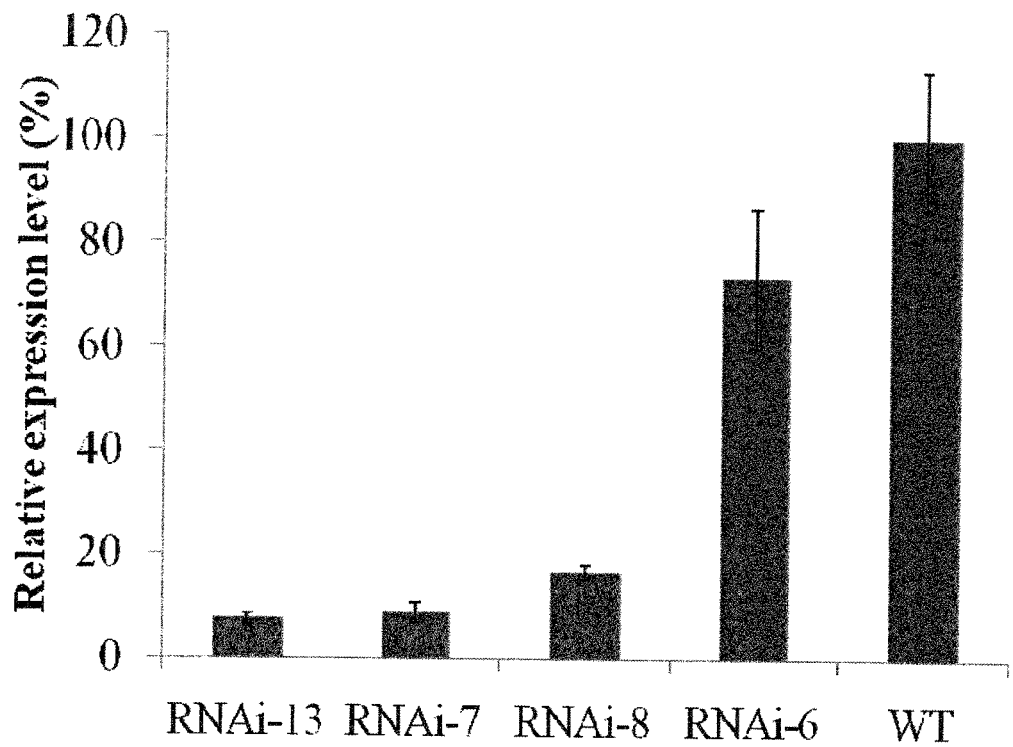
FIG. 22 is a graph of the relative expression levels of DST by quantitative real-time PCR in leaves of two-week rice plants from Example 4.
Figure 23:
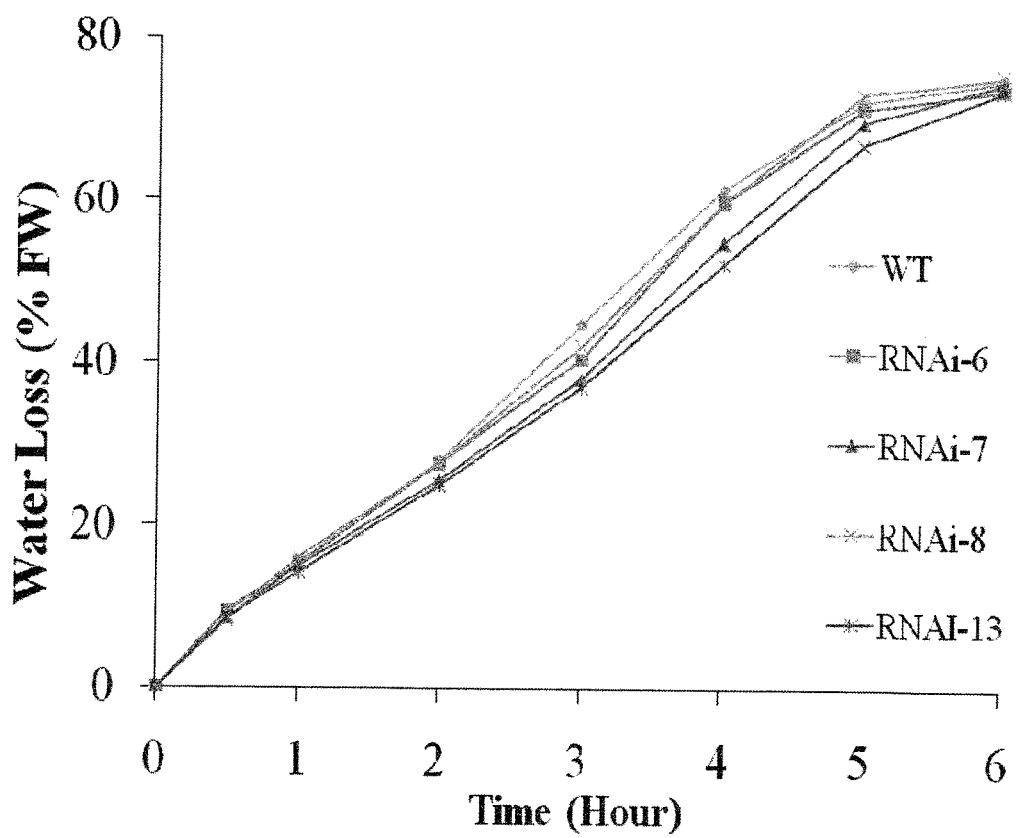
FIG. 23 is a graph of the water loss rates in Example 4 as calculated by the formula: water loss rate (%)=[(FW−DW)/FW)]*100. FW=Fresh weight, DW=Dried weight.

Four-week old rice seedlings (transgenic lines RNAi-6, -7, -8, and -13 with reduced expression of OsGRXS17 by RNA-mediated silencing and WT) were used in this experiment (FIG. 21). Methods of drought stress treatment and analysis of recovery and survival were the same as described above for the AtGRXS17-expressing plants. The results are shown in FIGS. 22-24. The survival results are shown in the Table below.

|  | Total plants | # Survived plants | Survival rate (%) |
|---|---|---|---|
| WT | 10 | 0 | 0 |
| RNAi-6 | 10 | 1 | 10 |
| RNAi-7 | 10 | 3 | 30 |
| RNAi-8 | 10 | 3 | 30 |
| RNAi-13 | 10 | 5 | 50 |

Example 5

Expression of AtGRXS17 in Tomato (Solanum lycopersicum) Enhances Tolerance to Multiple Abiotic Stresses 1. Bacterial Strains for Plant Transformation AtGRXS17 coding region was cloned into a pBICaMV vector as described (Wu et al. 2012). The CBF3 coding region was also cloned into pMDC99 vector as described (Feng et al. A three-component gene expression system and its application for inducible flavonoid overproduction in transgenic Arabidopsis thaliana. PLoS ONE 6: e17603 (2011)), and binary plasmids pMDC-CBF3 and pBICaMV-AtGRXS17 were introduced into Agrobacterium tumefaciens strain LBA4404 using the freeze-thaw method.

2. Tomato Transformation

Seeds of tomato Solanum lycopersicum L. (cv Rubion) were surface sterilized and germinated on the Murashige and Skoog (MS) inorganic salt medium. Tomato transformation was performed via Agrobacterium-mediated transformation method using cotyledon and hypocotyls explants as described. A. tumefaciens LBA 4404 strains containing pBICaMV-AtGRXS17 or pMDC-CBF3 were used for generating stable transgenic lines.

3. Growth Condition and Tolerance Analyses of Tomato

T2 generation of AtGRXS17-expressing, AtCBF3-expressing, or wild-type tomato seeds were surface-sterilized, germinated, and grown on pots containing Miracle Gro (700) soil growing medium in growth chamber. The temperature of the growth chamber was maintained at 24° C./20° C. (day/night) under a 16-h photoperiod, and the light intensity was maintained at 300 μmol/$m^2$/sec. The plants were regularly watered and fertilized on a weekly basis with 20:20:20 fertilizer (Scotts, Marysville, Ohio). For the drought treatment, 4-week-old AtGRXS17-expressing and wild-type seedlings were withheld from watering for 12 days, and then re-watered. The phenotype and the chlorophyll fluorescence were measured during the drought treatment. For the cold treatment, 4-week-old AtGRXS17-expressing, AtCBF3-expressing or wild-type seedlings were treated at 4° C. (day/night) for 3 weeks in a walk-in growth chamber and then recovered in normal growth conditions for 5 days. Chlorophyll fluorescence was measured during the first 7-d chilling treatment. For oxidative stress treatment, 7-day-old AtGRXS17-expressing and wild-type seedlings grown on the MS media were transferred into the MS medium with or without 20 M methyl viologen (MV) in Magenta boxes and incubated for 14 days. The primary root length was then measured, and total RNA was extracted from the leaves.

4. Time-Course Analysis of Cold and Drought Stress-Responsive Genes

Cold and drought treatments were applied using 14-day-old AtGRXS17-expressing and wild-type seedlings grown in Petri dishes with MS medium. The treatment and sampling were designed according to previous reports of SlAREB1 and SlCBF1 with slight modifications (Zhang et al., Freezing-sensitive tomato has a functional CBF cold response pathway, but a CBF regulon that differs from that of freezing-tolerant *Arabidopsis*. The transcription factor SlAREB1 confers drought, salt stress tolerance and regulates biotic and abiotic stress-related genes in tomato. For cold treatment, the seedlings were moved to a growth chamber set at 4° C. The seedlings were harvested at 0, 0.5, 2, 4, 8, 24, and 48 h, respectively. For drought treatment, the seedlings were transferred and incubated in Petri dishes containing two layers of dry filter paper for 0, 0.5, 2, 4, 8, and 24 h, respectively. The seedlings after cold or drought treatments were harvested, and the RNA was extracted using the method described below.

5. RNA Extraction and qRT-PCR

Total RNA was isolated using the Qiagen Plant RNeasy kit from leaves of tomato plants according to the manufacturer's instructions. RNA for real time qRT-PCR was treated with RNase-free DNase prior to the synthesis of first-strand cDNA by oligo (dT) priming using moloney murine leukaemia virus-reverse transcriptase (BD Biosciences Clontech, Palo Alto, Calif., USA). One µL of the reverse transcription reaction solution was used as a template in a 25 µL PCR solution. Real-time PCR was performed in 25 µL reactions contain 10.5 µL cDNA, 1 µL 10 mM of each primer, and 12.5 µL SYBR Green PCR Master Mix (Bio-Rad Laboratories, Hercules, Calif.). Analysis was performed using the Bio-Rad IQ3 (Bio-Rad Laboratories). Primer efficiencies were measured and relative expression level was calculated using the comparative Ct method. SlPP2ACS was uses as a normalization control. The primers for PCR were listed in the Table in FIG. 25.

6. Electrolyte Leakage and Fv/Fm Ratio

Injury to plants was characterized by measuring chlorophyll fluorescence and electrolyte leakage of leaves. Chlorophyll fluorescence from the adaxial side of the leaf was monitored using a portable chlorophyll fluorometer (PEA, Hansatech Instruments, Ltd., UK). Photochemical efficiency of leaves as determined by chlorophyll fluorescence ratios (Fv/Fm) was monitored during and after the cold or drought treatment. Measurements were made during the light cycle on the leaves using the saturation pulse method after 30 min of dark adaption. For electrolyte leakage, tomato leaf samples were incubated in 15 ml of distilled water for 10 h to measure the initial electrolyte leakage using an YSI conductance meter (Model 32, YSI, Inc., Yellow Springs, Ohio, USA). The samples were subjected to 80° C. for 2 h to release the total electrolytes and then held at room temperature for 10 h. The final conductivity of the leachate was measured to determine the percent electrolyte leakage from the leaf samples.

7. Shoot Water Content

Shoot water content (SWC) was expressed as the difference between leaf fresh weight and dry weight, and calculated as follows: SWC=(fresh weight–dry weight)/dry weight.

Results

1. Response and Adaptation to Drought Stress in AtGRXS17-Expressing Tomato

Figure 26:
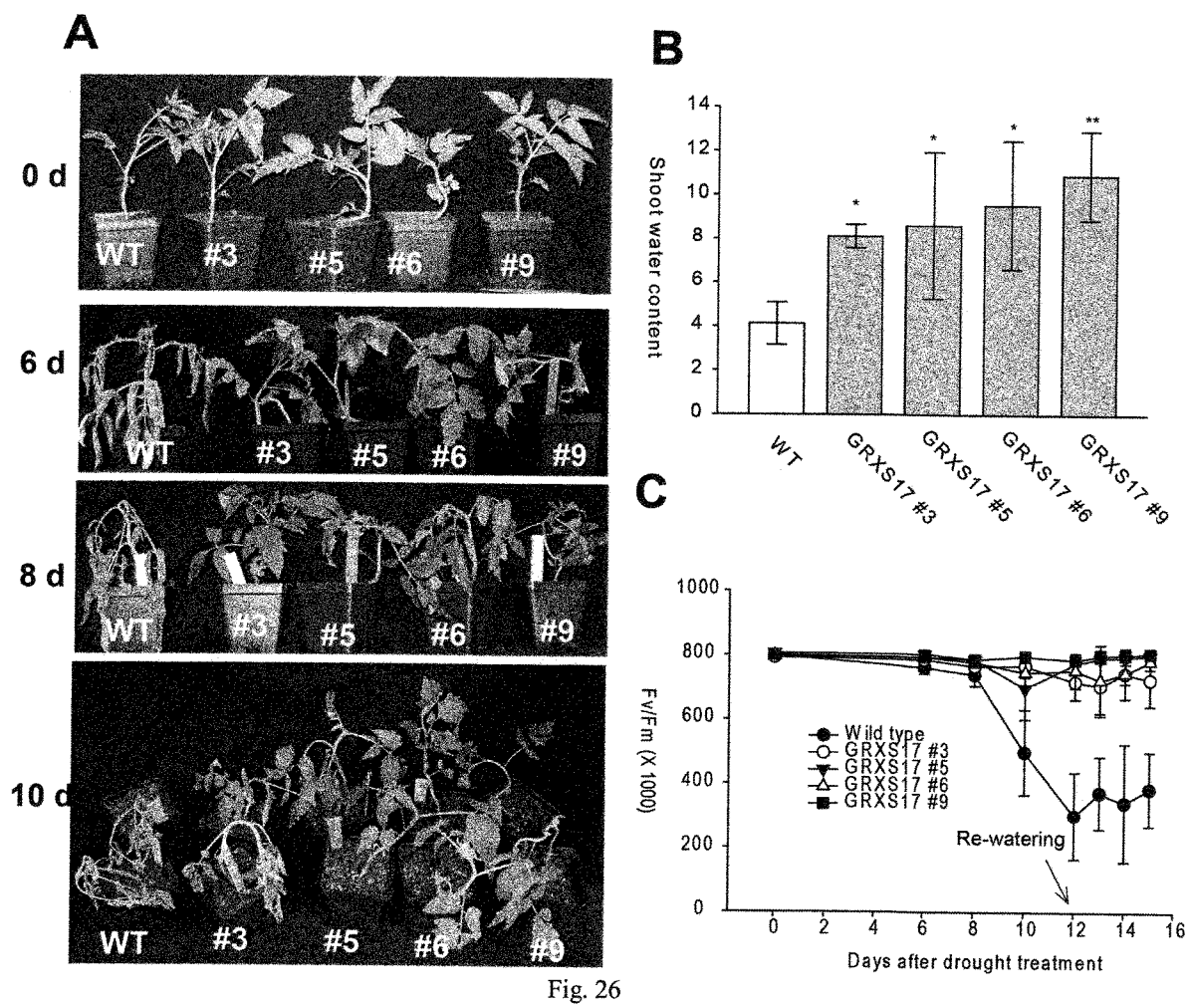
FIG. 26 shows (A) photographs of the morphology of AtGRXS17-expressing and wild-type plants before and after drought stress; (B) a graph of shoot water content of AtGRXS17-expressing and wild-type plants after 10-d withholding water; and (C) a graph of chlorophyll fluorescence of AtGRXS17-expressing and wild-type plants during drought treatment. Data represent mean±SD from three independent biological replicates (*P<0.05, ** P<0.01)

We initially tested if AtGRXS17-expressing tomato plants, which showed thermotolerance in examples above, confer drought tolerance. The AtGRXS17-expressing plants driven by the cauliflower mosaic virus (CaMV) 35S promoter had been generated previously, and homozygous lines (AtGRXS17-3, -5, -6 and -9) that contained single transgene insertions and displayed strong thermotolerance were used in this study. Four-week-old wild-type and AtGRXS17-expressing tomato plants (30 homozygous T2 plants derived from each of the four T1 transgenic lines) were subjected to drought treatment by withholding the water. Both wild-type and AtGRXS17-expressing tomato plants were affected by the drought stress. However, visible damage in wild-type plants in terms of leaf desiccation and wilt symptoms was more severe than that of AtGRXS17-expressing tomato plants (FIG. 26A). Concomitantly, AtGRXS17-expressing lines showed higher shoot water content compared to wild-type plants after 10-day drought treatment (FIG. 26B). In addition, AtGRXS17-expressing tomato plants showed higher Fv/Fm ratio compared to wild-type plants (FIG. 26C).

Figure 27:
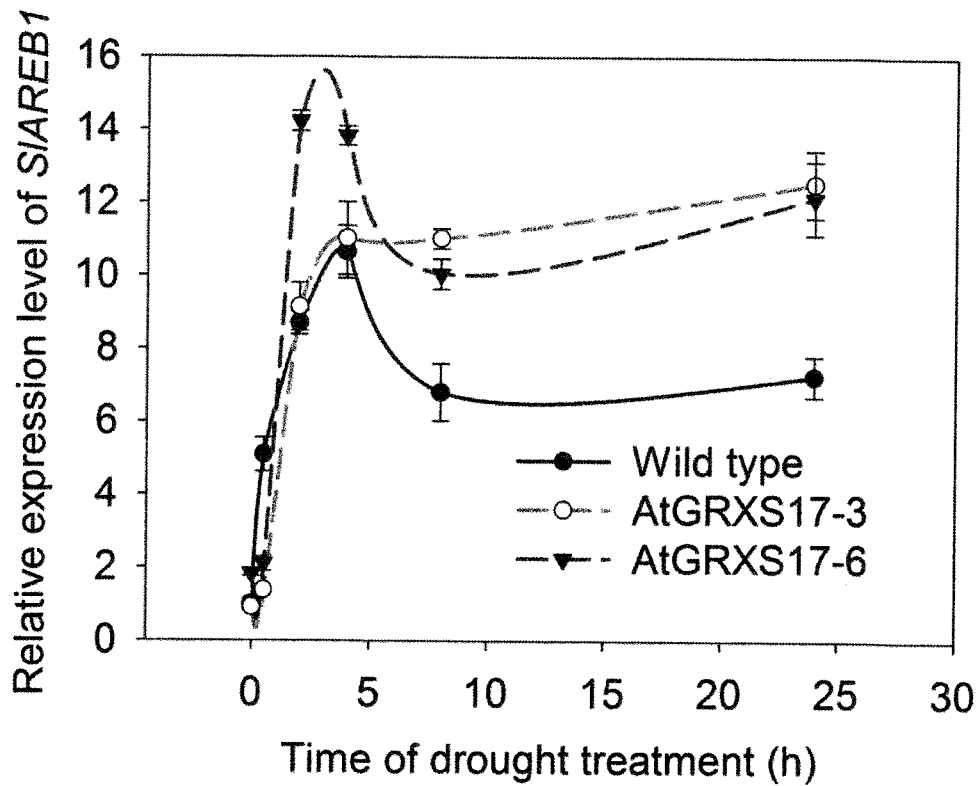
FIG. 27 shows a graph of the relative mRNA levels of SlABRE1 gene in 14-d-old AtGRXS17-expressing and wild-type tomato seedlings after being treated at 4° C. for 0, 0.5, 2, 4, 8, and 24 h, respectively. Data represent mean±SD from three independent biological replicates, and indicates that SlABRE1 transcripts remain longer at a higher level in AtGRXS17-expressing tomato plants under drought stress.

Effects of AtGRXS17 expression on the ABA signal pathway during drought stress were measured by conducting a time-course expression assay of ABA-dependent transcription factor gene SlAREB1. SlAREB1 expression peaked at 4 h and then started to decrease in both wild-type and transgenic lines. However, the abundance of SlAREB1 in AtGRXS17-expressing lines remained at a higher level than that of wild-type plants (FIG. 27).

2. Response and Adaptation to Cold Stress in AtGRXS17-Expressing Tomato

Figure 28:
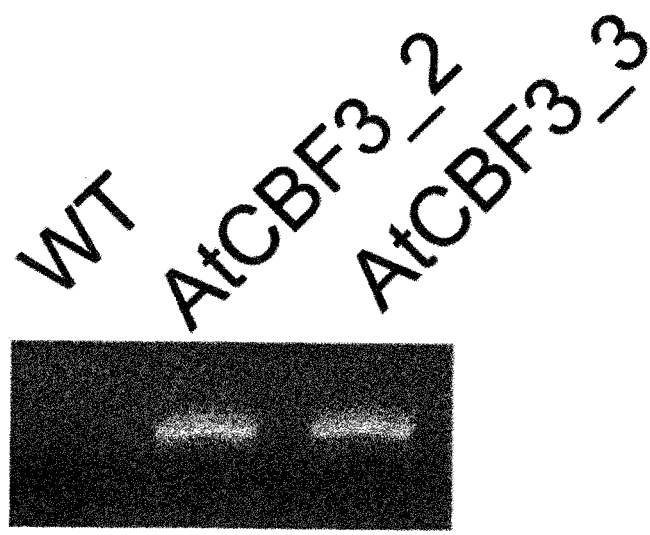
FIG. 28 is a PCR gel image of the integration of AtCBF3 into the tomato genome using HYG primers.
Figure 29:
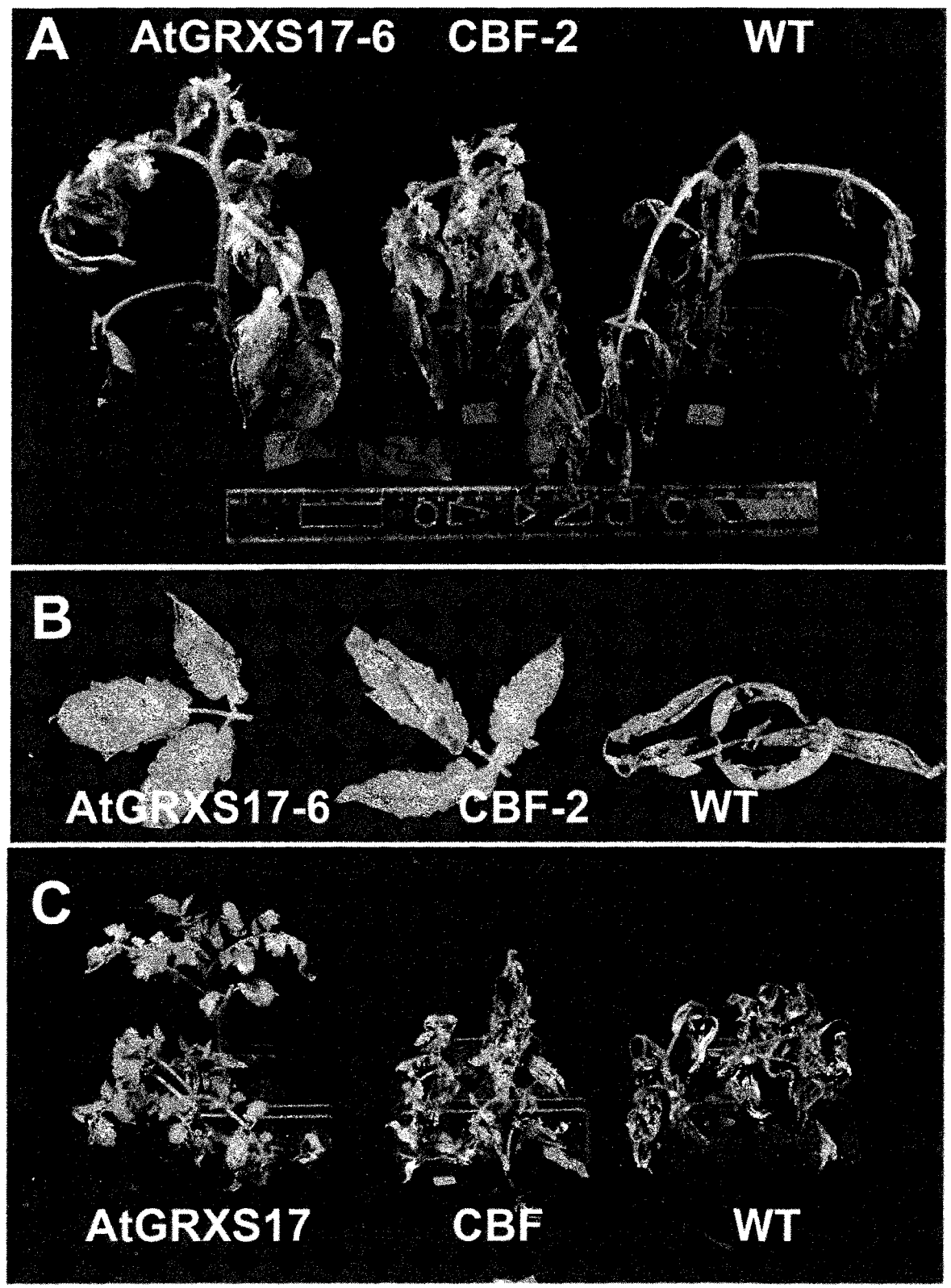
FIG. 29 shows photographs of (A) Four-week-old AtGRXS17-expressing, AtCBF3-expressing or wild-type seedlings treated under 4° C. (day/night) for 3 weeks; (B) AtGRXS17-expressing, AtCBF3-expressing and wild-type tomato leaves after cold treatment; and (C) Five-days recovery after 3-week-cold treatment.
Figure 31:
FIG. 31 is a photograph comparing the phenotypes of wild-type and AtCBF3-expressing tomato plants under normal growth condition.

To test cold tolerance, 4-week-old AtGRXS17-expressing (AtGRXS17-3, -5, -6 and -9) and wild-type tomato plants were treated at 4° C. for 3 weeks. For comparison, AtCBF3-expressing tomatoes were generated and treated simultaneously. CBF3 is a well characterized transcription factor that confers cold tolerance. The AtCBF3-expressing tomato plants (lines AtCBF3-2 and -3) were confirmed by PCR (FIG. 28) using HYG primers (SEQ ID NOs: 28-29). Thirty homozygous T2 plants derived from each of the six T1 transgenic lines (AtGRXS17-3, -5, -6 and -9 and AtCBF3-2 and -3) were analyzed, and the wild-type tomato plants showed more severe visible damage than AtCBF3- or AtGRXS17-expressing tomato plants (FIG. 29A, B, C). However, AtGRXS17-expressing tomato plants showed more vigorous growth than AtCBF3-expressing plants upon recovery for 5 days under normal growth condition [24/20° C. (day/night)] (FIG. 29C). The visual enhanced cold tolerance of both AtGRXS17- and AtCBF3-expressing plants was accompanied by lower electrolyte leakage when compared to wild-type after cold treatment, indicating reduced disruption of cell membranes in the transgenic lines (FIG. 30A). In addition, the chlorophyll fluorescence of both AtGRXS17- and AtCBF3-expressing plants was higher than that of wild-type (FIG. 30B). The phenotype of the AtGRXS17-expressing tomatoes is indistinguishable from the wild-type plants under normal growth conditions as shown in the Examples above, while AtCBF3-expressing tomato plants displayed stunted shape as compared to wild-type plants (FIG. 31).

Figure 32:
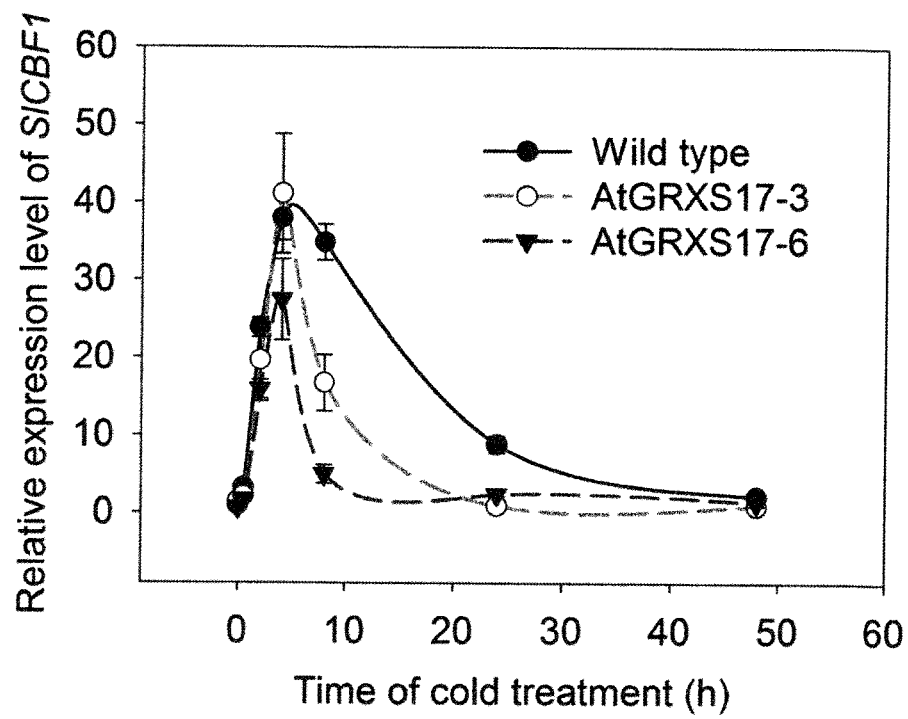
FIG. 32 is a graph of relative mRNA levels of SlCBF1 gene in 14-d-old wild-type and AtGRXS17-expressing tomato seedlings after being treated at 4° C. for 0, 0.5, 2, 4, 8, 24, and 48 h, respectively. Data represent mean±SD from three independent biological replicates, and indicate dynamic changes in SlCBF1 transcript levels of AtGRXS17-expressing tomato plants under cold stress.

Three tomato CBF genes have been characterized, and only SlCBF1 among those genes is strongly induced by cold treatment. SlCBF1 expression levels in both wild-type and AtGRXS17-expressing lines peaked at 4 h after cold stress, and no significant differences in expression were observed between wild-type and AtGRXS17-expressing lines (FIG. 32). However, expression levels of SlCBF1 in AtGRXS17-expressing lines returned more rapidly to resting level, in comparison to wild-type lines (FIG. 32).

3. AtGRXS17-Expressing Tomato Plants Improved Tolerance to Oxidative Stress

Figure 33:
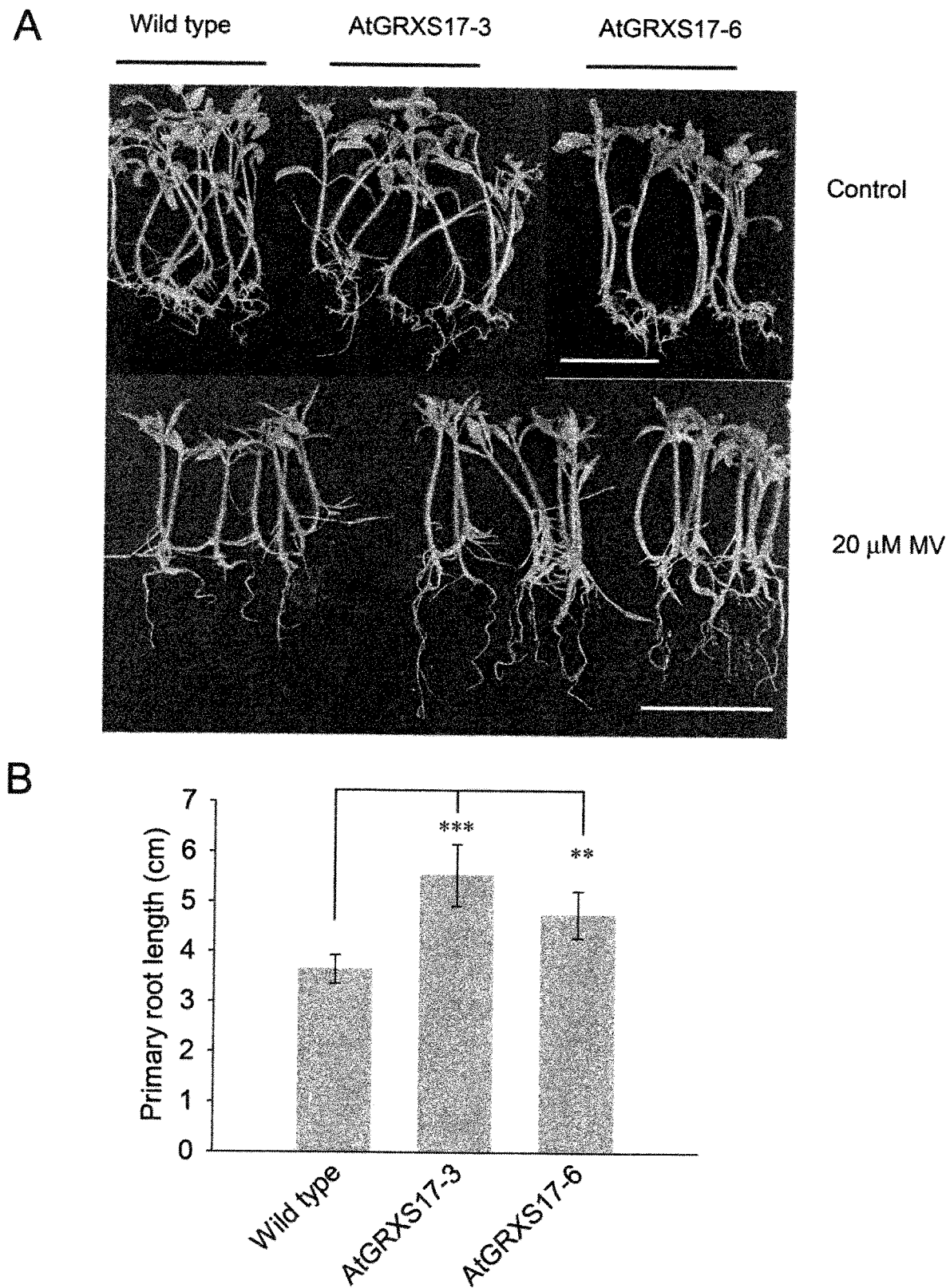
FIG. 33 is (A) photographs of AtGRXS17-expressing and wild-type tomato seedlings treated with oxidative herbicide. Seven-day-old AtGRXS17-expressing and wild-type tomato seedlings were transferred onto MS media with (lower panel) or without (upper panel) 20 M MV and incubated for 14 d. Bars=5 cm; and (B) a graph of the root length of wild-type and AtGRXS17-expressing tomato seedlings that were being treated by 20 M MV. Data represent mean±SD from eight independent biological replicates ( P<0.01, * P<0.001)

We hypothesized that AtGRXS17-expressing tomato plants might improve tolerance to oxidative stress as well. To examine this, 7-day-old wild-type and AtGRXS17-expressing tomato seedlings were incubated in MS media with or without methyl viologen (MV), a pro-oxidant herbicide that stimulates formation of ROS. The results showed that after 14 d of treatment, AtGRXS17-expressing tomato seedlings displayed more vigorous growth and had longer primary roots as compared to wild-type seedlings (FIG. 33), indicating that AtGRXS17 reduced oxidative damages caused by excess ROS accumulation.

Figure 34:
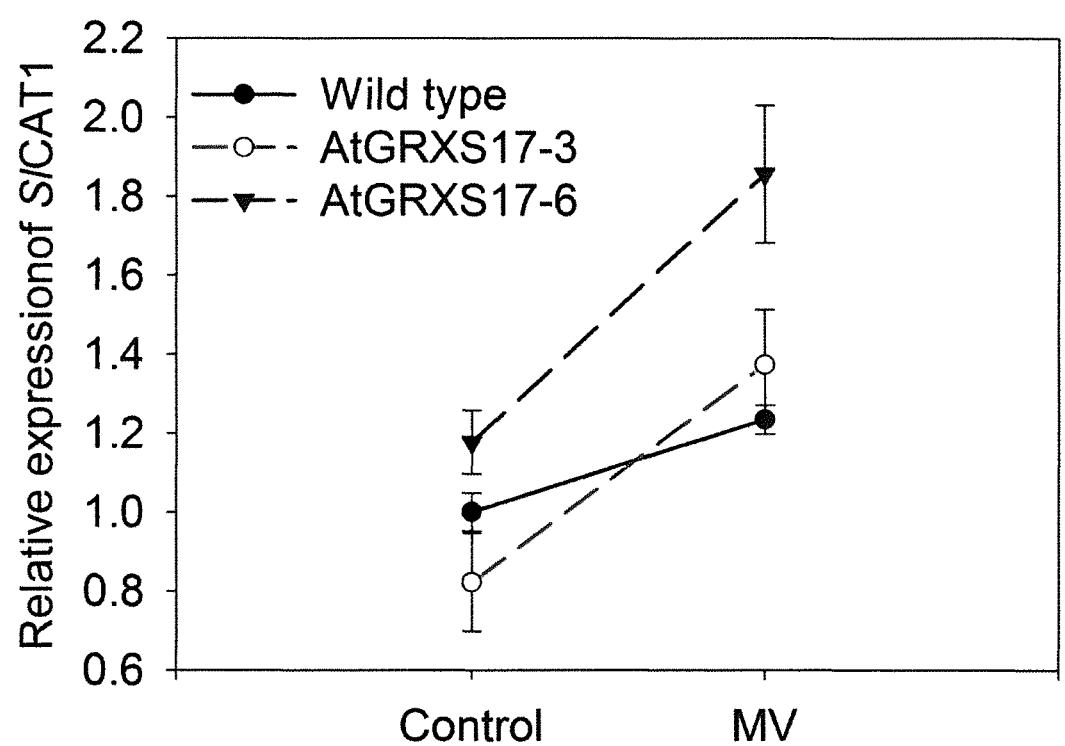
FIG. 34 is a graph of the relative mRNA levels of SlCAT1 gene in leaf tissue of AtGRXS17-expressing and wild-type plants exposed to oxidative stress. Data represent mean±SD from three independent biological replicates.

Catalase (CAT) plays important roles in ROS scavenging by converting $H_2O_2$ to $O_2$ and $H_2O$, and previous results indicated that ectopic expression of AtGRXS17 in tomato increases CAT activity under heat stress. To determine if the SlCAT1 expression level was altered under oxidative stress, qRT-PCR analysis was performed. The results demonstrated that the expression of SlCAT1 was significantly up-regulated in AtGRXS17-expressing lines as compared to wild-type after being treated by MV (FIG. 34).

Discussion Example 5

In this study, we investigated the effects of AtGRXS17 on drought and cold stress and demonstrated that ectopically expressed AtGRXS17 in tomato plants enhanced tolerance to cold, drought, and oxidative stress. Plants counteract abiotic stresses by modulating/interacting signaling pathways. The CBF/DREB1 pathway is a well-characterized cold response pathway, and extensive efforts have been made to improve cold (freezing and/or chilling) tolerance by manipulating CBF expression across different species. However, the CBF regulon differs between species, limiting the effectiveness of CBFs for engineering cold tolerant crop species. Expression of CBF3/DREB1a or SlCBF1 in *Arabidopsis*, for example, improves freezing tolerance while constitutive expression of either SlCBF1 or AtCBF3 in transgenic tomato plants does not increase freezing tolerance. However, here we showed that expression of AtCBF3 in tomato improved chilling tolerance in comparison to wild-type plants. Nonetheless, AtCBF3-expressing plants showed less protection against chilling stress than AtGRXS17-expressing tomato plants.

The induction of CBFs is one of the predominant responses to cold stress. Interestingly, our results demonstrated that ectopic expression of AtGRXS17 in tomato alters the response of endogenous SlCBF1 expression under chilling stress conditions. In addition, the elevated expression of SlCBF1 in AtGRXS17-expressing lines returned more rapidly to resting levels compared to wild-type lines, suggesting a potential direct correlation between AtGRXS17 and SlCBF1 in CBF signaling pathways under chilling stress. Despite the pivotal role of CBFs in cold tolerance, constitutive expression of either AtCBF3 or SlCBF1 in both *Arabidopsis* and tomato plants results in stunted growth. As demonstrated here, AtCBF3-expressing tomato plants also displayed stunted growth under normal growth condition. Feedback regulation by CBF plays an important role in regulating CBFs during normal cold acclimation. For example, CBF2 is a negative regulator of CBF1 and CBF3 expression during cold acclimation, while CBF3 negatively regulates CBF2 expression. In addition, MBY15 and ZAT12 also appear to function as negative regulator of CBFs. The lack of stunted growth in plants expressing AtGRXS17 indicates that the protein may both induce CBF1 expression and meliorate deleterious effects of the consequential rise in ROS. AtGRXS17 may have advantages for enhanced cold tolerance in different species.

Various strategies have been proposed for improving drought tolerance including promoting a vigorous root system, inducing stomatal closure, adjusting osmolytes, and minimizing oxidative damages. Ectopic expression of AtGRXS17 in tomato enhances drought tolerance presumably by up-regulating a key antioxidant gene SlCAT1 to improve ROS scavenging capability in plant cells or enhancing vigorous root system or both. Expression of AtGRXS17 may also alter endogenous drought responsive pathways, such as the ABA pathway, and, therefore, lead to improve drought tolerance in tomato plants. As part of the drought responsive signaling pathways, ABA plays a key role in regulating gene expression and stomatal aperture. Members of the AREB family have been implicated as essential components in ABA signaling pathway. For example, a protein of AREB family in tomato, SlAREB1, has been characterized and demonstrated to confer drought tolerance when overexpression in tomato, indicating SlAREB1 is an important component of ABA-dependent drought tolerance (Orellana et al. 2010). A dramatic up-regulation of SlAREB1 under drought stress was also observed in this study. SlAREB1 expression in AtGRXS17-expressing and wild-type tomato plants peak at 4 h. However, the abundance of SlAREB1 in AtGRXS17-expressing lines remains at a higher level longer than that of wild-type plants as shown by the data herein, suggesting that there may be a tight interaction between AtGRXS17 and ABA signaling during drought stress, which warrants further investigation.

AtGRXS17 relieves the defective growth of primary roots associated with increased accumulation or application of ROS. ROS are known to be accumulated during various abiotic stresses including both cold and drought stress, causing damage to cell membranes and other cellular components including DNA, proteins, and carbohydrates. Therefore, expression of AtGRXS17 into tomato plants may play an important role for the coordination of signaling and scavenging of ROS, resulting in enhanced tolerance to multiple abiotic stresses. Catalase, an $H_2O_2$ scavenger, is one of the most important enzymes in ROS-scavenging system. Ectopic expression of AtGRXS17 in tomato results in a more rapid response of SlCAT1 to oxidative stress compared to wild-type plants. Similarly, the activity of CAT was increased in the AtGRXS17-expressing plants when compared to wild-type plants after heat treatment as shown by the examples above. Therefore, AtGRXS17 may regulate CAT at the transcriptional and/or posttranscriptional level under abiotic stress conditions that give rise to oxidative stress.

Ectopic expression of a member of the glutaredoxin family, AtGRXS17, in tomato enhances tolerance to multiple abiotic stresses. Our working model for the effects of AtGRXS17-mediated tolerance to drought, cold, and oxidative stress involves both the regulation of stress response pathways and the enzymatic function of AtGRXS17 on ROS. Expression of AtGRXS17 inhibits CBF responsiveness during cold stress, but induces ABRE responsiveness during drought stress. Both cold and drought stress trigger the accumulation of ROS, causing oxidative stress. AtGRXS17 protects plant cells from oxidative stress and the protection against oxidative stress may be partly mediated through the up-regulation of CAT expression. Due to the universal existence of glutaredoxins in plant species, manipulation of glutaredoxins across different species may be a useful approach to improve tolerance to abiotic stresses and understand the plant signaling under abiotic stress conditions in many agriculturally important crop species.

The invention claimed is:

1. A method of producing a genetically-modified plant having enhanced tolerance to heat stress as compared to a control plant, said method comprising:
transforming a plant with a heterologous, abiotic stress tolerance gene to yield a genetically-modified plant having ectopic expression of said heterologous, abiotic stress tolerance gene, wherein said stress tolerance gene is *Arabidopsis* monothiol glutaredoxin AtGRXS17, wherein said gene encodes glutaredoxin GRXS17, thereby enhancing the tolerance of said genetically-modified plant to heat stress, and
wherein said genetically-modified plant is selected from the group consisting of wheat, oat, barley, rice, maize, millet, rye, sorghum, triticale, buckwheat, quinoa, soybeans, beans, peas, alfalfa, potatoes, sweet potatoes, cassava, yam, tomatoes, peppers, tobacco, and cotton.

2. The method of claim 1, wherein said transforming comprising:
introducing into said plant a nucleic acid construct for said heterologous, abiotic stress tolerance gene encoding said glutaredoxin; and
allowing said nucleic acid construct to be ectopically expressed in said plant.

3. The method of claim 2, wherein said nucleic acid construct comprises a nucleic acid coding sequence operably linked to a promoter that drives expression in said plant.

4. The method of claim 2, wherein the nucleic acid construct for said *Arabidopsis* monothiol glutaredoxin AtGRXS17 gene comprises a sequence selected from the group consisting of: (a) a nucleotide sequence comprising SEQ ID NO:1 or 3; (b) a nucleotide sequence comprising an antisense sequence corresponding to SEQ ID NO:1 or 3; and (c) a nucleotide sequence encoding a glutaredoxin protein comprising SEQ ID NO:2 or 4.

5. The method of claim 1, wherein said plant comprises a plant tissue, and said transforming comprising:

culturing said tissue on media; and
introducing said heterologous, abiotic stress tolerance gene into the cells of said tissue to yield transformed tissue.

6. The method of claim 5, further comprising:
regenerating whole plants from said tissue, wherein said regenerated plants have enhanced tolerance to heat stress.

7. The method of claim 6, wherein said regenerating comprises:
inducing callus formation from said transformed tissue;
regenerating shoots; and
rooting of said shoots in rooting media to regenerate said whole plant.

8. The method of claim 5, wherein said introducing is selected from the group consisting of: *Agrobacterium*-mediated transformation, PEG-mediated uptake, electroporation-mediated uptake, particle bombardment-mediated delivery, and microinjection.

9. The method of claim 1, wherein said genetically-modified plant comprises an identical phenotype as compared to said control plant when said plants are grown under non-stress conditions.

10. The method of claim 1, said method further comprising inhibiting the expression, activity, or function of an endogenous glutaredoxin gene of said genetically-modified plant.

11. The method of claim 1, said method further comprising: crossing said genetically-modified plant with a second plant to thereby produce progeny having enhanced tolerance to heat stress.

12. The method of claim 11, wherein said progeny is homozygous for *Arabidopsis* monothiol glutaredoxin AtGRXS17.

13. The method of claim 11, wherein said second plant has a characteristic selected from the group consisting of: pest resistance, herbicide resistance, geographic adaptation, and increased stalk strength.

14. The method of claim 1, said method further comprising self-pollinating said genetically-modified plant to thereby produce genetically-modified seed, wherein said seed comprises said heterologous, abiotic stress tolerance gene.

\* \* \* \* \*